(12) United States Patent
Kirn et al.

(10) Patent No.: US 11,802,278 B2
(45) Date of Patent: *Oct. 31, 2023

(54) CODON OPTIMIZED GLA GENES AND USES THEREOF

(71) Applicant: 4D MOLECULAR THERAPEUTICS INC., Emeryville, CA (US)

(72) Inventors: David H. Kirn, Emeryville, CA (US); Melissa Kotterman, Emeryville, CA (US); Peter Francis, Emeryville, CA (US); David Schaffer, Emeryville, CA (US); Paul Szymanski, Emeryville, CA (US); Kevin Whittlesey, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,650

(22) Filed: Oct. 11, 2022

(65) Prior Publication Data
US 2023/0190964 A1    Jun. 22, 2023

Related U.S. Application Data

(63) Continuation of application No. PCT/US2021/029146, filed on Apr. 26, 2021.

(60) Provisional application No. 63/114,195, filed on Nov. 16, 2020, provisional application No. 63/016,207, filed on Apr. 27, 2020.

(51) Int. Cl.
| | | |
|---|---|---|
| C12N 9/40 | (2006.01) | |
| A61K 9/00 | (2006.01) | |
| A61P 3/00 | (2006.01) | |
| C12N 15/86 | (2006.01) | |
| A61K 48/00 | (2006.01) | |

(52) U.S. Cl.
CPC ......... *C12N 9/2465* (2013.01); *A61K 9/0019* (2013.01); *A61K 48/0066* (2013.01); *A61K 48/0075* (2013.01); *A61K 48/0083* (2013.01); *A61P 3/00* (2018.01); *C12N 15/86* (2013.01); *C12Y 302/01022* (2013.01); *A61K 48/00* (2013.01); *C12N 2840/00* (2013.01)

(58) Field of Classification Search
CPC ............ A61K 48/0066; A61K 48/0075; A61K 48/0083; A61K 9/0019; C12N 9/2465; C12N 15/86; C12N 2480/00; A61P 3/00
See application file for complete search history.

(56) References Cited

U.S. PATENT DOCUMENTS

2019/0000932 A1    1/2019    Martini et al.

FOREIGN PATENT DOCUMENTS

| WO | 2002/064799 A2 | 8/2002 |
| WO | 2016/181122 A1 | 11/2016 |
| WO | 2019/060454 A2 | 3/2019 |
| WO | 2020/198685 A1 | 10/2020 |

OTHER PUBLICATIONS

International Search Report of PCT/US2021/029146 dated Aug. 24, 2021.
Written Opinion of PCT/US2021/029146 dated Aug. 24, 2021.
AU 2021263563—Certificate of Patent Grant and description and claims as accepted.

*Primary Examiner* — Paul J Holland
(74) *Attorney, Agent, or Firm* — Much Shelist, P.C.; Christopher M. Cabral

(57) ABSTRACT

The present disclosure provides codon optimized nucleotide sequences encoding human alpha-galactosidase A, vectors, and host cells comprising codon optimized alpha-galactosidase A sequences, and methods of treating disorders such as Fabry disease comprising administering to the subject a codon optimized sequence encoding human alpha-galactosidase A.

10 Claims, 25 Drawing Sheets
Specification includes a Sequence Listing.

Banding Technique: GTL  Band Resolution: Good
Metaphases Counted: 20  Analyzed: 7  Karyotyped: 2

RESULTS: 46,XY[20]  Apparently NORMAL Human Male Karyotype

Non-clonal Aberrations: None

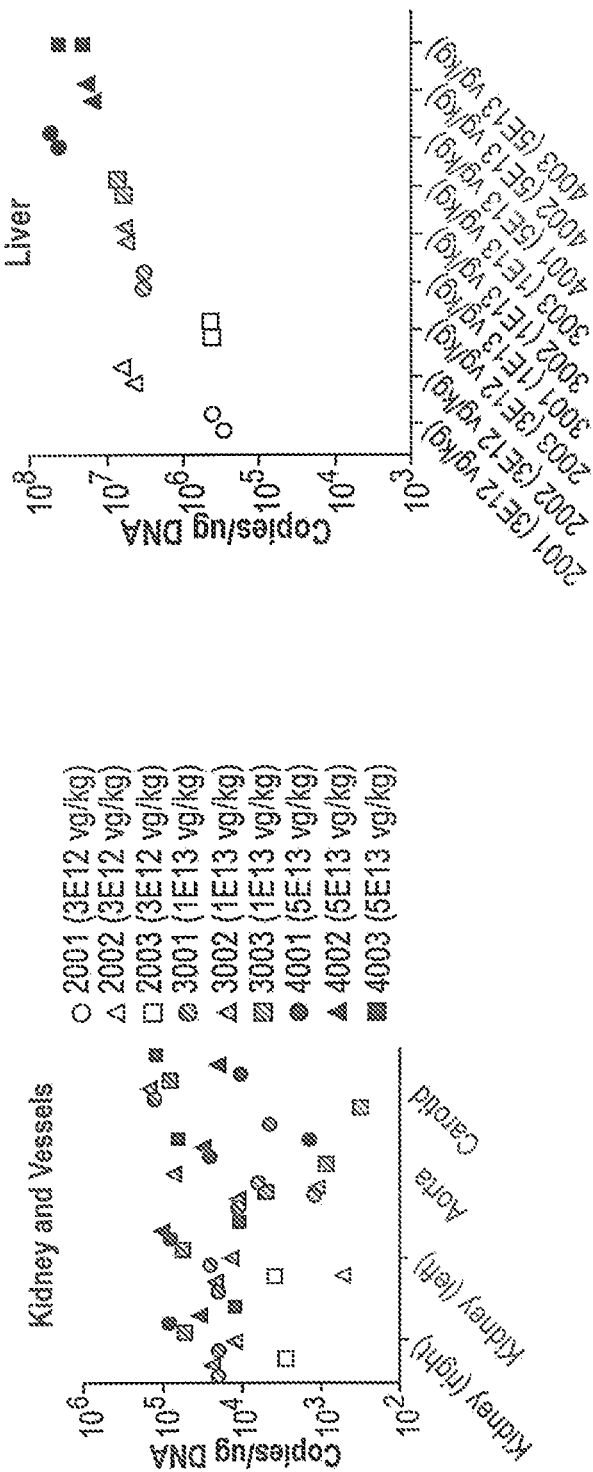
Figure 15 (Concluded)

Plasma AGA – Dose Group Means

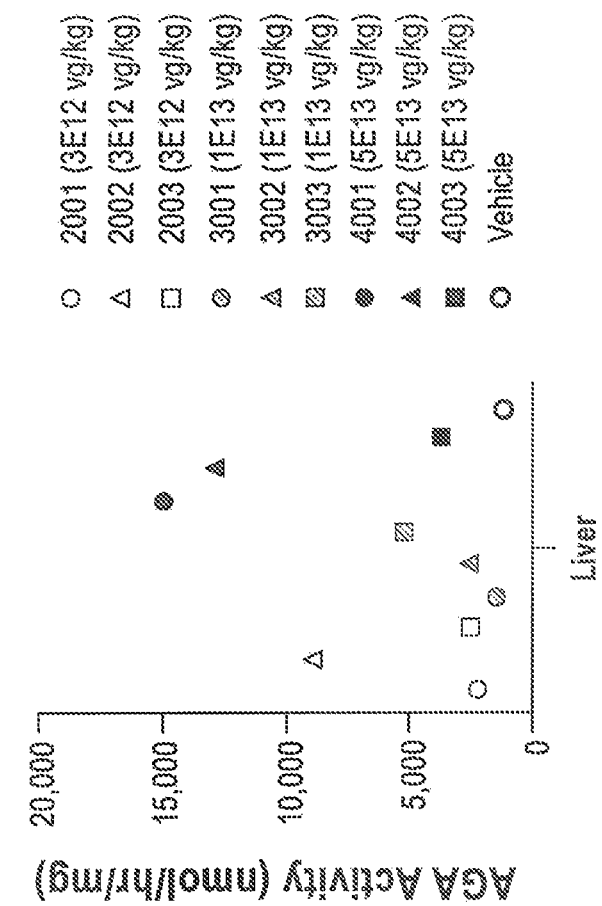
Figure 19 (Concluded)

Vehicle: 100I-29

4D-310 5X10E13: 400I-29

4D-310 5X10E13: 4002-29

4D-310 5X10E13: 4003-29

Vehicle: 100I-30

4D-310 5X10E13: 400I-30

4D-310 5X10E13: 4002-30

4D-310 5X10E13: 4003-30

SEQUENCE LISTING

```
Sequence total quantity: 9
SEQ ID NO: 1              moltype = DNA  length = 1290
FEATURE                   Location/Qualifiers
misc_feature              1..1290
                          note = codon optimized GLA
source                    1..1290
                          mol_type = other DNA
                          organism = synthetic construct
SEQUENCE: 1
atgcagctgc ggaatcctga actgcacctg ggatgtgccc tggctctgag atttctggcc   60
ctggtgtctt gggacatccc tggcgctaga gccctggata atggcctggc cagaacacct  120
acaatgggct ggctgcactg ggagagattc atgtgcaacc tggactgcca agaggaaccc  180
gacagctgca tcagcgagaa gctgttcatg gaaatggccg agctgatggt gtccgaaggc  240
tggaaggatg ccggctacga gtacctgtgc atcgacgact gttggatggc ccctcagaga  300
gactctgagg gcagactgca agccgatcct cagagattcc ctcacggcat cagacagctg  360
gccaactacg tgcacagcaa gggcctgaag ctgggcatct atgccgacgt gggcaacaag  420
acctgtgccg gctttcctgg cagcttcggc tactacgata tcgacgccca gaccttcgcc  480
gattgggaag tcgatctgct gaagttcgac ggctgctact gcgacagcct ggaaaatctg  540
gccgacggct acaagcacat gtcactggcc ctgaatcgga ccggcagatc catcgtgtac  600
agctgcgagt ggcccctgta catgtggccc ttccagaagc ctaactacac cgagatcaga  660
cagtactgca accactggcg gaacttcgcc gacatcgacg atagctggaa gtccatcaag  720
agcatcctgg actggaccag cttcaatcaa gagcggatcg tggacgtggc aggacctggc  780
ggatggaacg atcctgacat gctggtcatc ggcaacttcg gcctgagctg gaaccagcaa  840
gtgacccaga tggccctgtg ggccattatg gccgctcctc tgttcatgag caacgacctg  900
agacacatca gccctcaggc caaggctctg ctccaggaca aggatgtgat cgctatcaac  960
caggatcctc tgggcaagca gggctaccag ctgagacagg gcgacaattt cgaagtgtgg 1020
gaaagacccc tgagcggact ggcttgggcc gtcgccatga tcaacagaca agagatcggc 1080
ggaccccggt cctacacaat tgcctggcct tctctcggca aaggcgtggc ctgtaatccc 1140
gcctgcttta tcacacagct gctgcccgtg aagagaaagc tgggctttta cgagtggacc 1200
agcagactgc ggagccacat caatcctacc ggcacagtgc tgctgcaact ggaaaacaca 1260
atgcagatga gcctgaagga cctgctctaa                                   1290

SEQ ID NO: 2              moltype = AA  length = 429
FEATURE                   Location/Qualifiers
source                    1..429
                          mol_type = protein
                          organism = Homo sapiens
SEQUENCE: 2
```

```
MQLRNPELHL GCALALRFLA LVSWDIPGAR ALDNGLARTP TMGWLHWERF MCNLDCQEEP    60
DSCISEKLFM EMAELMVSEG WKDAGYEYLC IDDCWMAPQR DSEGRLQADP QRFPHGIRQL   120
ANYVHSKGLK LGIYADVGNK TCAGFPGSFG YYDIDAQTFA DWGVDLLKFD GCYCDSLENL   180
ADGYKHMSLA LNRTGRSIVY SCEWPLYMWP FQKPNYTEIR QYCNHWRNFA DIDDSWKSIK   240
SILDWTSFNQ ERIVDVAGPG GWNDPDMLVI GNFGLSWNQG VTQMALWAIM AAPLFMSNDL   300
RHISPQAKAL LQDKDVIAIN QDPLGKQGYQ LRQGDNFEVV ERPLSGLAWA VAMINRQEIG   360
GPRSYTIAVA SLGKGVACNP ACFITQLLPV KRKLGFYEWT SRLRSHINPT GTVLLQLENT   420
MQMSLKDLL                                                          429

SEQ ID NO: 3            moltype = DNA  length = 1290
FEATURE                 Location/Qualifiers
source                  1..1290
                        mol_type = other DNA
                        organism = Homo sapiens
SEQUENCE: 3
atgcagctga ggaacccaga actacatctg gctgcgcgc ttgcgcttcg cttcctggcc     60
ctcgtttcct gggacatccc tggggctaga gcactggaca tggattggc aaggacgcct    120
accatgggct ggctgcactg ggagcgcttc atgtgcaaca ttgactgcca ggaagagcca   180
gattcctgca tcagtgagaa gctcttcatg gagatggcag agctcatggt ctcagaaggc   240
tggaaggatg caggttatga gtacctctgc attgatgact gttggatggc tcccaaaga    300
gattcagaag gcagacttca ggcagaccct cagcgctttc ctcatgggat cgccagcta    360
gctaattatg ttcacagcaa aggactgaag ctagggatt atgcagatgt tggaaataaa    420
acctgcgcag gcttccctgg agttttgga tactacgaca ttgatgccca gacctttgct    480
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctctta tatgtggccc ttcaaaagc ccaattatac agaaatccga      660
cagtactgca atcactggcg aaattttgct gacattgatg attcctggaa agtataaag    720
agtatcttgg actggacatc ttttaaccag gagagaattg ttgatgttgc tggaccaggg    780
ggttggaatg acccagatat gttagtgatt ggaactttg gcctcagctg aatcagcaa     840
gtaactcaga tggcccctg gctatcatg gctgctcatt tattcatgtc taatgacctc     900
cgacacatca gccctcaagc caaagctctc cttcaggata aggacgtaat tgccatcaat    960
caggaccct tgggcaagca agggtaccag cttagacagg gagacaactt tgaagtgtgg    1020
gaacgacctc tctcaggctt agcctgggct gtagctatga taaaccggca ggagattggt   1080
ggacctcgct cttataccat cgcagttgct tccctgggta aaggagtggc ctgtaatcct   1140
gcctgcttca tcacacagct cctccctgtg aaaaggaagc tagggttcta tgaatggact   1200
tcaaggttaa gaagtcacat aaatcccaca ggcactgttt tgcttcagct agaaaataca   1260
atgcagatgt cattaaaaga cttactttaa                                    1290

SEQ ID NO: 4            moltype = AA  length = 745
FEATURE                 Location/Qualifiers
REGION                  1..745
                        note = Variant AAV capsid protein
source                  1..745
                        mol_type = protein
                        organism = synthetic construct
SEQUENCE: 4
MAADGYLPDW LEDTLSEGIR QWWKLKPGPP PKPAERHKD DSRGLVLPGY KYLGPFNGLD     60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAN KTTNKDARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSINV   720
DFTVDTNGVY SEPRPIGTRY LTRNL                                        745

SEQ ID NO: 5            moltype = DNA  length = 1664
FEATURE                 Location/Qualifiers
misc_feature            1..1664
                        note = CAG promoter
source                  1..1664
                        mol_type = other DNA
                        organism = synthetic construct
SEQUENCE: 5
actagttatt aatagtaatc aattacgggg tcattagttc atagcccata tatggagttc     60
cgcgttacat aacttacggt aaatggcccg cctggctgac cgcccaacga ccccgcccca   120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc ccctattga cgtcaatgac ggtaaatggc ccgcctggca ttatgcccag   300
tacatgacct tatgggactt tcctacttgg cagtacatct acgtattagt cagcgctatt   360
accatggtcg aggtgagccc cacgttctgc ttcactctcc ccatctcccc ccctccca    420
cccccaattt tgtatttatt tattttttaa ttattttgtg cagcgatggg ggcggggggg   480
ggggggggc gcgcgccagg cggggcgggg cgggcgaggc ggcggggcgg ggcgaggcgg    540
agaggtgcgg cggcagccaa tcagagcggc gcgctccgaa agtttccttt tatggcgagg   600
cggcggcggc ggcggcccta taaaaagcga agcgcgcggc gggcggggag tcgctgcgac   660
```

```
gctgccttcg ccccgtgccc cgctccgccg ccgcctcgcg ccgcccgccc cggctctgac   720
tgaccgcgtt actcccacag gtgagcgggc gggacggccc ttctcctccg gctgtaatt   780
agcgcttggt ttaatgacgg cttgtttctt ttctgtggct gcgtgaaagc cttgaggggc   840
tccgggaggg ccctttgtgc gggggagcg gctcggggg tgcgtgcgtg tgtgtgtgcg   900
tggggagcgc cgcgtgcggc tccgcgctgc ccggcgcgtg tgagcgctgc gggcgcggcg   960
cggggcttg tgcgctccgc agtgtgcgcg agggagcgc ggccgggggc ggtgccccgc  1020
ggtgcggggg gggctgcgag gggaacaaag gctgcgtgcg gggtgtgtgc gtgggggggt  1080
gagcaggggg tgtgggcgcg tcggtcgggc tgcaacccc cctgcacccc ctccccgag  1140
ttgctgagca cggcccggct tcgggtgcgg ggctccgtac ggggcgtggc gcggggctcg  1200
ccgtgccggg cggggtgg cggcaggtgg gggtgccggg ccgcctcggg  1260
ccgggaggg ctcggggag gggcgcggcg gcccccggag cgccggcggc tgtcgaggcg  1320
cggcgagccg cagccattgc cttttatggt aatcgtgcga gagggcgcag ggacttcctt  1380
tgtcccaaat ctgtgcggag ccgaaatctg gaggcgccg ccgcacccc tctagcgggc  1440
gcggggcgaa gcggtgcggc gccggcagga aggaaatggg ggggagggcc cttcgtgcgt  1500
cgccgcgccg ccgtcccctt ctccctctcc agcctcgggg ctgtccgcgg gggacggct  1560
gccttcgggg gggacggggc agggcggggt tcggcttctg cgtgtgaccg gcggctcta  1620
gagcctctgc taaccatgtt catgccttct tctttttcct acag            1664

SEQ ID NO: 6              moltype = DNA   length = 3616
FEATURE                   Location/Qualifiers
misc_feature              1..3616
                          note = AAV expression construct
source                    1..3616
                          mol_type = other DNA
                          organism = synthetic construct
SEQUENCE: 6
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg   120
gccaactcca tcactagggg ttcctatcga ttgaattccc cggggatcca ctagttatta   180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
gtatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatggtcga   540
ggtgagcccc acgttctgct tcactctccc catctccccc cctccccac cccaattttt   600
gtatttattt atttttaat tatttgtgc agcgatgggg gcgggggggg gggggggcg   660
cgcgccaggc gggcgggc ggggcgaggg gcgggcggg gcgaggcgga gaggtgcggc   720
ggcagccaat cagagcggcg cgctccgaaa gtttcctttt atggcgaggc ggcggcggcg   780
gcggccctat aaaaagcgaa gcgcgcggcg ggcggggagt cgctgcgacg ctgccttcgc   840
cccgtgcccc gctccgccgc cgcctcgcgc cgcccgcccc ggctctgact gaccgcgtta   900
ctcccacagg tgagcgggcg gacggccct tctcctccgg ctgtaatta gcgcttggtt   960
taatgacggc ttgtttcttt tctgtggctg cgtgaaagcc ttgaggggct ccgggaggc  1020
cctttgtgcg gggggagcgg ctcgggggt gcgtgcgtgt gtgtgtgcgt gggggagcgc  1080
gcgtgcggct ccgcgctgcc cggcggcgt gagcgctgcg ggcgcggcgc gggcttgt  1140
gcgctccgca gtgtgcgcga gggagcgcg gccgggggc gtgccccgcg gtgcgggggg  1200
ggctgcgagg gaacaaagg ctgcgtgcgg ggtgtgtgc agcagggggt  1260
gtgggcgcgt cggtcgggct gcaacccccc ctgcacccc ctccccgagt tgctgagcac  1320
ggcccggctt cgggtgcggg gctccgtacg gggcgtggcg cggggctcgc cgtgccggc  1380
gggggtggc ggcaggtggg ggtgccgggc ggggcgggc cgcctcgggc cggggagggc  1440
tcggggaagg gcgcggcgc ccccggagc gccggcggc gtcgaggcgc ggcgagccgc  1500
agccattgcc ttttatggta atcgtgcgag agggcgcagg gacttccttt gtcccaaatc  1560
tgtgcggagc cgaaatctgg aggcgccgc cgcaccccct ctagcgggcg cggggcgaag  1620
cggtgcggcc ccggcaggaa ggaaatgggg gggagggcc ttcgtgcgtc gccgcgccgc  1680
cgtcccccttc tccctctcca gcctcggggc tgtccgcggg ggacggctc ccttcggggg  1740
ggacggggca gggcggggtt cggcttctgc gtgtgaccgg cggctctag agcctctgct  1800
aaccatgttc atgccttctt ctttttccta cagtctagag tcgacctgca ggtggatatc  1860
ttgctagcac gccaccatgc agctgcgaa tcctgaactg cacctgggat gtgccctggc  1920
tctgagattt ctgccctgg tgtcttggga catcccctgg gctagagcc tggataatgg  1980
cctggccaga acacctacaa tgggctggct gcactgggaa agattcatgt gcaacctgga  2040
ctgccaagag gaacccgaca gctgcatcag cgagaagctg ttcatggaaa tggccgagct  2100
gatggtgtcc gaaggctgga aggatgccgg ctacgagtac ctgtgcatcg acgactgttg  2160
gatggccct cagagagact ctgagggcag actgcaagcg atcctcaga gattccctca  2220
cggcatcaga cagctggcca actactgca cagcaaggc ctgaagctgg gcatctatgc  2280
cgacgtgggc aacaagacct gtgccggctt tcctggcagc ttcggctact acgatatcga  2340
cgcccagacc ttcgccgatt ggggagtcga tctgctgaag ttcgacggct gctactgcga  2400
cagcctggaa aatctggccg acggctacaa gcacatgtca ctggccctga atcggaccgg  2460
cagatccatc gtgtacagct gcgagtggcc cctgtacatg tggccttcc agaagcctaa  2520
ctacaccgag atcagacagt actgcaacca ctggcgaacc ttcgccgaca tcgacgatag  2580
ctggaagtcc atcaagagca tcctggactg gaccagcttc aatcaagagc ggatcgtgga  2640
cgtggcagga cctggcggat ggaacgatcc tgacatgctg gtcatcggca acttcggcct  2700
gagctggaac cagcaagtga cccagatggc cctgtgggcc attatggccg ctcctctgtt  2760
catgagcaac gacctgagac acatcagccc tcaggccaag gctctgctcc aggacaagga  2820
tgtgatgct atcaaccagg atcctctggg caagcaggga taccagctga cagcagggcg  2880
caattttcga agtgtgggaaa gaccctgag cggactggct tgggccgtcg ccatgatcaa  2940
cagacaagg atcggcggac cccggtccta cacaattgcc gtgcttctc tcggcaaagg  3000
cgtggcctgt aatcccgcct gctttatcac acagctgctg cccgtgaaga gaaagctggg  3060
cttttacgag tggaccagca gactgcggag ccacatcaat cctaccggca cagtgctgct  3120
gcaactggaa aacacaatgc agatgagcct gaaggaccctg ctctaagcca cgcgtaacac  3180
```

```
gtgcatgcga gagatctgcg gccgcgagct cggggatcca gacatgataa gatacattga  3240
tgagtttgga caaaccacaa ctagaatgca gtgaaaaaaa tgctttattt gtgaaatttg  3300
tgatgctatt gctttatttg taaccattat aagctgcaat aaacaagtta acaacaacaa  3360
ttgcattcat tttatgtttc aggttcaggg ggaggtgtgg gaggttttt aaagcaagta   3420
aaacctctac aaatgtggta tggctgatta tgatcaatgc atcctagccg gaggaacccc  3480
tagtgatgga gttggccact ccctctctgc gcgctcgctc gctcactgag gccgcccggg  3540
caaagcccgg gcgtcgggcg acctttggtc gcccggcctc agtgagcgag cgagcgcgca  3600
gagagggagt ggccaa                                                 3616

SEQ ID NO: 7             moltype = AA  length = 7
FEATURE                  Location/Qualifiers
source                   1..7
                         mol_type = protein
                         organism = synthetic construct
SEQUENCE: 7
NKTTNKD                                                           7

SEQ ID NO: 8             moltype = AA  length = 10
FEATURE                  Location/Qualifiers
source                   1..10
                         mol_type = protein
                         organism = synthetic construct
SEQUENCE: 8
LANKTTNKDA                                                        10

SEQ ID NO: 9             moltype = AA  length = 735
FEATURE                  Location/Qualifiers
source                   1..735
                         mol_type = protein
                         organism = adeno-associated virus 2
SEQUENCE: 9
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735
```

CODON OPTIMIZED GLA GENES AND USES THEREOF

CROSS-REFERENCE TO RELATED APPLICATIONS

This application is a continuation of international patent application number PCT/US2021/029146, filed Apr. 26, 2021, which claims the benefit of U.S. Provisional Patent Application Nos. 63/114,195, filed Nov. 16, 2020 and 63/016,207, filed Apr. 27, 2020, the entire contents of each of which is incorporated herein by reference.

SEQUENCE LISTING SUBMISSION VIA EFS-WEB

A computer readable XML file, entitled "090400-5014-US 01-Sequence-Listing" created on or about Oct. 6, 2022, with a file size of about 20,000 bytes, contains the sequence listing for this application and is hereby incorporated by reference in its entirety

BACKGROUND OF THE INVENTION

Fabry disease is an X-linked disorder in which mutations in the GLA gene (encoding α-galactosidase A, AGA) result in reduced or absent AGA enzyme activity and consequent accumulation of globotriaosylceramide (Gb3). Gb3 is considered cytotoxic to cardiomyocytes and endothelial cells (kidney/heart/neuron) resulting in significant morbidity and shortened life expectancy. Administration of recombinant AGA (ERT) appears to slow disease progression in some tissues. Likely due to poor uptake into cells, for example in the heart, there remains significant unmet medical need. In addition, cardiovascular disease remains the most common cause of mortality in Fabry disease (75% of all known deaths). Thus, there is a compelling need for a durable treatment such as a single administration intravenous gene therapeutic targeted to key tissues that express GLA cell-autonomously, reducing Gb3 and thereby improving clinical outcomes.

One impediment with respect to cardiac gene therapy is insufficient transduction of human cardiomyocytes following intravenous administration. Current AAV vectors in development traffic predominantly to the liver and are not targeted to heart tissue. Wild-type AAV1 has been evaluated clinically, but ultimately did not result in an improvement in the primary endpoint of recurrent heart failure events compared to placebo. Novel heart targeted AAV variants may provide effective treatment of Fabry disease cardiomyopathy.

SUMMARY OF THE INVENTION

Disclosed are codon optimized nucleic acid molecules encoding a human galactosidase A (AGA) protein. In one aspect, the disclosure provides a nucleic acid comprising the nucleotide sequence of SEQ ID NO: 1 or a nucleic acid comprising a nucleotide sequence at least 90%, at least 95%, at least 96%, at least 97%, at least 98%, or at least 99% identical to the nucleotide sequence of SEQ ID NO:1 and which encodes a human AGA polypeptide having the amino acid sequence of SEQ ID NO:2. In some embodiments, a nucleic acid comprising or consisting of the nucleotide sequence of SEQ ID NO: 1 is provided. In related embodiments, the nucleic acid is expressed at a higher level compared with the level of expression of a wild type GLA nucleic acid sequence (e.g. SEQ ID NO:3) in an otherwise identical cell. SEQ ID NO:3 (consensus CDS sequence no. CCDS14484.1; www.uniprot.org/uniprot/Q7X1P3) is set forth below:

```
(SEQ ID NO: 3)
ATGCAGCTGAGGAACCCAGAACTACATCTGGGCTGCGCGCTTGCGCTTCGC

TTCCTGGCCCTCGTTTCCTGGGACATCCCTGGGGCTAGAGCACTGGACAAT

GGATTGGCAAGGACGCCTACCATGGGCTGGCTGCACTGGGAGCGCTTCATG

TGCAACCTTGACTGCCAGGAAGAGCCAGATTCCTGCATCAGTGAGAAGCTC

TTCATGGAGATGGCAGAGCTCATGGTCTCAGAAGGCTGGAAGGATGCAGGT

TATGAGTACCTCTGCATTGATGACTGTTGGATGGCTCCCCAAAGAGATTCA

GAAGGCAGACTTCAGGCAGACCCTCAGCGCTTTCCTCATGGGATTCGCCAG

CTAGCTAATTATGTTCACAGCAAAGGACTGAAGCTAGGGATTTATGCAGAT

GTTGGAAATAAAACCTGCGCAGGCTTCCCTGGGAGTTTTGGATACTACGAC

ATTGATGCCCAGACCTTTGCTGACTGGGGAGTAGATCTGCTAAAATTTGAT

GGTTGTTACTGTGACAGTTTGGAAAATTTGGCAGATGGTTATAAGCACATG

TCCTTGGCCCTGAATAGGACTGGCAGAAGCATTGTGTACTCCTGTGAGTGG

CCTCTTTATATGTGGCCCTTTCAAAAGCCCAATTATACAGAAATCCGACAG

TACTGCAATCACTGGCGAAATTTTGCTGACATTGATGATTCCTGGAAAAGT

ATAAAGAGTATCTTGGACTGGACATCTTTTAACCAGGAGAGAATTGTTGAT

GTTGCTGGACCAGGGGGTTGGAATGACCCAGATATGTTAGTGATTGGCAAC

TTTGGCCTCAGCTGGAATCAGCAAGTAACTCAGATGGCCCTCTGGGCTATC

ATGGCTGCTCCTTTATTCATGTCTAATGACCTCCGACACATCAGCCCTCAA

GCCAAAGCTCTCCTTCAGGATAAGGACGTAATTGCCATCAATCAGGACCCC

TTGGGCAAGCAAGGGTACCAGCTTAGACAGGGAGACAACTTTGAAGTGTGG

GAACGACCTCTCTCAGGCTTAGCCTGGGCTGTAGCTATGATAAACCGGCAG

GAGATTGGTGGACCTCGCTCTTATACCATCGCAGTTGCTTCCCTGGGTAAA

GGAGTGGCCTGTAATCCTGCCTGCTTCATCACACAGCTCCTCCCTGTGAAA

AGGAAGCTAGGGTTCTATGAATGGACTTCAAGGTTAAGAAGTCACATAAAT

CCCACAGGCACTGTTTTGCTTCAGCTAGAAAATACAATGCAGATGTCATTA

AAAGACTTACTTTAA
```

In some aspects, a codon optimized nucleic acid molecule as herein described has a human codon adaptation index that is increased relative to that of the wild type GLA cDNA (GenBank Accession No. NM_000169.3; SEQ ID NO:3). In some embodiments, the codon optimized nucleic acid molecule has a human codon adaptation index of at least about 0.80, at least about 0.83, at least about 0.85, at least about 0.88, at least about 0.90, at least about 0.92 or at least about 0.93.

In certain embodiments, the nucleic acid contains a higher percentage of G/C nucleotides compared to the percentage of G/C nucleotides in SEQ ID NO:3. In other embodiments, the nucleic acid contains a percentage of G/C nucleotides that is at least about 49%, at least about 51%, at least about 53%, at least about 55%, at least about 57%, at least about 57.9% or is about 57.9%. In related embodiments, the nucleic acid contains a percentage of G/C nucleotides that is between about 49% and 60%, between about 50% and 59%, between about 55% and 59% or between about 57% and about 59%.

In other embodiments, the nucleic acid comprises one or more optimized parameters relative to SEQ ID NO:3: frequency of optimal codons; reduction in maximum length of direct repeat sequences; removal of restriction enzymes, removal of CIS-acting elements, and removal of destabilizing elements. In another embodiment, the nucleic acid is operatively linked to at least one transcription control sequence, preferably a transcription control sequence that is heterologous to the nucleic acid. In some aspects, the transcription control sequence is a cell- or tissue-specific promoter that results in cell-specific expression of the nucleic acid e.g. in cardiac or skeletal muscle cells. In other aspects, the transcription control sequence is a constitutive promoter that results in similar expression level of the nucleic acid in many cell types (e.g. a CAG, CBA (chicken beta actin) or CMV promoter). In preferred embodiments, the transcription control sequence comprises a CAG promoter comprising (i) the cytomegalovirus (CMV) early enhancer element, (ii) the promoter, first exon and first intron of chicken beta-actin gene and (iii) the splice acceptor of the rabbit beta-globin gene as described in Miyazaki et al., Gene 79(2):269-77 (1989). In a particularly preferred embodiment, the CAG promoter comprises the sequence of SEQ ID NO:5 or comprises a sequence at least 95%, at least 96%, at least 97%, at least 98% or at least 99% identical thereto.

(SEQ ID NO: 5)
ACTAGTTATTAATAGTAATCAATTACGGGGTCATTAGTTCATAGCCCATAT

ATGGAGTTCCGCGTTACATAACTTACGGTAAATGGCCCGCCTGGCTGACCG

CCCAACGACCCCCGCCCATTGACGTCAAAATGACGTATGTTCCCATAGTAA

CGCCAATAGGGACTTTCCATTGACGTCAATGGGTGGAGTATTTACGGTAAA

CTGCCCACTTGGCAGTACATCAAGTGTATCATATGCCAAGTACGCCCCCTA

TTGACGTCAATGACGGTAAATGGCCCGCCTGGCATTATGCCCAGTACATGA

CCTTATGGGACTTTCCTACTTGGCAGTACATCTACGTATTAGTCATCGCTA

TTACCATGGTCGAGGTGAGCCCCACGTTCTGCTTCACTCTCCCCATCTCCC

CCCCCTCCCCACCCCCAATTTTGTATTTATTTATTTTTTAATTATTTTGTG

CAGCGATGGGGCGGGGGGGGGGGGGGCGCGCGCCAGGCGGGGCGGGGC

GGGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGGC

GGCCCTATAAAAAGCGAAGCGCGCGGCGGGCGGGGAGTCGCTGCGACGCTG

CCTTCGCCCCGTGCCCCGCTCCGCCGCCGCCTCGCGCCGCCCGCCCCGGCT

CTGACTGACCGCGTTACTCCCACAGGTGAGCGGGCGGGACGGCCCTTCTCC

TCCGGGCTGTAATTAGCGCTTGGTTTAATGACGGCTTGTTTCTTTTCTGTG

GCTGCGTGAAAGCCTTGAGGGGCTCCGGGAGGGCCCTTTGTGCGGGGGGAG

CGGCTCGGGGGGTGCGTGCGTGTGTGTGTGCGTGGGGAGCGCCGCGTGCGG

CTCCGCGCTGCCCGGCGGCTGTGAGCGCTGCGGGCGCGGCGCGGGGCTTTG

TGCGCTCCGCAGTGTGCGCGAGGGGAGCGCGGCCGGGGGGCGGTGCCCCGCG

GTGCGGGGGGGGCTGCGAGGGGAACAAAGGCTGCGTGCGGGGTGTGTGCGT

-continued
GGGGGGGTGAGCAGGGGGTGTGGGCGCGTCGGTCGGGCTGCAACCCCCCCT

GCACCCCCCTCCCCGAGTTGCTGAGCACGGCCCGGCTTCGGGTGCGGGGCT

CCGTACGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGG

GGAGGGGCGCGGCGGCCCCCGGAGCGCCGGCGGCTGTCGAGGCGCGGCGAG

CCGCAGCCATTGCCTTTTATGGTAATCGTGCGAGAGGGCGCAGGGACTTCC

TTTGTCCCAAATCTGTGCGGAGCCGAAATCTGGGAGGCGCCGCCGCACCCC

CTCTAGCGGGCGCGGGGCGAAGCGGTGCGGCGCCGGCAGGAAGGAAATGGG

CGGGGAGGGCCTTCGTGCGTCGCCGCGCCGCCGTCCCCTTCTCCCTCTCCA

GCCTCGGGGCTGTCCGCGGGGGGACGGCTGCCTTCGGGGGGGACGGGGCAG

GGCGGGGTTCGGCTTCTGGCGTGTGACCGGCGGCTCTAGAGCCTCTGCTAA

CCATGTTCATGCCTTCTTCTTTTTCCTACAG

In related embodiments, provided herein is an expression cassette comprising a nucleic acid comprising the nucleotide sequence of SEQ ID NO:1, or a nucleotide sequence at least 90% identical thereto, operably linked to an expression control sequence.

In related embodiments, provided herein is a vector comprising a nucleic acid comprising the nucleotide sequence of SEQ ID NO:1, or a nucleotide sequence at least 90% or at least 95% identical thereto. In preferred embodiments, the vector is a recombinant adeno-associated (rAAV) expression vector. In some embodiments, the rAAV vector comprises a native capsid (e.g. a capsid of AAV serotype 1, AAV serotype 2, AAV serotype 6, or AAV serotype 8). In other embodiments, the rAAV vector comprises a capsid that is modified (e.g. comprises one or more peptide insertions and/or one or more amino acid substitutions (e.g. tyrosine to phenylalanine) and/or amino acid insertions or amino acid deletions) relative to a native AAV capsid (e.g. comprising one or more modifications relative to an AAV capsid of serotype 1, 2, 6 or 8). In a particularly preferred embodiment, the rAAV vector comprises a capsid comprising a capsid protein of SEQ ID NO:4 or a sequence at least 90%, at least 95% or at least 98% identical thereto.

In another embodiment, provided herein is a host cell comprising a nucleic acid comprising the nucleotide sequence of SEQ ID NO:1, or a nucleotide sequence at least 90% identical thereto. In some aspects, the host cell is a mammalian cell, including without limitation, a CHO cell, an HEK293 cell, and HEK293T cells, a HeLa cell, a BHK21 cell, a Vero cell or a V27 cell. In other aspects, the host cell is a cardiac or skeletal muscle cell (e.g. myoblast, skeletal muscle fibroblast, skeletal muscle satellite cell, cardiomyocyte, cardiac fibroblast, cardiac progenitor cell, smooth muscle cell endothelial and/or diaphragm muscle cell). In related embodiments, the disclosure provides a method of increasing expression of a polypeptide of SEQ ID NO: 2 comprising culturing the host cell under conditions whereby a polypeptide of SEQ ID NO: 2 is expressed by the nucleic acid molecule, wherein the expression of the polypeptide is increased relative to a host cell cultured under the same conditions comprising a reference nucleic acid comprising the nucleotide sequence of SEQ ID NO:3 (comparator sequence).

In another embodiment, the disclosure provides a method of increasing expression of a polypeptide of SEQ ID NO: 2 in a human subject comprising administering to the subject an isolated nucleic acid molecule comprising a nucleotide sequence at least 85%, at least 90%, at least 95%, at least 96%, at least 97%, at least 98%, or at least 99% identical to the nucleotide sequence of SEQ ID NO:1 and which encodes a polypeptide having the amino acid sequence of SEQ ID NO:2 or a vector comprising such a nucleotide sequence, wherein the expression of the polypeptide is increased relative to a reference nucleic acid molecule comprising the nucleotide sequence of SEQ ID NO:3 (comparator sequence) or a vector comprising the reference nucleic acid molecule.

In some embodiments, the disclosure provides a method of treating a disorder associated with insufficient GLA activity in a human subject comprising administering to the subject a nucleic acid molecule or a vector disclosed herein. In some embodiments, the disorder is Fabry disease.

DESCRIPTION OF THE DRAWINGS

FIG. 6A: Day 21 of differentiation of Fabry disease iPSC into endothelial cells yielded a population of 99.2% CD31 positive cells and 87.9% CD144 positive when examined by flow cytometry and gated using the IgG control. FIG. 6B: CD31 (green) expression by immunocytochemistry in cultures used in vector characterization. Cells were counterstained with DAPI (blue). Scale bar=100 μM.

FIG. 7A illustrates flow cytometric expression of AGA protein in live CD31$^+$/CD144$^+$ population at four days post-transduction in Fabry endothelial cells transduced with the rAAV. FIG. 7B: robust expression of AGA protein seen by western blot analysis of Fabry iPSC-derived endothelial cells after transduction with the rAAV. Band densitometry in histogram. AGA=alpha galactosidase, MOI=Multiplicity of infection, NT=non-transduced, Gb3=globotriaosylceramide, n=3, Error bars=Standard Deviation; ****$p<0.0001$, *$p<0.05$ compared to predecessor MOI, One-way ANOVA, Tukey post-hoc compared to NT.

FIG. 8A: AGA activity was quantified by AGA activity assay at day four post-transduction. Fabry iPSC-ECs transduced with the rAAV had more AGA activity than non-transduced Fabry endothelial cells. FIG. 8B: ICC of globotriaosylceramide (Gb3, pink) positive cells and nuclei counterstain with DAPI (blue). GLA=alpha galactosidase, MOI=Multiplicity of infection, NT=non-transduced, Gb3=globotriaosylceramide, n=3, Error bars Standard Deviation; *$p<0.05$ or **$p<0.001$ compared to preceding MOIs (500, 100, 50, & NT_from top to bottom), One-way ANOVA, Tukey post-hoc. 3 experimental and 3 technical replicates each.

FIG. 9A: AGA activity in wildtype and Fabry mouse plasma after a single intravenous dose. FIG. 9B: AGA activity in wild type and Fabry mouse tissues after a single intravenous dose. Mean±standard deviation; * p<0.01 compared to Vehicle-WT, #p<0.01 compared to Vehicle-KO. WT=wildtype mouse, KO=Fabry Disease mouse (knock-out).

FIG. 21A shows AGA activity in the left ventricle; FIG. 21B shows AGA activity in the ventricular septum.

DETAILED DESCRIPTION OF THE INVENTION

Definitions

Figure 1:
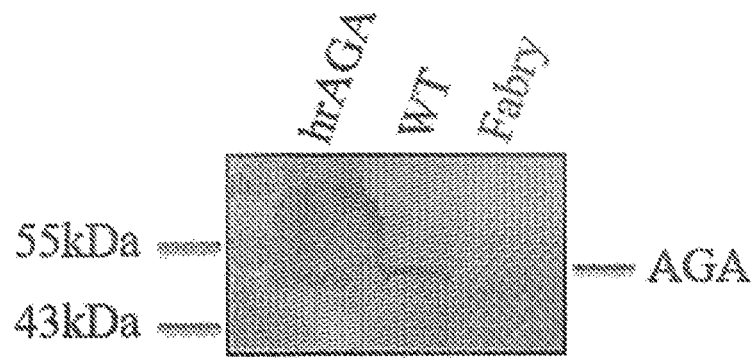
FIG. 1 AGA Protein Absent from Fabry Disease Fibroblasts. A Western blot analysis of wildtype and Fabry diseased fibroblasts is shown. Lysates of Fabry fibroblasts lacked AGA protein expression (49 kDa), an indication of their disease mutation (W162X). Samples were normalized for total protein and equally loaded on the gel. Standard protein ladder on the far left. hrAGA: human recombinant AGA, WT: wildtype, AGA: alpha galactosidase, kDa: kilodaltons.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L \sum_{l=1}^{L} \ln(w_1(l))\right), \quad (I)$$

For each amino acid, the weight of each of its codons, in CAI, is computed as the ratio between the observed frequency of the codon (fi) and the frequency of the synonymous codon (fj) for that amino acid:

$$w_i = \frac{f_i}{\max(f_i)} ij \in [\text{synonymous codons for amino acid}] \quad (II)$$

The term "isolated" designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region, or comprise two or more coding regions.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

As used herein, the term "nucleic acid" is interchangeable with "polynucleotide" or "nucleic acid molecule" and a polymer of nucleotides is intended.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit beta-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), p-galactosidase (LacZ), β-glucuronidase (Gus), and the like. Selectable markers can also be considered to be reporters.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

The term "4D-310" refers to a recombinant AAV virion comprising (i) a capsid comprising a capsid protein with the amino acid of SEQ ID NO:4 and (ii) a heterologous nucleic acid comprising the nucleotide sequence set forth as SEQ ID NO:6. The nucleotide sequence of SEQ ID NO:6 comprises the nucleotide sequence of SEQ ID NO:1 operably linked to a CAG promoter comprising the nucleotide sequence of SEQ ID NO:5.

The term "4D-C102" or "C102" refers to a variant AAV capsid protein comprising the amino acid sequence of SEQ ID NO:4.

The terms "GLA" and "AGA" are used herein interchangeably to refer to the gene encoding alpha-galactosidase and the encoded protein.

In one embodiment, the present invention provides a modified nucleic acid molecule comprising a nucleotide sequence that encodes a polypeptide of SEQ ID NO:2 (human AGA, consisting of 429 amino acids and available in GenBank Accession Nos. X14448.1 and U78027), wherein the nucleic acid sequence has been codon optimized. In another embodiment, the starting nucleic acid sequence that encodes a polypeptide of SEQ ID NO:2 and that is subject to codon optimization has the nucleotide sequence set forth as SEQ ID NO:3. In preferred embodiments, the sequence that encodes a polypeptide of SEQ ID NO:2 is codon optimized for human expression. SEQ ID NO:1 is a codon optimized version of SEQ ID NO:3, optimized for human expression:

```
                                          (SEQ ID NO: 1)
ATGCAGCTGCGGAATCCTGAACTGCACCTGGGATGTGCCCTGGCTCTGAGA

TTTCTGGCCCTGGTGTCTTGGGACATCCCTGGCGCTAGAGCCCTGGATAAT

GGCCTGGCCAGAACACCTACAATGGGCTGGCTGCACTGGGAGAGATTCATG

TGCAACCTGGACTGCCAAGAGGAACCCGACAGCTGCATCAGCGAGAAGCTG

TTCATGGAAATGGCCGAGCTGATGGTGTCCGAAGGCTGGAAGGATGCCGGC

TACGAGTACCTGTGCATCGACGACTGTTGGATGGCCCCTCAGAGAGACTCT

GAGGGCAGACTGCAAGCCGATCCTCAGAGATTCCCTCACGGCATCAGACAG

CTGGCCAACTACGTGCACAGCAAGGGCCTGAAGCTGGGCATCTATGCCGAC

GTGGGCAACAAGACCTGTGCCGGCTTTCCTGGCAGCTTCGGCTACTACGAT

ATCGACGCCCAGACCTTCGCCGATTGGGGAGTCGATCTGCTGAAGTTCGAC

GGCTGCTACTGCGACAGCCTGGAAAATCTGGCCGACGGCTACAAGCACATG

TCACTGGCCCTGAATCGGACCGGCAGATCCATCGTGTACAGCTGCGAGTGG

CCCCTGTACATGTGGCCCTTCCAGAAGCCTAACTACACCGAGATCAGACAG

TACTGCAACCACTGGCGGAACTTCGCCGACATCGACGATAGCTGGAAGTCC

ATCAAGAGCATCCTGGACTGGACCAGCTTCAATCAAGAGCGGATCGTGGAC

GTGGCAGGACCTGGCGGATGGAACGATCCTGACATGCTGGTCATCGGCAAC

TTCGGCCTGAGCTGGAACCAGCAAGTGACCCAGATGGCCCTGTGGGCCATT

ATGGCCGCTCCTCTGTTCATGAGCAACGACCTGAGACACATCAGCCCTCAG

GCCAAGGCTCTGCTCCAGGACAAGGATGTGATCGCTATCAACCAGGATCCT

CTGGGCAAGCAGGGCTACCAGCTGAGACAGGGCGACAATTTCGAAGTGTGG

GAAAGACCCCTGAGCGGACTGGCTTGGGCCGTCGCCATGATCAACAGACAA

GAGATCGGCGGACCCCGGTCCTACACAATTGCCGTGGCTTCTCTCGGCAAA
```

```
-continued
GGCGTGGCCTGTAATCCCGCCTGCTTTATCACACAGCTGCTGCCCGTGAAG

AGAAAGCTGGGCTTTTACGAGTGGACCAGCAGACTGCGGAGCCACATCAAT

CCTACCGGCACAGTGCTGCTGCAACTGGAAAACACAATGCAGATGAGCCTG

AAGGACCTGCTCTAA
```

The nucleotide sequence of SEQ ID NO:1 comprises a TAA stop codon. In alternative embodiments, a nucleotide sequence comprising the first 1287 nucleotides of SEQ ID NO:1 and ending with a different stop codon (e.g. TAG or TGA).

In one aspect, the disclosure provides a polynucleotide comprising the nucleotide sequence of SEQ ID NO:1 or polynucleotide comprising a nucleotide sequence at least 90%, at least 95%, at least 96%, at least 97%, at least 98%, or at least 99% identical to the nucleotide sequence of SEQ ID NO:1 and which encodes a human AGA polypeptide having the amino acid sequence of SEQ ID NO:2:

```
                                              (SEQ ID NO: 2)
MQLRNPELHLGCALALRFLALVSWDIPGARALDNGLARTPTMGWLHWERFM

CNLDCQEEPDSCISEKLFMEMAELMVSEGWKDAGYEYLCIDDCWMAPQRDS

EGRLQADPQRFPHGIRQLANYVHSKGLKLGIYADVGNKTCAGFPGSFGYYD

IDAQTFADWGVDLLKFDGCYCDSLENLADGYKHMSLALNRTGRSIVYSCEW

PLYMWPFQKPNYTEIRQYCNHWRNFADIDDSWKSIKSILDWTSFNQERIVD

VAGPGGWNDPDMLVIGNFGLSWNQQVTQMALWAIMAAPLFMSNDLRHISPQ

AKALLQDKDVIAINQDPLGKQGYQLRQGDNFEVWERPLSGLAWAVAMINRQ

EIGGPRSYTIAVASLGKGVACNPACFITQLLPVKRKLGFYEWTSRLRSHIN

PTGTVLLQLENTMQMSLKDLL
```

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

| The Standard Genetic Code | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC Cys (C) |
| | TTA Leu (L) | TCA Ser (S) | TAA Stop | TGA Stop |
| | TTG Leu (L) | TCG Ser (S) | TAG Stop | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Gln (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., el al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

Non-Viral Vectors

In some embodiments, a non-viral vector (e.g. an expression plasmid) comprising a modified nucleic acid as herein described is provided. Preferably, the non-viral vector is a plasmid comprising a nucleic acid sequence of SEQ ID NO: 1, or a sequence at least 90% identical thereto.

Viral Vectors

In preferred embodiments, a viral vector comprising a modified (codon optimized) nucleic acid as herein described is provided. Preferably, the viral vector comprises a nucleic acid sequence of SEQ ID NO: 1, or a sequence at least 90% identical thereto, operably linked to an expression control sequence. Examples of suitable viral vectors include but are not limited to adenoviral, retroviral, lentiviral, herpesvirus and adeno-associated virus (AAV) vectors.

In a preferred embodiment, the viral vector includes a portion of a parvovirus genome, such as an AAV genome with the rep and cap genes deleted and/or replaced by the modified GLA gene sequence and its associated expression control sequences. The modified human GLA gene sequence is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins. Other regulatory sequences suitable for use in facilitating tissue-specific expression of the modified GLA gene sequence in the target cell may also be included.

Those skilled in the art will appreciate that an AAV vector comprising a transgene and lacking virus proteins needed for viral replication (e.g., cap and rep), cannot replicate since such proteins are necessary for virus replication and packaging. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to Eland E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e., self complementary as described in WO 2001/92551).

The viral capsid component of the packaged viral vectors may be a parvovirus capsid. AAV Cap and chimeric capsids are preferred. For example, the viral capsid may be an AAV capsid (e.g., AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAVrh10, AAVrh74, RHM4-1, AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4.sup.th ed., Lippincott-Raven Publishers).

In some embodiments, the viral capsid component of the packaged viral vector is a variant of a native AAV capsid (i.e. comprises one or more modifications relative to a native AAV capsid). In some embodiments, the capsid is a variant of an AAV2, AAV5 or AAV8 capsid. In preferred embodiments, the capsid is a variant of an AAV2 capsid, such as those described in PCT Application No. US18/51812 (WIPO Publication Number WO 2019/060454 (e.g. comprising the amino acid sequence of any of SEQ ID NOs: 43-61), the contents of which are incorporated herein by reference. In a particularly preferred embodiment, the capsid comprises a capsid protein having the following amino acid sequence:

(SEQ ID NO: 4)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLANKTTNKDARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSINVDFTVDTNGVYSEPRPIGTRYLTRNL

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

In yet another embodiment the present invention provides for the use of ancestral AAV vectors for use in therapeutic in vivo gene therapy. Specifically, in silico-derived sequences were synthesized de novo and characterized for biological activities. This effort led to the generation of nine functional putative ancestral AAVs and the identification of Anc80, the predicted ancestor of AAV serotypes 1, 2, 8 and 9 (Zinn et al., 2015, Cell Reports 12:1056-1068). Predicting and synthesis of such ancestral sequences in addition to assembling into a virus particle may be accomplished by using the methods described in WO 2015/054653, the contents of which are incorporated by reference herein. Notably, the use of the virus particles assembled from ancestral viral sequences may exhibit reduced susceptibility to pre-existing immunity in current day human population than do contemporary viruses or portions thereof.

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than $10^5$ vector genome containing particles (vg)/cell or greater than $10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified GLA gene and CAG promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>1×10^13 vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous time-points post-transfection.

The packaging cells include viral vector functions, along with packaging and vector functions. The viral vector functions typically include a portion of a parvovirus genome, such as an AAV genome, with rep and cap deleted and replaced by the modified GLA sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

The terminal repeats (TR(s)) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03, and other novel capsids as yet unidentified or from non-human primate sources. Capsid components may include components from two or more AAV capsids.

The packaged viral vector generally includes the modified GLA gene sequence and expression control sequences flanked by TR elements, referred to herein as the "transgene" or "transgene expression cassette," sufficient to result in packaging of the vector DNA and subsequent expression of the modified GLA gene sequence in the transduced cell. The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm el al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, W138, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359. In another aspect, the packaging cell is cultured in the form of a cell stack (e.g. 10-layer cell stack seeded with HEK293 cells).

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provides for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculovirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein. These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA.

The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443: U.S. Pat. No. 6,566,118 and WO 98/09657.

Treatment Methods

In certain embodiments, a method is provided for the treatment of Fabry disease in a subject in need of such treatment by administering to the subject a therapeutically effective amount of a nucleic acid having a nucleotide sequence at least 90%, at least 95%, at least 98% identical, or 100% identical to the nucleotide sequence of SEQ ID NO: 1 or a pharmaceutical composition comprising such a nucleic acid and at least one pharmaceutically acceptable excipient. In some aspects, a nucleic acid having a nucleotide sequence at least 90% identical to SEQ ID NO:1 is administered to a subject in an amount effective to reduce the level of globotriaosylceramide (Gb3) in the subject.

In related aspects, a nucleic acid comprising a nucleotide sequence at least 90%, at least 95%, at least 98% identical, or 100% identical to the nucleotide sequence of SEQ ID NO:1 for use in the treatment of Fabry disease is provided.

In other related aspects, the use of a nucleic acid comprising a nucleotide sequence at least 90%, at least 95%, at least 98% identical, or 100% identical to the nucleotide sequence of SEQ ID NO: 1 for the manufacture of a medicament is provided.

In other related aspects, the use of a nucleic acid comprising a nucleotide sequence at least 90%, at least 95%, at least 98% identical, or 100% identical to the nucleotide sequence of SEQ ID NO:1 for the manufacture of a medicament for the treatment of Fabry disease is provided.

In some aspects, the nucleotide sequence at least 90%, at least 95%, at least 98% identical, or 100% identical to the nucleotide sequence of SEQ ID NO:1 is operably linked to an expression control sequence.

In preferred embodiments, a method for treating Fabry disease is provided comprising administering to a subject in need thereof a therapeutically effective amount of a nucleic acid comprising the nucleotide sequence of SEQ ID NO:1 operably linked to a CAG promoter or by administering to the subject a pharmaceutical composition comprising such a nucleic acid.

In other embodiments, a nucleic acid comprising the nucleotide sequence of SEQ ID NO:1 operably linked to a CAG promoter for use in the treatment of Fabry disease is provided. In some aspects, the CAG promoter comprises a sequence that is at least 90%, at least 95%, or at least 98% identical, or is 100% identical to the nucleotide sequence of SEQ ID NO:5.

In other embodiments, the use of a nucleic acid comprising the nucleotide sequence of SEQ ID NO: 1 operably linked to a CAG promoter for the manufacture of a medicament for the treatment of Fabry disease is provided.

In related aspects, a recombinant AAV (rAAV) virion comprising (i) a nucleic acid having a nucleotide sequence at least 90%, at least 95%, at least 98% identical, or 100% identical to the nucleotide sequence of SEQ ID NO:1 operably linked to an expression control sequence and (ii) a native or variant AAV capsid or a pharmaceutical composition comprising such an rAAV for use in the treatment of Fabry disease, or for use in the manufacture of a medicament for the treatment of Fabry disease, is provided.

In some embodiments, the rAAV virion comprises a native AAV1, AAV2, AAV6 or AAV8 capsid. In other embodiments, the rAAV virion comprises a variant AAV capsid that comprises one or more modifications relative to AAV1, AAV2, AAV6, or AAV8. In a preferred embodiment, the AAV capsid comprises the sequence of SEQ ID NO:4 or a sequence at least 95%, at least 98% or at least 99% identical thereto.

In a preferred embodiment, the use of an rAAV in the treatment of Fabry disease or for the manufacture of a medicament for the treatment of Fabry disease is provided, wherein the rAAV comprises (i) a nucleic acid comprising a nucleotide sequence of SEQ ID NO:1 operably linked to a CAG promoter and (ii) a capsid comprising a capsid protein having the amino acid sequence of SEQ ID NO:4. In particularly preferred embodiments, the rAAV comprises (i) a nucleic acid comprising a nucleotide sequence of SEQ ID NO:6 and (ii) a capsid comprising a capsid protein having the amino acid sequence of SEQ ID NO:4. In some aspects, the rAAV is administered by intramuscular and/or intravascular (e.g. intravenous) injection. In a particularly preferred embodiment, the rAAV is administered as a single intravenous administration.

In other aspects, a pharmaceutical composition is provided comprising a nucleic acid having a nucleotide sequence at least 90%, at least 95%, at least 98% identical, or 100% identical to the nucleotide sequence of SEQ ID NO:1, optionally operably linked to an expression control sequence, and at least one pharmaceutically acceptable excipient. In some embodiments, the pharmaceutical composition comprises a nucleic acid comprising the nucleotide sequence of SEQ ID NO:1 operably linked to a CAG promoter. In some embodiments, the CAG promoter comprises a sequence at least 90%, at least 95%, or at least 98% identical to SEQ ID NO:5 or is identical to SEQ ID NO:5.

In other aspects, a pharmaceutical composition is provided comprising at least one pharmaceutically acceptable excipient and an infectious rAAV comprising (i) a nucleic acid comprising a nucleotide sequence of SEQ ID NO:1 operably linked to a CAG promoter and (ii) a capsid comprising a capsid protein having the amino acid sequence of SEQ ID NO:4. In related aspects, the infectious rAAV comprises (i) a capsid comprising a capsid protein having the amino acid sequence of SEQ ID NO:4 and (ii) a nucleic acid comprising from 5' to 3': (a) an AAV2 terminal repeat (b) a CAG promoter (c) a nucleic acid according to claim 3 (d) a polyadenylation sequence and (e) an AAV2 terminal repeat. In a particularly preferred embodiment, the infectious rAAV comprises (i) a capsid comprising a capsid protein having the amino acid sequence of SEQ ID NO:4 and (ii) a nucleic acid comprising the sequence of SEQ ID NO:6 or a sequence at least 90%, at least 95%, at least 98% or at least 99% identical thereto:

(SEQ ID NO: 6)
```
TTGGCCACTCCCTCTCTGCGCGCTCGCTCGCTCACTGAGGCCGGGCGACCAA

AGGTCGCCCGACGCCCGGGCTTTGCCCGGGCGGCCTCAGTGAGCGAGCGAG

CGCGCAGAGAGGGAGTGGCCAACTCCATCACTAGGGGTTCCTATCGATTGAA

TTCCCCGGGGATCCACTAGTTATTAATAGTAATCAATTACGGGGTCATTAGTT

CATAGCCCATATATGGAGTTCCGCGTTACATAACTTACGGTAAATGGCCCGC

CTGGCTGACCGCCCAACGACCCCCGCCCATTGACGTCAATAATGACGTATGT

TCCCATAGTAACGCCAATAGGGACTTTCCATTGACGTCAATGGGTGGAGTAT

TTACGGTAAACTGCCCACTTGGCAGTACATCAAGTGTATCATATGCCAAGTA

CGCCCCCTATTGACGTCAATGACGGTAAATGGCCCGCCTGGCATTATGCCCA

GTACATGACCTTATGGGACTTTCCTACTTGGCAGTACATCTACGTATTAGTCA

TCGCTATTACCATGGTCGAGGTGAGCCCCACGTTCTGCTTCACTCTCCCCATC

TCCCCCCCCTCCCCACCCCCAATTTTGTATTTATTTATTTTTAATTATTTTGT

GCAGCGATGGGGGCGGGGGGGGGGGGGGCGCGCGCCAGGCGGGGCGGG

GCGGGGCGAGGGGCGGGCGGGGCGAGGCGGAGAGGTGCGGCGGCAGCCA
```

-continued

```
ATCAGAGCGGCGCGCTCCGAAAGTTTCCTTTTATGGCGAGGCGGCGGCGGCG
GCGGCCCTATAAAAAGCGAAGCGCGCGGCGGGCGGGGAGTCGCTGCGACGC
TGCCTTCGCCCCGTGCCCCGCTCCGCCGCCGCCTCGCGCCGCCCGCCCCGGCT
CTGACTGACCGCGTTACTCCCACAGGTGAGCGGGCGGGACGCCCTTCTCCT
CCGGGCTGTAATTAGCGCTTGGTTTAATGACGGCTTGTTTCTTTTCTGTGGCT
GCGTGAAAGCCTTGAGGGGCTCCGGGAGGGCCCTTTGTGCOGGGGGAGCGG
CTCGGGGGGTGCGTGCGTGTGTGTGCGTGGGGAGCGCCGCGTGCGGCTCC
GCGCTGCCCGGCGGCTGTGAGCGCTGCGGGCGCGGCGCGGGGCTTTGTGCGC
TCCGCAGTGTGCGCGAGGGGAGCGCGGCCGGGGGCGGTGCCCCGCGGTGCG
GGGGGGGCTGCGAGGGGAACAAAGGCTGCGTGCGGGGTGTGTGCGTGGGGG
GGTGAGCAGGGGGTGTGGGCGCGTCGGTCGGGCTGCAACCCCCCCTGCACCC
CCCTCCCCGAGTTCCTGAGCACGGCCCGGCTTCGGGTGCGGGGCTCCGTACG
GGGCGTGGCGCGGGGCTCGCCGTGCCGGGCGGGGGGTGGCGGCAGGTGGGG
GTGCCGGGCGGGGCGGGGCCGCCTCGGGCCGGGGAGGGCTCGGGGGAGGGG
CGCGGCGGCCCCCGGAGCGCCGGCGGCTGTCGAGGCGCGGCGAGCCGCAGC
CATTGCCTTTTATGGTAATCGTGCGAGAGGGCGCAGGGACTTCCTTTGTCCCA
AATCTGTGCGGAGCCGAAATCTGGGAGGCGCCGCCGCACCCCCTCTAGCGGG
CGCGGGGCGAAGCGGTGCGGCGCCGGCAGGAAGGAAATGGGCGGGGAGGG
CCTTCGTGCGTCGCCGCGCCGCCGTCCCCTTCTCCCTCTCCAGCCTCGGGGCT
GTCCGCGGGGGACGGCTGCCTTCGGGGGGGACGGGGCAGGGCGGGGTTCG
GCTTCTGGCGTGTGACCGGCGGCTCTAGAGCCTCTGCTAACCATGTTCATGCC
TTCTTCTTTTTCCTACAGTCTAGAGTCGACCTGCAGGTGGATATCTTGCTAGC
ACGCCACCATGCAGCTGCGGAATCCTGAACTGCACCTGGGATGTGCCCTGGC
TCTGAGATTTCTGGCCCTGGTGTCTTGGGACATCCCTGGCGCTAGAGCCCTGG
ATAATGGCCTGGCCAGAACACCTACAATGGGCTGGCTGCACTGGGAGAGATT
CATGTGCAACCTGGACTGCCAAGAGGAACCCGACAGCTGCATCAGCGAGAA
GCTGTTCATGGAAATGGCCGAGCTGATGGTGTCCGAAGGCTGGAAGGATGCC
GGCTACGAGTACCTGTGCATCGACGACTGTTGGATGGCCCCTCAGAGAGACT
CTGAGGGCAGACTGCAAGCCGATCCTCAGAGATTCCCTCACGGCATCAGACA
GCTGGCCAACTACGTGCACAGCAAGGGCCTGAAGCTGGGCATCTATGCCGAC
GTGGGCAACAAGACCTGTGCCGGCTTTCCTGGCAGCTTCGGCTACTACGATA
TCGACGCCCAGACCTTCGCCGATTGGGGAGTCGATCTGCTGAAGTTCGACGG
CTGCTACTGCGACAGCCTGGAAAATCTGGCCGACGGCTACAAGCACATGTCA
CTGGCCCTGAATCGGACCGGCAGATCCATCGTGTACAGCTGCGAGTGGCCCC
TGTACATGTGGCCCTTCCAGAAGCCTAACTACACCGAGATCAGACAGTACTG
CAACCACTGGCGGAACTTCGCCGACATCGACGATAGCTGGAAGTCCATCAAG
AGCATCCTGGACTGGACCAGCTTCAATCAAGAGCGGATCGTGGACGTGGCA
GGACCTGGCGGATGGAACGATCCTGACATGCTGGTCATCOGCAACTTCGGCC
TGAGCTGGAACCAGCAAGTGACCCAGATGGCCCTGTGGGCCATTATGGCCGC
TCCTCTGTTCATGAGCAACGACCTGAGACACATCAGCCCTCAGGCCAAGGCT
CTGCTCCAGGACAAGGATGTGATCGCTATCAACCAGGATCCTCTGGGCAAGC
```

-continued

```
AGGGCTACCAGCTGAGACAGGGCGACAATTTCGAAGTGTGGGAAAGACCCC

TGAGCGGACTGGCTTGGGCCGTCGCCATGATCAACAGACAAGAGATCGGCG

GACCCCGGTCCTACACAATTGCCGTGGCTTCTCTCGGCAAAGCCGTGGCCTG

TAATCCCGCCTGCTTTATCACACAGCTGCTGCCCGTGAAGAGAAAGCTGGGC

TTTTACGAGTGGACCAGCAGACTGCGGAGCCACATCAATCCTACCGGCACAG

TGCTGCTGCAACTGGAAAACACAATGCAGATGAGCCTGAAGGACCTGCTCTA

AGCCACGCGTAACACGTGCATGCGAGAGATCTGCGGCCGCGAGCTCGGGGA

TCCAGACATGATAAGATACATTGATGAGTTTGGACAAACCACAACTAGAATG

CAGTGAAAAAAATGCTTTATTTGTGAAATTTGTGATGCTATTGCTTTATTTGT

AACCATTATAAGCTGCAATAAACAAGTTAACAACAACAATTGCATTCATTTT

ATGTTTCAGGTTCAGGGGGAGGTGTGGGAGGTTTTTTAAAGCAAGTAAAACC

TCTACAAATGTGGTATGGCTGATTATGATCAATGCATCCTAGCCGGAGGAAC

CCCTAGTGATGGAGTTGGCCACTCCCTCTCTGCGCGCTCGCTCGCTCACTGAG

GCCGCCCGGGCAAAGCCCGGGCGTCGGGCGACCTTTGGTCGCCCGGCCTCAG

TGAGCGAGCGAGCGCGCAGAGAGGGAGTGGCCAA
```

In some preferred embodiments, a human subject with Fabry disease is administered a pharmaceutical composition comprising a pharmaceutically acceptable carrier and an rAAV vector comprising (i) a capsid comprising a capsid protein comprising or consisting of the amino acid sequence set forth as SEQ ID NO:4 and (ii) a heterologous nucleic acid comprising the sequence of SEQ ID NO:6, wherein the subject is administered one or more doses of the rAAV vector, each dose comprising from about $1 \times 10^{12}$ to about $1 \times 10^{15}$ vector particles/kg or vector genomes/kg, $1 \times 10^{12}$ to $1 \times 10^{15}$ vector particles or vector genomes, or about $1 \times 10^{12}$, about $2 \times 10^{12}$, $3 \times 10^{12}$, about $4 \times 10^{12}$, about $5 \times 10^{12}$, about $6 \times 10^{12}$, about $7 \times 10^{12}$, about $8 \times 10^{12}$, about $9 \times 10^{12}$, about $1 \times 10^{13}$, about $2 \times 10^{13}$, about $3 \times 10^{13}$, about $4 \times 10^{13}$, about $5 \times 10^{13}$, about $6 \times 10^{13}$, about $7 \times 10^{13}$, about $8 \times 10^{13}$, about $9 \times 10^{13}$, about $1 \times 10^{14}$, about $2 \times 10^{14}$, about $3 \times 10^{14}$, about $4 \times 10^{14}$, about $5 \times 10^{14}$, about $6 \times 10^{14}$, about $7 \times 10^{14}$, about $8 \times 10^{14}$ or about $1 \times 10^{15}$ vector particles/kg or vector genomes/kg. In some particularly preferred aspects, the subject is administered one or more doses of the rAAV, each dose comprising from about $1 \times 10^{12}$ vg/kg to $1 \times 10^{14}$ vg/kg, e.g. about $3 \times 10^{12}$, about $1 \times 10^{13}$, $3 \times 10^{13}$, or about $5 \times 10^{13}$ vector particles/kg or vector genomes/kg. In some particularly preferred embodiments, the pharmaceutical composition is administered to a human with Fabry disease via a single intravenous injection, wherein the single intravenous injection is effective to treat Fabry disease in the human subject. In other embodiments, the pharmaceutical composition is administered to a human with Fabry disease via a single intramuscular injection.

In some preferred embodiments, a pharmaceutical composition is provided, the pharmaceutical composition comprising a pharmaceutically acceptable carrier and an rAAV vector comprising (i) a capsid comprising a capsid protein comprising or consisting of the amino acid sequence set forth as SEQ ID NO:4 and (ii) a heterologous nucleic acid comprising the sequence of SEQ ID NO:6, wherein the pharmaceutical composition comprises $1 \times 10^{10}$ to $1 \times 10^{17}$ vector particles or vector genomes, $1 \times 10^{13}$ to $1 \times 10^{16}$ vector particles or vector genomes, or about $1 \times 10^{13}$, about $2 \times 10^{13}$, $3 \times 10^{13}$, about $4 \times 10^{13}$, about $5 \times 10^{13}$, about $6 \times 10^{14}$, about $7 \times 10^{13}$, about $8 \times 10^{13}$, about $9 \times 10^{13}$, about $1 \times 10^{14}$, about $2 \times 10^{14}$, about $3 \times 10^{14}$, about $4 \times 10^{14}$, about $5 \times 10^{14}$, about $6 \times 10^{14}$, about $7 \times 10^{14}$, about $8 \times 10^{14}$, about $9 \times 10^{14}$, about $1 \times 10^{15}$, about $2 \times 10^{15}$, about $3 \times 10^{15}$, about $4 \times 10^{15}$, about $5 \times 10^{15}$, about $6 \times 10^{15}$, about $7 \times 10^{15}$, about $8 \times 10^{15}$, about $9 \times 10^{15}$, about $1 \times 10^{16}$, about $5 \times 10^{16}$ or about $8 \times 10^{16}$ vector particles or vector genomes.

EXAMPLES

The following examples illustrate preferred embodiments of the present invention and are not intended to limit the scope of the invention in any way. While this invention has been described in relation to its preferred embodiments, various modifications thereof will be apparent to one skilled in the art from reading this application.

Example 1—Codon Optimization of GLA cDNA Sequence

The human GLA open reading frame cDNA sequence, including the endogenous GLA secretion signal (GenBank Accession No. NM_000169.3; SEQ ID NO:3) was codon optimized for human expression. The optimization algorithm included parameters including, but not limited to, codon usage bias, GC content, CpG dinucleotides content, negative CpG islands, mRNA secondary structure, RNA instability motifs, cryptic splicing sites, premature polyadenylation sites, internal chi sites and ribosomal binding sites, and repeat sequences.

The codon usage bias in humans was changed by upgrading the codon adaptation index (CAI) from 0.75 to 0.93. The average GC content was optimized from 48.6% in the native sequence to 57.9% in the optimized sequence to prolong the half-life of the mRNA. Stem-Loop structures, which impact ribosomal binding and stability of mRNA, were broken in the optimized sequence. In addition, negative cis-acting sites were screened and deleted to optimize expression of the gene in human cells and several restriction enzyme sites were deleted.

The resulting codon optimized nucleotide sequence, set forth herein as SEQ ID NO:1, contains improved codon usage, altered GC content, better mRNA stability, and modification of negative cis acting elements.

Example 2—Codon Optimized GLA cDNA Sequence is Expressed at Higher Levels in Cardiomyocytes from Patients with Fabry Disease A human in vitro model system was generated to evaluate expression of human GLA nucleic acid having the nucleotide sequence of SEQ ID NO: 1 in diseased human cardiomyocytes derived from a human Fabry disease patient and functional correction of the disease phenotype.

Materials and Methods

Fibroblast Cell Culture and Reprogramming to Induced Pluripotent Stem Cell Lines Non-diseased fibroblasts or male human Fabry disease fibroblasts were obtained from Coriell Institute and cultured in Eagle's Modified Essential Medium (EMEM) with 15% Fetal Bovine Serum (FBS, Hyclone) and 1% Penicillin/Streptomycin (ThermoFisher). For reprogramming, cells were passaged using 0.05% trypsin and plated at a density of $2.5 \times 10^4$ cells per $cm^2$ in 6 well tissue culture plates. Cells were kept at 37° C., 5% $CO_2$ in normoxic conditions.

Cellular reprogramming of diseased fibroblasts was performed by a single RNA transfection of Oct4-Klf4-Sox2-Glis1 polycistronic transcript according to the manufacturer's instructions (Simplicon RNA Reprogramming Kit, EMD Millipore). At day 10, approximately $5 \times 10^4$-$1 \times 10^5$ reprogrammed cells were re-plated on growth factor reduced Matrigel (Corning) in mouse embryonic fibroblasts (MEF)-conditioned medium containing B18R protein (200 ng/mL) supplemented with human iPSC Reprogramming Boost Supplement II (EMD Millipore). At day 20, reprogrammed cells, recognized by altered morphology and ability to form small colonies, were transitioned to mTeSR-1 media (Stem Cell Technologies). Colonies of approximately 200 cells or larger were isolated manually and plated on Matrigel coated plates in mTeSR-1 medium. Fabry-iPSC lines were expanded from a single colony. The Fabry-iPSC lines were cultured on Matrigel in mTeSR-1 maintenance medium and sub-cultured using Gentle Cell Dissociation Reagent (Stem Cell Technologies), every 4-5 days at 70-80% confluence. To ensure random differentiation into all three germ layers, iPSC embryoid bodies (EBs) were formed in suspension culture for one week and then differentiated in adherent conditions for an additional four weeks in 20% knockout serum replacement in DMEM containing 1× GlutaMax, 1× non-essential amino acids, with 1.4 μL/100 mL media of beta-mercaptoethanol (Thermo Fisher Scientific). iPSC clones used in cardiac differentiation were submitted to Cell Line Genetics for standard karyotyping, according to company protocols.

Fabry Diseased iPSC Cardiomyocyte Differentiation

Fabry iPSCs were seeded at 25,000 cells/$cm^2$ in mTeSR-1 in 3 twelve well plates coated with growth factor reduced Matrigel (GFR Matrigel, Corning). Upon reaching the confluency, cultures were subjected to sequential GSK3β and Porcupine inhibition of the Wnt pathway in RMPI 1640 with B27 supplement without insulin (RB−, ThermoFisher). On day 6 cells were fed with RMPI 1640 plus B27 supplement (RB+, ThermoFisher). Fabry diseased cardiomyocytes that exhibited visible beating by day 15 were passaged at 1:2 ratio into twelve well plates coated with GFR Matrigel in RB+. Following passage, Fabry cardiomyocytes were purified through glucose deprivation following a previously published differentiation paradigm (Lian et al., PNAS, 109 (27):E1848-57). Initial beating appeared 7 days after passage. After two weeks post purification, Fabry diseased cardiomyocytes were used for cell characterization and transduction with recombinant AAV (rAAV) particles comprising (i) a capsid with a capsid protein of SEQ ID NO:4 and (ii) a nucleic acid comprising a nucleotide sequence of SEQ ID NO: 1 operably linked to a CAG promoter of SEQ ID NO:5.

Fabry Diseased iPSC Cardiomyocyte Transduction

Cardiomyocytes were transduced 14 days after passage into experimental plates with the rAAV. On the day of transduction three wells were harvested to obtain a cell count. Cells were transduced at Multiplicity of Infections (MOI) of 25, 100, 250, based on the cell count and viral titer. Vehicle was added in the highest volume. Cells were incubated with virus for 48 hours and then received a media change. The media was changed every day other day until harvest, six days post transduction.

Immunocytochemistry (ICC)

IPSC and Germ Layer ICC iPSCs or 30-day old plated EBs were washed once with Phosphate Buffered Saline without Magnesium or Calcium (PBS−/−) and fixed with 4% paraformaldehyde for 15 minutes at room temperature. Cells were then washed 3 times with PBS−/− and blocked for 30 minutes with 2% bovine serum albumin and 5% goat serum in 0.2% Triton X-100 in PBS−/−. Nanog, Oct-4, Sox-2 or β-tubulin II, HNF-α and α-SMA primary antibodies were incubated at room temperature for 2 hours followed by a goat anti-mouse or goat anti-rabbit AlexaFluor (ThermoFisher) secondary antibodies for 1 hour at room temperature. Cells were counterstained with DAPI to visualize the nuclei and were imaged on a Zeiss Axiovert.A1 inverted microscope.

Cardiomyocyte ICC

Six days post infection, cells were washed once with PBS−/− and fixed with 4% paraformaldehyde for 15 minutes at room temperature. Cells were then washed 3 times with PBS−/− and blocked for 30 minutes with 2% bovine serum albumin and 5% goat serum in 0.2% Triton X-100 in PBS−/−. Primary antibodies against alpha galactosidase A (Abnova) and cardiac troponin T (cTNT, R&D) were incubated with cells in blocking solution for 2 hours at room temperature followed by a goat anti-mouse AlexaFluor-555 (ThermoFisher) secondary antibody for 1 hour at room temperature. Additionally, conjugated CD77 (Gb3)-AlexaFluor647 (BD) was incubated with fixed cells in blocking buffer for one hour. Cells were washed 3 times and counterstained with DAPI or Hoechst 33342 to visualize the nuclei and were imaged on a Zeiss Axiovert.A1 inverted microscope.

Western Blot

Six days post infection, cells were lifted with 0.05% trypsin and pelleted at 300×g for 5 minutes. Lysates were made using RIPA buffer plus protease inhibitors. Lysates were incubated on ice for 15 minutes and centrifuged at 21,000×g for 15 minutes. Supernatants were collected, and a bicinchoninic acid assay (BCA) was run to determine protein concentration. Concentrations were normalized and gels were equally loaded. An SDS-PAGE was run using a 4-12% polyacrylamide gel at 200 volts for 30 minutes. Protein was transferred to a 0.2 μm nitrocellulose membrane and probed with anti-alpha galactosidase A (Atlas) anti-GAPDH (Stem Cell Technologies) antibodies followed by species specific horseradish peroxidase secondary antibodies overnight. Enhanced chemiluminescence substrate was used to develop protein bands, and band detection was captured on a BioRad ChemiDoc MP.

AGA Activity Assay

Figure 2A:
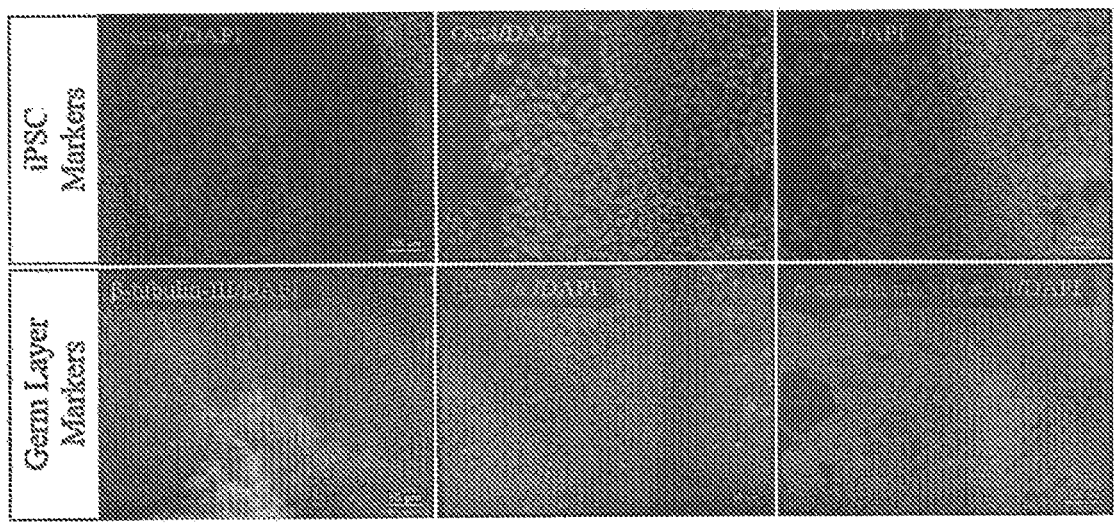
FIG. 2A-B Fabry Diseased Induced Pluripotent Stem Cell Characterization. Fabry diseased fibroblasts reprogrammed into induced pluripotent stem cells (iPSC) (FIG. 2A) express critical pluripotent transcription factors, Nanog (left, red), Oct 4 (middle, green) and Sox2 (right, red), DAPI (nuclei, blue) (top panel). Fabry iPSC differentiated into all three germ layers, ectoderm, endoderm and mesoderm and expressed lineage markers corresponding to each germ layer, ß-tubulin III (left, green), HNF-α (middle, red) and α-smooth muscle actin (left, red), respectively; DAPI (nuclei, blue) (bottom panel). Scale bar=100 μm. HNF4a: hepatocyte nuclear factor 4 alpha. Karyotype analysis of Fabry iPSC shows normal human male banding and chromosomal arrangement (FIG. 2B).
Figure 2B:
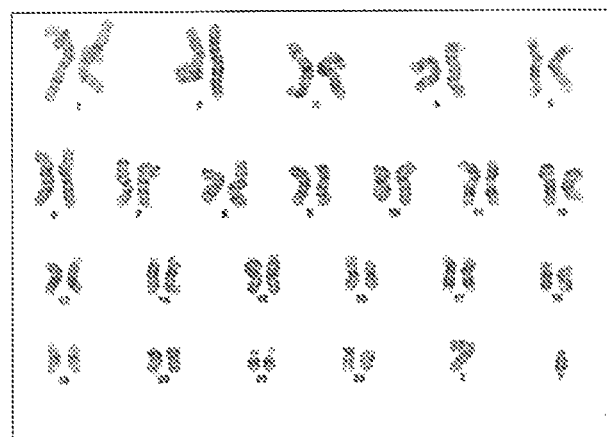

The AGA activity assay was performed with an alpha-galactosidase synthetic fluorometric substrate (BioVision, K407). AGA activity assay was performed according to the manufacturer's protocol with the following changes. Cells were dissociated using 0.25% trypsin and centrifuged at 300×g for 3 minutes. Cells were lysed with alpha-galactosidase buffer and incubated on ice for 10 minutes. Samples were centrifuged at 12,000×g for 10 minutes at 4° C. and supernatant was stored at −80° C. The following day, samples were thawed on ice and protein quantification via BCA assay was performed to allow for protein concentration normalization during analysis. The AGA activity assay reaction was incubated for 1 hour at room temperature and stopped using appropriate volume stop buffer. AGA activity assay reaction was immediately read on a Cytation3 plate reader (BioTek) at 360 excitation/445 emission with a gain set to highest concentration of AGA standard curve.

a pluripotent factor containing RNA replicon and cultured according to the manufacturer's instructions until small stem cell colonies appeared. Induced pluripotent stem cells (iPSC) colonies were clonally expanded and characterized for pluripotent transcription factor expression. The reprogrammed Fabry iPSC colonies showed positive expression and proper localization of three critical pluripotent transcription factors, Nanog, Oct4 and Sox2 (FIG. 2A, top panel). In addition to expressing pluripotent proteins, iPSCs must be able to differentiate into each germ layer. Following spontaneous differentiation of embryoid bodies formed from Fabry iPSCs, all three germ layers were detected, ectoderm by 3-tubulin III, endoderm by HNF-α and mesoderm by α-smooth muscle actin. To ensure the Fabry iPSCs did not contain chromosomal abnormalities, which can occur during reprogramming, karyotype analysis was done. No aberrations were detected (FIG. 2B).

Characterization of Fabry Diseased Induced Pluripotent Stem Cell Derived Cardiomyocytes Fabry iPSCs were differentiated into cardiomyocytes to develop a model of Fabry disease in a clinically relevant cell

TABLE 2

List of Antibodies

| Antibody | Host | Company-Catalog No. | Dilution |
|---|---|---|---|
| Primary Antibodies | | | |
| SOX2 | Rabbit | Abcam-ab92494 | 1:50 |
| OCT4 | Mouse | Millipore-MAB4401 | 1:50 |
| Nanog | Rabbit | Abeam-ab21624 | 1:50 |
| Alpha smooth muscle actin (aSMA) | Mouse | Sigma Aldrich-A2547 | 1:500 |
| Betn-Tubulin III | Mouse | Sigma-T8578 | 1:200 |
| HNF4-α | Rabbit | Santa Cruz-SC-8987 | 1:100 |
| Cardiac Troponin T (cTNT)-ICC | Mouse | R&D, MAB1874 | 1:100 |
| Cardiac Troponin T (cTNT)-Flow Cytometry | Mouse | BD Biosciences-565744 | 1:50 |
| Alpha Galactosidase A-ICC | Mouse | Abnova-H00002717-B01P | 1:100 |
| Alpha Galactosidase A-Western | Rabbit | Atlas-HPA000237 | 1:200 |
| Alpha Galactosidase A-PE-Flow | Rabbit | Abnova-A1VMRPSAM001664 | 1:100 |
| GAPDB | Rabbit | Stem Cell Technologies-5174 | 1:5000 |
| Globotriaosylceramide-FITC (Gb3)-ICC | Mouse | BD-551353 | 1:50 |
| Secondary Antibodies | | | |
| Hoechst 33342 Solution | NA | Thermo-62248 | 1:10000 |
| Alexa Fluor555 anti-rabbit | Goat | Invitrogen-A21428 | 1:500 |
| Alexa Fluor647 anti-rabbit | Ooat | Invitrogen-A-21244 | 1:500 |
| Alexa Fluor488 anti-rabbit | Goat | Invitrogen-A11078 | 1:500 |
| Alexa Fluor555 anti-mouse | Gnat | Invitrogen-A21422 | 1:500 |
| Alexa Fluor647 anti-mouse | Goat | Invitrogen-A-21235 | 1:500 |
| Alexa Fluor488 anti-mouse | Goat | Invitrogen-A11029 | 1:500 |
| Horseradish Peroxidase anti-Rabbit IgG (H + L) | Goat | Thermo-31460 | 1:5000 |

Results and Discussion

Derivation and Characterization of Fabry Diseased Induced Pluripotent Stem Cells Fabry patient fibroblast were obtained from Coriell Institute, with a mutation in the GLA gene (W162X, a well-described pathogenic mutation that typically results in absent AGA protein activity). Prior to reprogramming, AGA protein levels were detected via Western blot to confirm disease phenotype. A normal fibroblast line and a recombinant human AGA protein were used as positive controls for AGA protein levels. Fabry diseased fibroblasts exhibited a lack of AGA protein compared to wildtype (WT) fibroblasts (FIG. 1). Following confirmation of this disease characteristic, reprogramming was initiated.

Figure 3A:
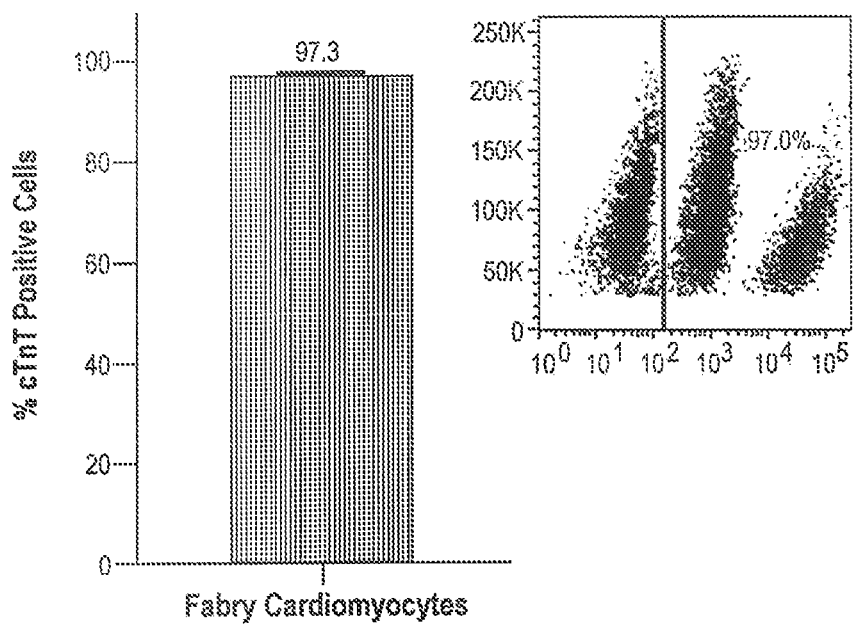
FIGS. 3A-B Fabry Diseased Induced Pluripotent Stem Cell Derived Cardiomyocyte Characterization. The differentiation of Fabry diseased iPSC into cardiomyocytes, yielded a population of 97% cTNT positive cells when examined by flow cytometry and gated using the IgG control. Scatter plot is a representative plot to show gating scheme (FIG. 3A). A representative image of Fabry iPSC cardiomyocytes following immunocytochemistry with cTNT (red) and DAPI (blue), a nuclear stain (FIG. 3B). Scale bar=100 μm. cTNT: cardiac troponin T, cardiomyocyte marker. n=3, biologic replicates.
Figure 3B:
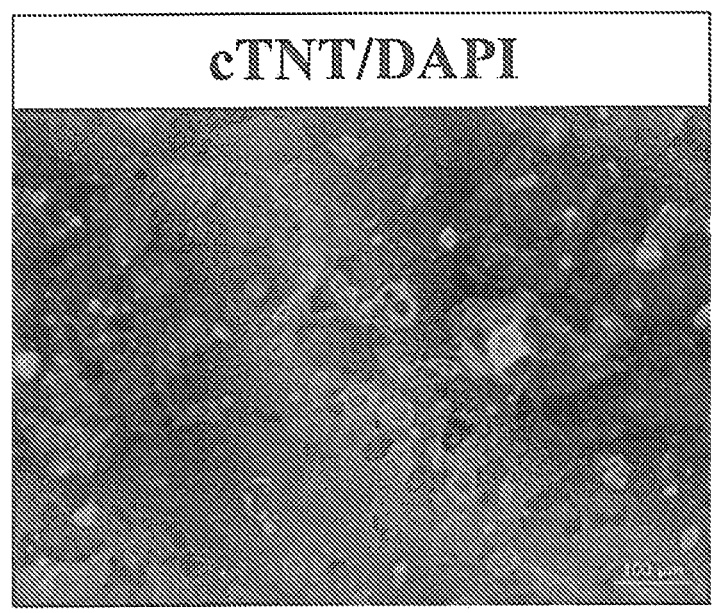

Fabry patient fibroblasts were reprogrammed using the Simplicon RNA Reprogramming Kit to create a human Fabry disease cell model. Fibroblasts were transfected with type. Generated cardiomyocytes began beating around 7 days after differentiation and continued to beat until end point analyses (data not shown). Flow cytometry and immunocytochemistry was done on the Fabry iPSC cardiomyocytes to examine purity using a cardiac specific maker, cardiac troponin T (cTNT). The differentiation yielded 97% cTNT positive cells (FIG. 3A), confirmed by immunocytochemistry staining (FIG. 3B).

Figure 4A:
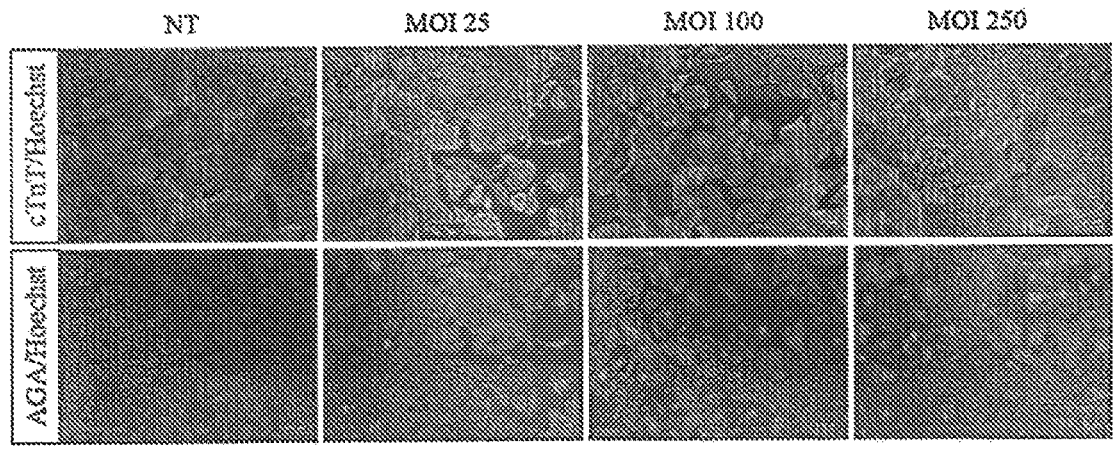
FIGS. 4A-C Transduction of Fabry Diseased iPSC-Cardiomyocytes with recombinant AAV (rAAV) particles comprising (i) a capsid with a capsid protein of SEQ ID NO:4 and (ii) a nucleic acid comprising a nucleotide sequence of SEQ ID NO: 1 operably linked to a CAG promoter, Leads to Expression of AGA Protein. Immunocytochemistry (ICC) showed expression of cardiac troponin T (cTnT) (green), alpha-galactosidase (red), and nuclei counterstain with Hoechst (blue) in Fabry iPSC cardiomyocytes transduced with the AAV (FIG. 4A). Fabry iPSC cardiomyocytes transduced with the AAV were co-stained with cTnT and alpha-galactosidase to determine the percent of Fabry iPSC cardiomyocytes expressing AGA (FIG. 4B). Robust expression of AGA protein seen by Western blot analysis of Fabry iPSC cardiomyocytes after transduction with the AAV (FIG. 4C). AGA: alpha galactosidase, MOI: Multiplicity of infection, NT: non-transduced, Gb3: globotriaosylceramide, n=3, Error bars±Standard Deviation; ****$p<0.0001$ compared to NT, ††$p<0.001$, †$p<0.01$ compared to MOI 25, One-way ANOVA, Tukey post-hoc compared to NT.

Transduction with rAAV Carrying the Codon Optimized GLA Gene of SEQ ID NO: 1 in Fabry Diseased iPSC-Cardiomyocytes Leads to Robust AGA Fabry iPSC cardiomyocytes were cultured for 14 days post seeding into experimental plates prior to transduction of rAAV particles comprising (i) a capsid with a capsid protein of SEQ ID NO:4 and (ii) a nucleic acid comprising a nucleotide sequence of SEQ ID NO:1 operably linked to a CAG promoter of SEQ ID NO:5. Fabry iPSC cardiomyocytes were transduced at MOIs of 25, 100 or 500. The doses were determined from previous transduction efficiency data using an rAAV comprising (i) a capsid with a capsid protein of SEQ ID NO:4 and (ii) a nucleic acid comprising an EFGP gene operably linked to a CAG promoter. Cells were harvested six days post-transduction. Importantly, non-transduced Fabry iPSC cardiomyocytes exhibited a lack of AGA protein by ICC, flow cytometry and Western blot, making them a relevant disease model to examine AGA expression levels and activity following introduction of the codon optimized GLA gene of SEQ ID NO:1. Immunocytochemistry (ICC) of non-transduced cells showed a lack of AGA protein expression, whereas cells transduced with the rAAV exhibited robust AGA staining (FIG. 4A).

Figure 4B:
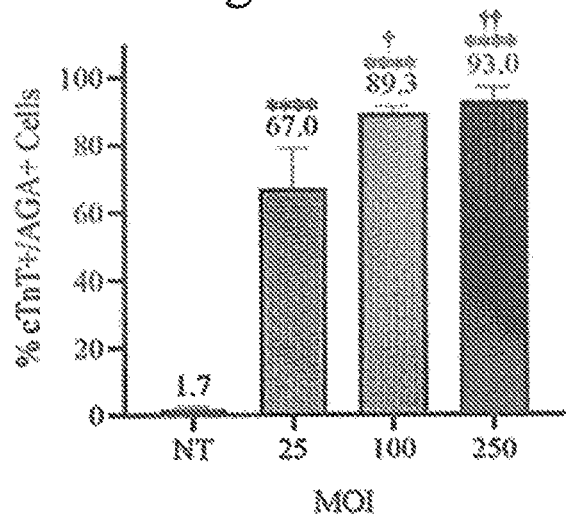

Cells were also harvested for flow cytometry and stained for viability, AGA and cTNT. The double positive population was quantified indicating mature cardiomyocytes (cTNT positive) that had expression of AGA (FIG. 4B). A striking dose dependent AGA protein expression response was observed following transduction with the rAAV in mature cardiomyocytes. A MOI of only 25 led to 67% cTNT and AGA double positive cells (cTNT+/AGA+) indicating that the rAAV can robustly transduce Fabry iPSC cardiomyocytes and express the codon optimized transgene payload. A MOI of 100 led to 89% cTNT+/AGA+ and a MOI of 250 increased the double positive population to 93%.

Figure 4C:
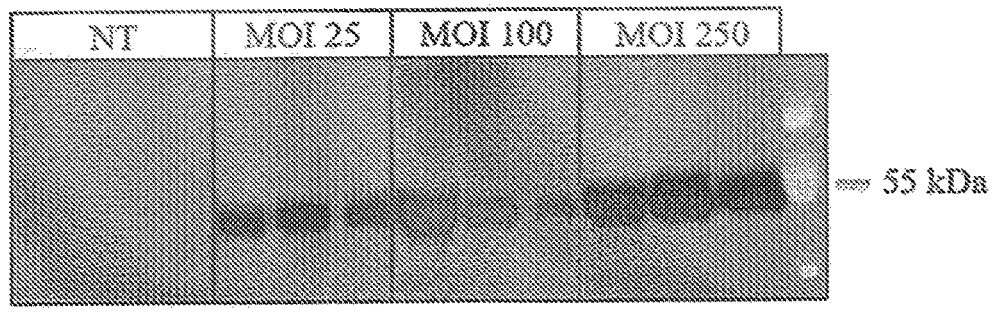

Total protein was extracted from transduced Fabry iPSC cardiomyocytes for Western blot to examine total AGA protein in cell lysates. Non-transduced cells lacked AGA protein, an indicator of disease phenotype. Fabry iPSC cardiomyocytes transduced with the rAAV showed strong AGA protein expression at the correct size of 49 kDa, after probing with an anti-AGA antibody (FIG. 4C).

Figure 5A:
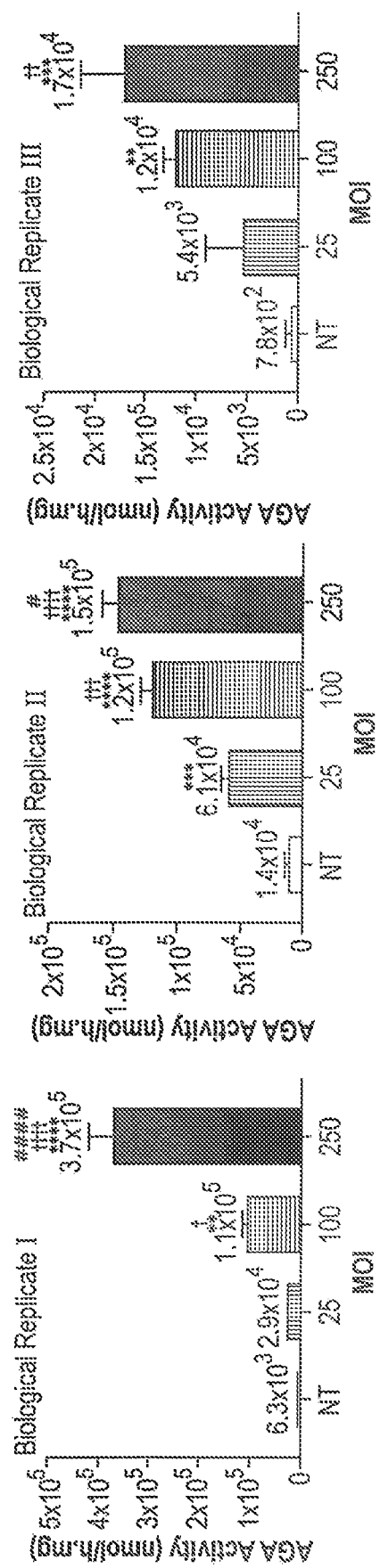
FIGS. 5A-5B Enhanced AGA activity following Transduction with rAAV comprising (i) a capsid with a capsid protein of SEQ ID NO:4 and (ii) a nucleic acid comprising a nucleotide sequence of SEQ ID NO:1 operably linked to a CAG promoter in Fabry Diseased iPSC-Cardiomyocytes. Fabry iPSC cardiomyocytes transduced with the AAV showed a dose dependent increase in AGA activity. Three biologic replicates are quantified individually due to the inherent variability within the kit and plate reader for each run. Technical replicates were performed within each experiment (FIG. 5A). ICC of globotriaosylceramide (Gb3, pink) and nuclei counterstain with Hoechst (blue) (FIG. 5B). AGA=alpha galactosidase, MOI=Multiplicity of infection, NT=non-transduced, Gb3=globotriaosylceramide, n=3, Error bars±Standard Deviation; **$p<0.0001$, *$p<0.004$, **$p=0.005$ compared to NT, ††††$p<0.0001$, †††$p=0.0001$, ††$p<0.004$; †$p<0.02$ compared to MOI 25, #$p<0.02$ compared to MOI 100. One-way ANOVA, Tukey post-hoc compared to NT.

Enhanced AGA Activity Following, rAAV Transduction in Fabry Diseased iPSC-Cardiomyocytes Transduced Fabry iPSC cardiomyocytes were lysed with alpha-galactosidase buffer and used to quantify alpha-galactosidase activity with respect to its alpha linkage cleavability. Fabry iPSC cardiomyocyte samples were incubated with an alpha-galactosidase specific synthetic substrate for one hour to fluorometrically quantify the amount of substrate cleaved. Data revealed a dose dependent increase in AGA activity following transduction of an rAAV comprising (i) a capsid with a capsid protein of SEQ ID NO:4 and (ii) a nucleic acid comprising a nucleotide sequence of SEQ ID NO:1 operably linked to a CAG promoter of SEQ ID NO:5 in Fabry iPSC cardiomyocytes (FIG. 5A).

Figure 5B:
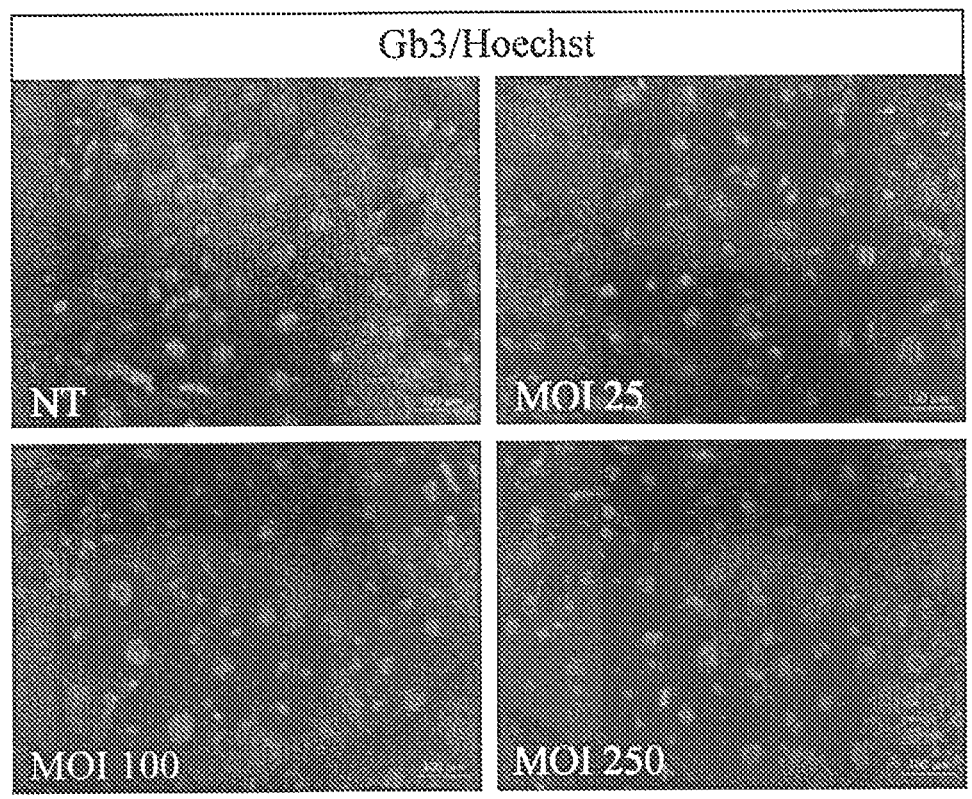

A hallmark pathology of Fabry disease is cellular Gb3 accumulation (Waldek et al., Life expectancy and cause of death in males and females with Fabry disease: findings from the Fabry Registry. *Genetics in Medicine: Official Journal of the American College of Medical Genetics*, 1/(11), 790-796 (2009)). In non-transduced Fabry iPSC cardiomyocytes there was substantial Gb3 cellular accumulation observed through Gb3 immunostaining and fluorescent microscopy (FIG. 5B, top left panel). Transduction of the rAAV at a MOI as low as 25, drastically reduced Gb3 accumulation visualized through a decrease in Gb3 immunostaining (FIG. 5B).

Conclusion

There is a compelling and urgent need for a durable treatment such as a single administration intravenous gene therapeutic targeted to key tissues that expresses GLA cell-autonomously, reducing Gb3 and thereby improving clinical outcomes. The experimental data demonstrates that delivery of a codon optimized GLA gene of SEQ ID NO:1 via an AAV with a capsid comprising a capsid protein of SEQ ID NO:4 efficiently targets Fabry disease key organs, particularly cardiac tissue. Transduction of this AAV in Fabry diseased iPSC cardiomyocytes resulted in rapid cell autonomous dose-related AGA protein expression and activity intracellularly, well above basal levels. The increase in AGA activity resulted in clearance of Gb3, the accumulation of which is considered central to the pathogenesis of Fabry disease in humans.

Example 3—Codon Optimized GLA cDNA Sequence is Expressed at Higher Levels in Endothelial Cells from Patients with Fabry Disease Materials and Methods
Endothelial Differentiation Fabry iPSCs were maintained and sub-cultured in 6-well plates every 3-4 days prior to differentiation. Two 12-well plates were pre-coated with Growth Factor Reduced Matrigel (Corning). Fabry iPSCs were grown until 80-100% confluency in mTESRI. Upon reaching the appropriate density, cultures were subjected to sequential GSK3B and VEGF activation, followed by expansion in StemPro-34 media, following previously published differentiation paradigm (Chalet Meylan, L., Patsch, C., & Thoma, E. (2015). Endothelial cells differentiation from hPSCs. *Protocol Exchange*. www.doi.org/10.1038/protex.2015.055. On day six, endothelial cells were purified by magnetic cell sorting and were frozen in $5 \times 10^6$ aliquots in CryoStor10 (Stem Cell Technologies). Endothelial cells were thawed at 2.6E+4 cells per $cm^2$ onto Fibronectin coated plates in StemPro-34 SFM (1X) media supplemented with $VEGF_{165}$ (Peprotech), IX Glutamax (Thermo Fisher), and IX Penicillin/Streptomycin (Gibco 15140-122). Endothelial cells were split 1:2 five days after thawing using Accutase cell detachment solution.

Endothelial Cell Transduction

Endothelial cells were transduced with rAAV comprising (i) a capsid with a capsid protein of SEQ ID NO:4 and (ii) a nucleic acid comprising a nucleotide sequence of SEQ ID NO: 1 operably linked to a CAG promoter four days after seeding. Twenty-four hours after transduction, the media was aspirated, and fresh StemPro-34 SFM (1×) media was added. Media was changed every other day. Three wells were harvested to obtain a cell count. Cells were transduced at multiplicity of infections (MOI) of 50, 100, 500, and 1000, based on the cell count and viral titer. Vehicle was added such that the volume was equivalent to that of the highest MOI. Cells were incubated for 24 hours and then received a media change. The media was changed every other day until harvest, four days post transduction.

For immunocytochemistry, 10 μM Gb3 (Matreya, LLC.) was added one day prior, with virus, and to any feedings following transduction to promote Fabry disease-associated accumulation of Gb3.

Immunocytochemistry (ICC)
Fabry iPSC Endothelial ICC

Certain modifications to cell culture were made to enable Gb3 detection in response to transduction with the rAAV. First, cells were cultured on Fibronectin-coated glass chamber slides (LabTek). Cells were loaded with 10 μM Gb3, two days prior, upon transduction, and upon washout of virus. Four days post infection, cells were washed once with Phosphate Buffered Saline without magnesium or calcium (PBS−/−) and fixed with 4% paraformaldehyde for one hour at room temperature. Cells were then washed 3 times with PBS−/− and blocked for 30 minutes with 2% bovine serum albumin and 5% goat serum in 0.2% Triton X-100 in PBS−/−. Primary antibody diluted 1:100 against AGA (Abnova H00002717-B01P, custom Phycoerythroitin conjugate) was incubated with cells in blocking solution for two hours at room temperature. Cells were counterstained with DAPI to visualize the nuclei and were imaged on a Zeiss Axiovert.A1 inverted microscope. Additionally, conjugated BD clone b5b CD77-Alexa-647 (BD 563632) and Miltenyi CD31-FITC were used by incubating fixed cultures with 1:100 antibody in ICC blocking buffer for one hour.

Western Blot

Four days post-transduction, cells were lifted with Accutase and pelleted at 300× g for 5 minutes. Lysates were made using RIPA buffer (Thermo) plus protease inhibitor cocktail (Roche). Lysates were incubated on ice for 15 minutes and centrifuged at 21,000×g for 15 minutes. Supernatants were collected, and a bicinchoninic acid assay (BCA) was run to determine protein concentration. Concentrations were normalized. An SDS-PAGE was run using a 4-12% polyacrylamide gel at 200V for 30 minutes. Protein was transferred to a 0.2 um nitrocellulose membrane and probed with anti-AGA (Atlas, HPA000237, 1:200) and anti-GAPDH (Stem Cell Technologies, 5174, 1:5000) antibodies followed by species specific horseradish peroxidase secondary antibodies overnight. Enhanced chemiluminescence was used to develop protein bands, and band detection was captured on a BioRad ChemiDoc MP. Band quantification was analyzed using Image Lab, Microsoft Excel software and GraphPad Prism8.

AGA Activity Assay

The AGA activity assay was performed with an alpha-galactosidase synthetic fluorometric substrate (BioVision, K407). AGA activity assay was performed according to the manufacturer's protocol with the following changes. Briefly, spent media was collected and snap frozen using liquid nitrogen. Cells were dissociated using trypsin 0.05% and centrifuged at 300×g for 3 mins to remove supernatant. Cells were then lysed with AGA buffer and incubated on ice for 10 mins. Samples were centrifuged at 12,000×g for 10 mins at 4° C. Supernatant was collected and stored at −80° C. The following day, samples were thawed on ice and protein quantification via BCA assay was performed in addition to the AGA activity assay. AGA reaction time was 1 hour, samples were read on the Cytation3 plate reader (BioTek) at 360 excitation/445 emission and gain was set to highest concentration of AGA standard curve.

TABLE 3 list of antibodies

| Antibody | Host | Company-Catalog No. | Dilution |
| --- | --- | --- | --- |
| Primary Antibodies | | | |
| CD31-FITC | Mouse | Miltenyi-130-110-668 | 1:100 |
| CD144-APC | Mouse | Miltenyi-130-102-738 | 1:100 |
| GLA-PE | Mouse | Abnova-H00002717-B01P | 1:100 |
| CD77-Alexa-647 | Mouse | BD-563632 | 1:50 |

Results

Figure 6A:
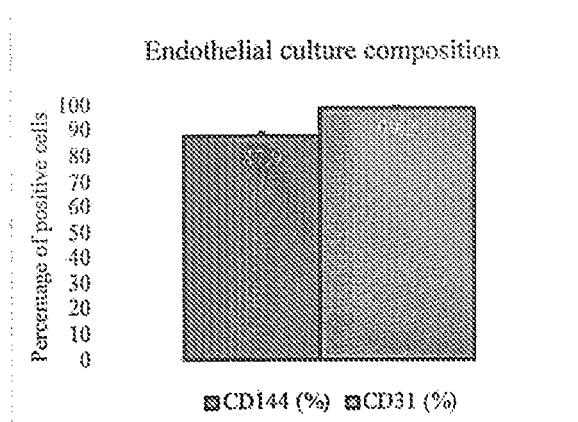
FIGS. 6A-6B Characterization of Fabry Diseased Induced Pluripotent Stem Cell-Derived Endothelial Cells.
Figure 6B:
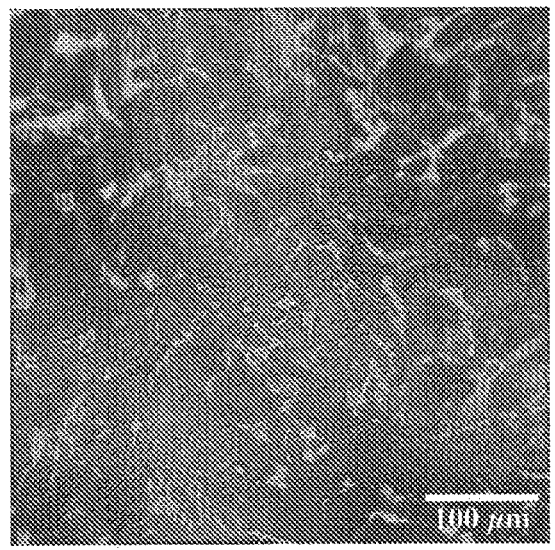

Characterization of Fabry Diseased Induced Pluripotent Stem Cell Derived Endothelial Cells Fabry iPSCs were differentiated into endothelial cells to generate a relevant model of a cell type affected in Fabry disease. Generated endothelial cells were purified by MACS on day 6 for CD144. Flow cytometry and immunocytochemistry was done on the Fabry iPSC endothelial cells to examine purity using an endothelial-specific maker, CD31. The differentiation yielded 99.2% CD31 positive cells (FIG. 6A), confirmed by immunocytochemistry staining at the plasma membrane (FIG. 6B).

Figure 7A:
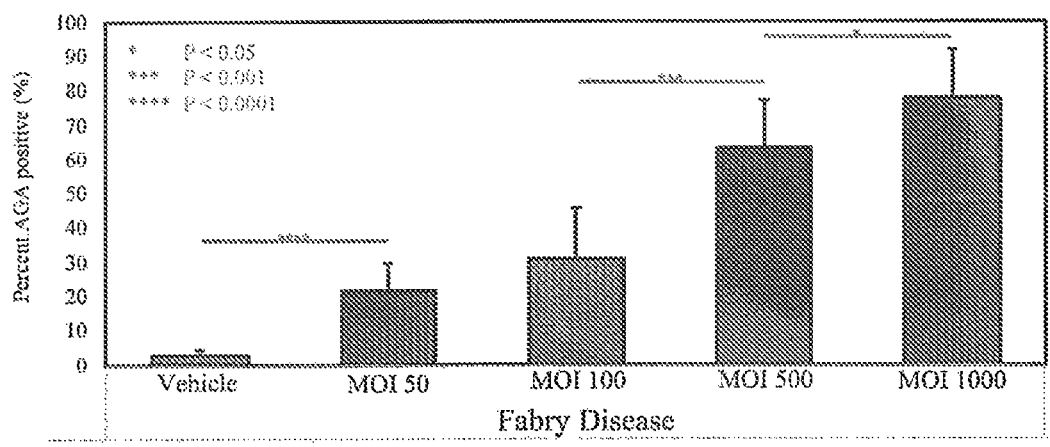
FIGS. 7A-7B Transduction of Fabry Disease iPSC-Endothelial Cells with rAAV comprising (i) a capsid with a capsid protein of SEQ ID NO:4 and (ii) a nucleic acid comprising a nucleotide sequence of SEQ ID NO:1 operably linked to a CAG promoter Leads to Expression of Exogenous AGA by flow and Western.
Figure 8A:
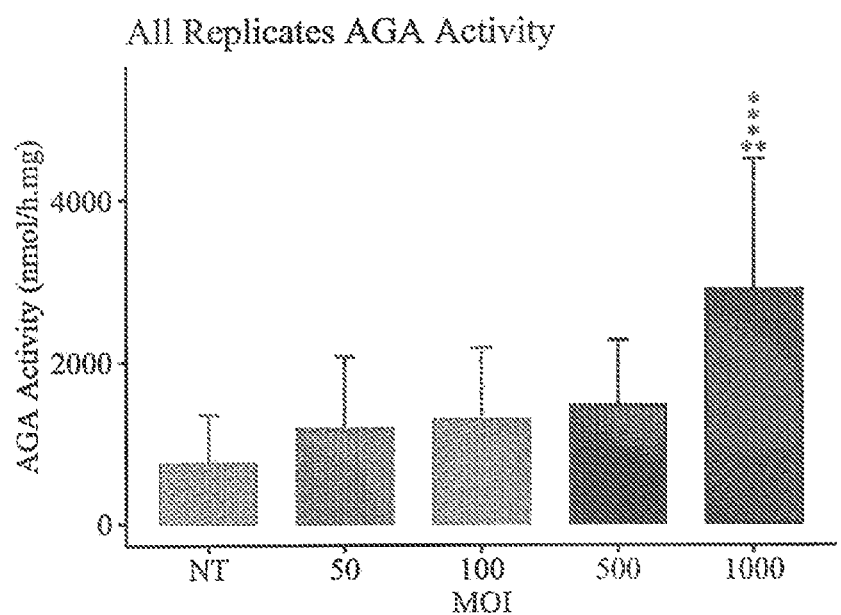
FIGS. 8A-8B. Enhanced AGA activity following transduction with rAAV comprising (i) a capsid with a capsid protein of SEQ ID NO:4 and (ii) a nucleic acid comprising a nucleotide sequence of SEQ ID NO: 1 operably linked to a CAG promoter in Fabry Diseased iPSC-Endothelial Cells.
Figure 8B:
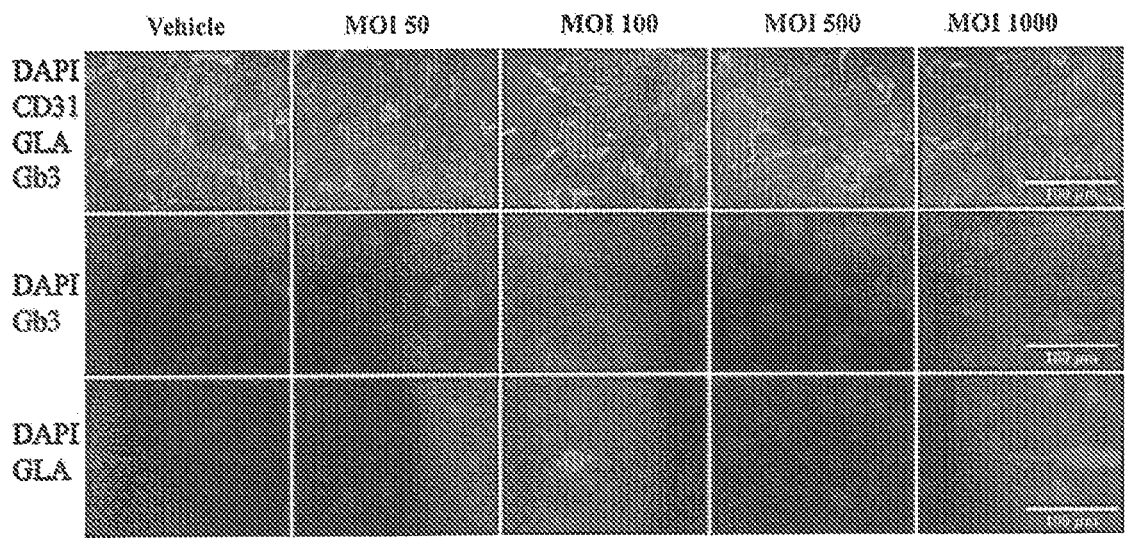

Transduction with rAAV Carrying Codon Optimized GLA of SEQ ID NO:1 in Fabry Disease iPSC-Endothelial Cells Leads to Robust AGA Protein Expression Fabry iPSC endothelial cells were cultured for 11 days from thaw prior to transduction of rAAV comprising (i) a capsid with a capsid protein of SEQ ID NO:4 and (ii) a nucleic acid comprising a nucleotide sequence of SEQ ID NO: 1 operably linked to a CAG promoter at MOIs of 50, 100, 500, and 1000. The doses were determined from transduction efficiency data using an otherwise identical rAAV carrying EGFP under the control of CAG promoter. Cells were harvested four days post-transduction. Flow cytometry showed a dose-dependent increase in AGA-positive cells (FIG. 7A) Immunocytochemistry (ICC) of non-transduced cells showed a lack of AGA protein expression, whereas cells transduced with the rAAV exhibited robust AGA staining (FIG. 8B).

Figure 7B:
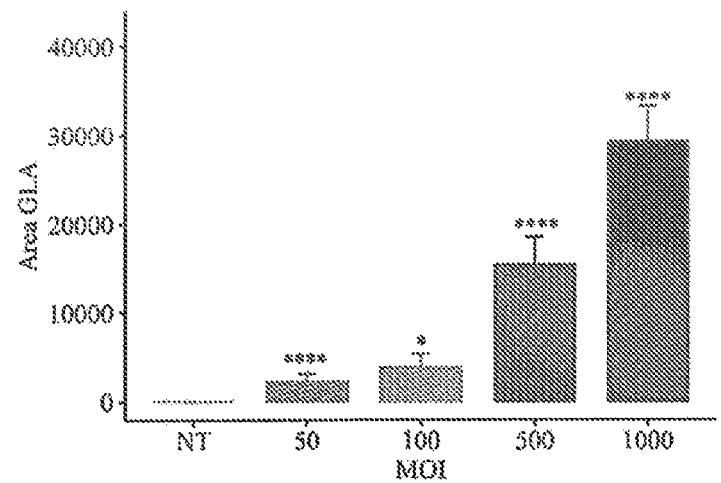
Figure 7B:
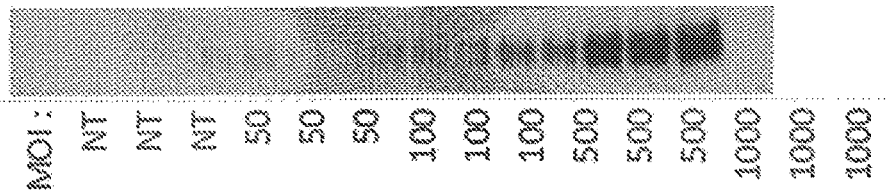

Protein was extracted from transduced Fabry iPSC-derived endothelial cells for Western blotting to examine total AGA protein. Non-transduced cells lacked AGA protein, as was demonstrated by ICC. However, Fabry iPSC endothelial cells transduced with rAAV comprising (i) a capsid with a capsid protein of SEQ ID NO:4 and (ii) a nucleic acid comprising a nucleotide sequence of SEQ ID NO:1 operably linked to a CAG promoter showed a strong AGA protein band at the correct size of 49 kDa (FIG. 7B), after probing with an anti-AGA antibody. Band density was determined (FIG. 7B). Transduction with the rAAV significantly increased total AGA protein for both MOIs compared to non-transduced cells.

Enhanced AGA Activity Following Transduction with rAAV Comprising (i) a Capsid with a Capsid Protein of SEQ ID NO:4 and (ii) a Nucleic Acid Comprising a Nucleotide Sequence of SEQ ID NO: 1 Operably Linked to a CAG Promoter in Fabry Diseased iPSC-Endothelial Cells Transduced Fabry iPSC endothelial cells were lysed with AGA buffer (Biovision, LLC.) and used to quantify AGA activity. Fabry iPSC endothelial cell samples were incubated with an AGA specific synthetic substrate for one hour to fluorometrically quantify the amount of substrate cleaved. Data reveals that Fabry iPSC endothelial cells transduced with the rAAV had enhanced AGA activity compared to Fabry iPSC endothelial cells. See FIGS. 8A and 8B.

Conclusion

Transduction of rAAV carrying codon optimized GLA nucleotide sequence of SEQ ID NO: 1 operably linked to a CAG promoter in Fabry diseased iPSC endothelial cells resulted in rapid cell-autonomous, dose-dependent AGA protein expression and intracellular activity, significantly above basal levels. The increase in AGA activity through expression of the codon optimized GLA transgene resulted in clearance of Gb3, the accumulation of which is considered central to the pathogenesis of Fabry disease in humans.

Example 4—Expression and Functional Analysis of AGA Expressed from Codon Optimized GLA of SEQ ID NO:1 in Plasma and Tissues of Fabry Mouse Model Materials and Methods In Vivo Study Design and Sample Collection Fabry model B6; 129-Gld$^{tm1Kul}$/J (Jackson Labs #003535) (hereafter referred to as GLA-null) or normal C57BL/6 mice at 10-11 weeks of age received a single intravenous tail vein injection on Day 1 of $1\times10^{12}$, $1\times10^{13}$, or $5\times10^{13}$ vg/kg of rAAV comprising (i) a capsid with a capsid protein of SEQ ID NO:4 and (ii) a nucleic acid comprising a nucleotide sequence of SEQ ID NO:1 operably linked to a CAG promoter in Dulbecco's Phosphate-Buffered Saline (DPBS) containing 0.005% Pluronic F-68 or vehicle only (refer to Table 4). Mortality, clinical observations, body weight, food consumption, bioanalytical analyses for AGA activity and Gb3 substrate accumulation, and gross necropsy findings were evaluated. Additionally, tissues from a subset of mice (n=3 per group) were processed and examined for AGA expression and localization by immunohistochemistry (IHC).

Blood samples (Days 1, 15, and 29) or maximum obtainable (Day 56 only) were collected from all animals via the maxillary vein or the vena cava after carbon dioxide inhalation (Day 56 only) for determination of α-galactosidase A (AGA) activity and/or Gb3 substrate accumulation in plasma. Blood samples were collected, processed to plasma, and stored at −60° C. to −90° C. until the samples were tested. Plasma was analyzed for AGA activity prior to dosing on Days 1, 15 and 29, and at study termination on Day 56. Plasma Gb3 and lysoGb3 levels were analyzed on Day 56. Samples of heart, kidney, liver, and small intestine were also collected at study termination and analyzed for AGA activity and Gb3 substrate level. Representative samples of select tissues (heart, liver, kidney, and small intestine) from a subset of animals in each group were collected and immediately preserved in 10% neutral buffered formalin (20-30× volume of the tissue). Tissues were fixed for approximately 48 hours (±1 hour) at room temperature and then transferred to 70% ethanol.

TABLE 4

Scheme of Treatment Groups for Fabry Mouse Dose-Ranging and Efficacy Study

| Group | Genotype | rAAV (vg/kg) | N |
|---|---|---|---|
| 1 | C57BL/6 | Vehicle | 15 |
| 2 | GLA-null | Vehicle | 15 |
| 3 | GLA-null | $1 \times 10^{12}$ | 15 |
| 4 | GLA-null | $1 \times 10^{13}$ | 15 |
| 5 | GLA-null | $5 \times 10^{13}$ | 15 |

Plasma and Tissue Activity Analysis

AGA enzyme activity was detected and quantified via the production of 4-methylumbelliferone using a validated assay. Briefly, samples were diluted in Activity Buffer containing 4-Methylumbelliferyl-α-D-galactopyranoside and incubated for 1 hour at room temperature. Fluorescence emission was quantified using a plate reader equipped with fluorescence detection at 366 excitation/450-475 emission and compared to a standard curve. Total protein within tissue samples was quantified using a BCA assay.

Plasma Substrate Analysis

LysoGb3 (m/z 786) and its analogs (m/z 784, m/z 802, and m/z 804), and Gb3 and its isoforms (C16:0, C18:0, C22:0, C24:1, and C24:0) in plasma were analyzed as described (Boutin & Auray-Blais, 2014. *Analytical Chemistry*, 86(7), 3476-3483. www.doi.org/10.1021/ac404000d; Provencal et al. 2016, Bioanalysis, 8(17), 1793-1807. www.doi.org/0.4155/bio-2016-0116). Briefly, plasma samples drawn 56 days post-dose (42 day samples were saved and archived but not analyzed) were spiked with glycinated-lysoGb3 (Matreya LLC; State College, PA) as the internal standard and purified by solid phase extraction using mixed-mode strong cation exchange (MCX) cartridges (Waters Corporation, Milford, MA). The collected phase was dried under a nitrogen stream, reconstituted in 50% acetonitrile/0.1% formic acid, and injected onto an Acquity I-Class ultra performance liquid chromatography (UPLC) system (Waters Corporation, Milford, MA) using an BEH C18 column and lysoGb3 was detected simultaneously with the spiked-in internal standards (glycinated-lysoGb3) using a Xevo TQ-S (Waters Corporation) triple quadrupole tandem mass spectrometer.

For Gb3 analysis, the plasma samples were spiked with Gb3 (C18:0D3) (Matreya LLC; State College, PA) as the internal standard and purified by liquid-liquid extraction with tert-butyl methyl ether. Samples were saponified with potassium hydroxide, neutralized with acetic acid, centrifuged, and the organic layer collected and dried under a stream of nitrogen. The sample was reconstituted and injected onto an Alliance HPLC 2795 system (Waters Corporation, Milford, MA) using a Zorbax Bonus-RP Guard column cartridge (4.6×12.5 mm, Agilent Technologies). Analytes were then detected simultaneously with the spiked-in internal standards using a Quattro micro triple quadrupole tandem mass spectrometer (Waters Corporation).

Tissue Substrate Analysis

Gb3 isoforms and analogs (C16:0, C18:0, C20:0, C22:0, and C24:1) in tissues important for the treatment of Fabry disease were analyzed as described (Provencal et al. 2016, Bioanalysis, 8(17), 1793-1807. www.doi.org/10.4155/bio-2016-0116). Briefly, frozen heart, kidney, liver, small intestine, and spleen tissue samples in reinforced tubes were thawed, five ceramic beads added to each tube, and the samples homogenized in methanol using a Bead Disruptor 12 bead mill homogenizer (Omni International; Kennesaw, GA). Lysates were then extracted and analyzed in the same manner as the plasma samples, described above. All tissues were collected from n=12 animals per group, except for the hearts from n=6 animals per group due to tissue size limitations to enable AGA activity analysis from the other six animals. The remaining three animals from each treatment group were used for immunohistochemistry analysis.

Data are represented as a response ratio, which is the ratio of the mass spectrometer peak area of the sample analyte divided by the peak area of the Gb3 internal standard (Gb3 (C18:0D$_3$)). For each tissue, the total response ratios of all six Gb3 isoforms/analogs was examined. Because of the nature of this ratio, there are no units ascribed to this Response Ratio.

Statistical Analysis

Statistical analysis was performed by the biostatistics group at Charles River Laboratories—Mattawan (Mattawan, MI). Data analysis was performed on the aggregate values of all lysoGb3 and Gb3 isoforms/analogs to ensure that the data were capturing a broad spectrum of AGA substrates. All "not detected" (N.D.) values in both the plasma lysoGb3 and the tissue Gb3 data sets were treated as having values of zero for the purposes of data analysis. A sensitivity analysis was performed substituting LLOD (lower limit of detection) values for those N.D. values.

Tests to assess homogeneity of group variances and the normality of the residuals were performed at the 0.01 level of significance. The experimental unit used for the Gb3 data analysis was the individual animal.

The raw data was tabulated within each time interval, and the mean and standard deviation calculated for each endpoint by group. For each endpoint, treatment groups were compared to the control group using the analysis outlined below. Data for some endpoints, as appropriate, were transformed by either a log or rank transformation prior to conducting the specified analysis.

TABLE 5

Statistical Comparisons Calculated
Statistical Comparisons

| Group | Versus Groups |
|---|---|
| 1 | 2, 3, 4, 5 |
| 2 | 3, 4, 5 |

For endpoints and/or parameters (within each collection interval) that demonstrate variability, and where sample sizes for all groups are three or greater, the system tested the normality of the residuals and homogeneity of variances to see whether the data was approximately normal or whether a log transformation or rank transformation should be used. Levene's test was used to assess homogeneity of group variances and Shapiro-Wilk's test was used to test the normality of the residuals.

On the raw data, if Levene's test was not significant ($p \geq 0.01$) and Shapiro-Wilk's test was not significant ($p \geq 0.01$), then a normal distribution was used. If either the Levene's test was significant ($p < 0.01$) or Shapiro-Wilk's test was significant ($p < 0.01$), normality and homogeneity of variances were tested with a log transformation used on the data.

On the log transformed data, if Levene's test was not significant ($p \geq 0.01$) and Shapiro-Wilk's test was not significant ($p \geq 0.0$), then a log normal distribution was used. If either the Levene's test was significant ($p < 0.01$) or Shapiro-Wilk's test was significant ($p < 0.01$), then a rank transformation was used on the data.

A one-way analysis of variance using the appropriate transformed data was used to test each endpoint for the effects of treatment (Edwards & Berry, 1987, *Biometrics*, 43(4), 913-928.)

If the treatment effect was significant ($p < 0.05$), linear contrasts was constructed for pair-wise comparison of treatment groups as described above. Results of these pair-wise comparisons were reported at the 0.05 and 0.01 significance levels after adjustment for multiple comparisons using the methods of Edwards and Berry (Edwards & Berry, 1987, *Biometrics*, 43(4), 913-928). All tests were two-tailed tests unless indicated otherwise.

Results and Discussion
Plasma and Tissue AGA Analysis

Figure 9A:
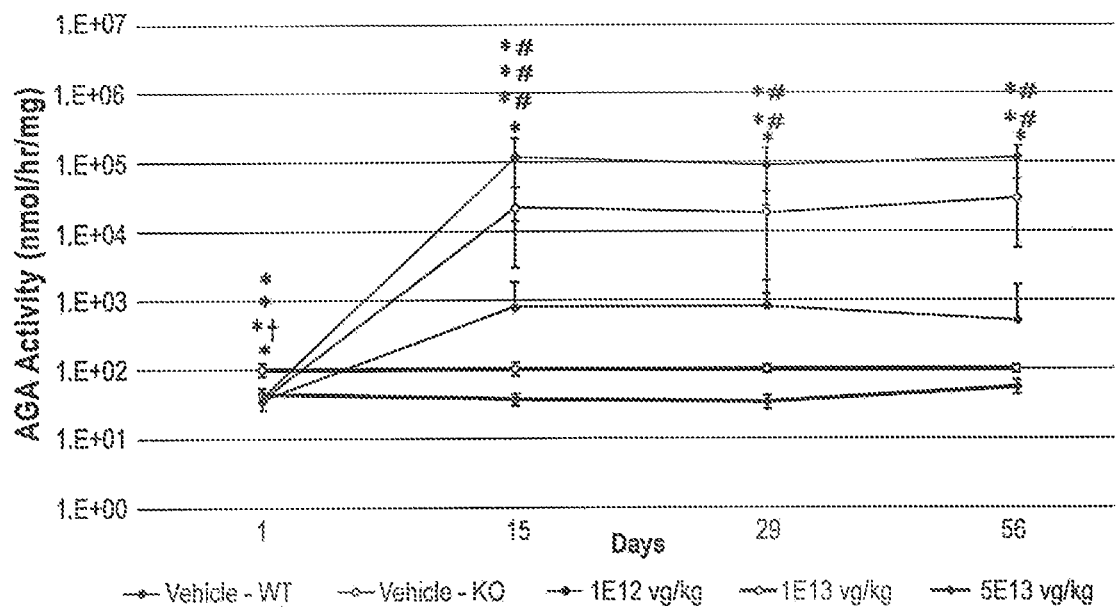
FIG. 9A-9B. AGA activity following transduction with rAAV comprising (i) a capsid with a capsid protein of SEQ ID NO:4 and (ii) a nucleic acid comprising a nucleotide sequence of SEQ ID NO:1 operably linked to a CAG promoter of SEQ ID NO:5 in a mouse model of Fabry Disease.

A single IV dose of rAAV as described above (comprising (i) a capsid with a capsid protein of SEQ ID NO:4 and (ii) a nucleic acid comprising a nucleotide sequence of SEQ ID NO:1 operably linked to a CAG promoter) resulted in consistent and dose-dependent increases in plasma AGA activity at every evaluated timepoint (FIG. 9A). These increases were maintained over the eight-week duration of the study (FIG. 9A).

Figure 9B:
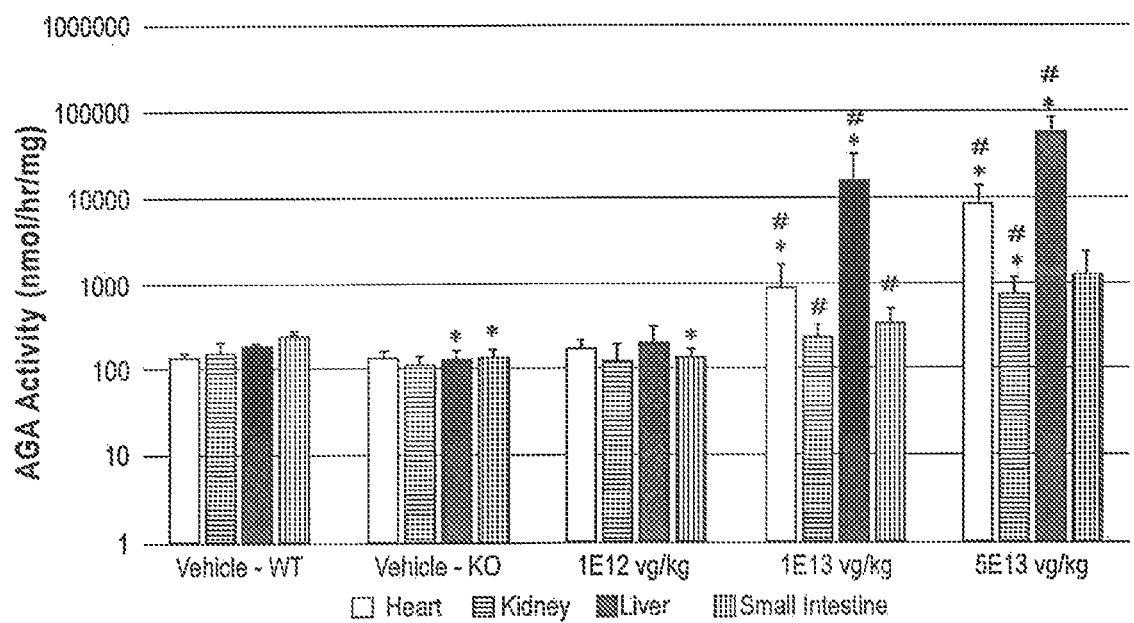
Figure 10:
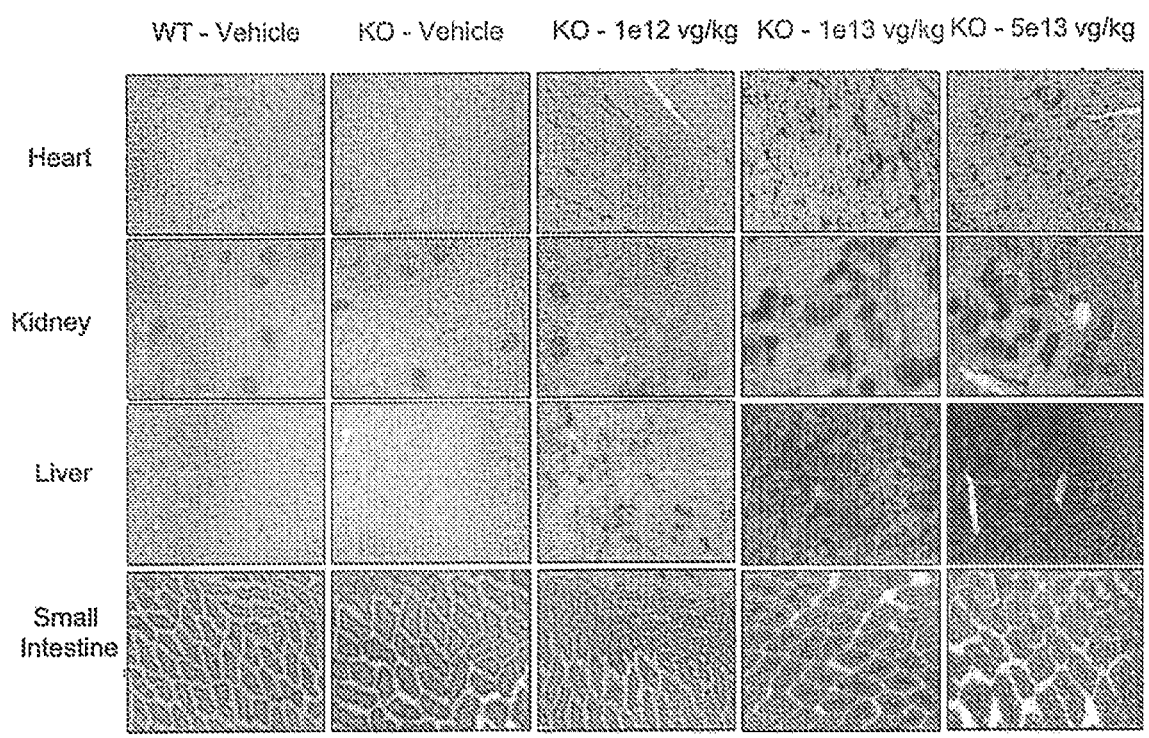
FIG. 10. Detection of AGA by IHC in Tissues of Normal (WT) or Fabry (KO) Mice 8 Weeks After a Single IV Dose of rAAV comprising (i) a capsid with a capsid protein of SEQ ID NO:4 and (ii) a nucleic acid comprising a nucleotide sequence of SEQ ID NO:1 operably linked to a CAG promoter of SEQ ID NO:5. Representative images of four tissues (heart, kidney, liver and small intestine) showing IHC staining for AGA (dark brown color). IHC staining for each tissue shows a dose-dependent increase in AGA detection after a single intravenous dose of rAAV comprising (i) a capsid with a capsid protein of SEQ ID NO:4 and (ii) a nucleic acid comprising a nucleotide sequence of SEQ ID NO:1 operably linked to a CAG promoter of SEQ ID NO:5 in a mouse model of Fabry Disease compared to wild-type mice treated with vehicle or Fabry mice treated with vehicle. IHC was performed on tissues collected from n=3 animals per group.

At study termination, an increase in AGA activity was detected in the kidney and small intestine compared to vehicle-treated mice, with higher levels noted in the heart at the high dose of $5 \times 10^{13}$ vg/kg (FIG. 9B). In the liver, high AGA activity levels were observed in mice treated with both $1 \times 10^{13}$ and $5 \times 10^{13}$ vg/kg (FIG. 9B). These data suggest that a single IV dose of rAAV as described above (comprising (i) a capsid with a capsid protein of SEQ ID NO:4 and (ii) a nucleic acid comprising a nucleotide sequence of SEQ ID NO:1 operably linked to a CAG promoter) results in significant expression of AGA activity in plasma particularly at doses of $1 \times 10^{13}$ and higher. Significant expression was also seen out to eight weeks post-dose in the heart and liver. To visually confirm AGA expression in tissues, heart, kidney, small intestine, and liver were collected, fixed, paraffin-embedded, and subjected to IHC for AGA as described above. A dose-dependent increase in AGA expression was observed in all tissues examined (FIG. 10).

Plasma lysoGb3 Analysis

A single IV dose of rAAV as described above (comprising (i) a capsid with a capsid protein of SEQ ID NO:4 and (ii) a nucleic acid comprising a nucleotide sequence of SEQ ID NO:1 operably linked to a CAG promoter) resulted in a dose-dependent and significant ($P < 0.01$) reduction at all levels of total lysoGb3 levels in plasma eight weeks after dosing. Four different analogs of lysoGb3 were examined, represented by their mass-to-charge ratios (m/z): m/z 786, m/z 784, m/z 802, and m/z 804. Examining the aggregate change of all analogs together, lysoGb3 was substantially reduced at all dose levels of the rAAV.

Figure 11:
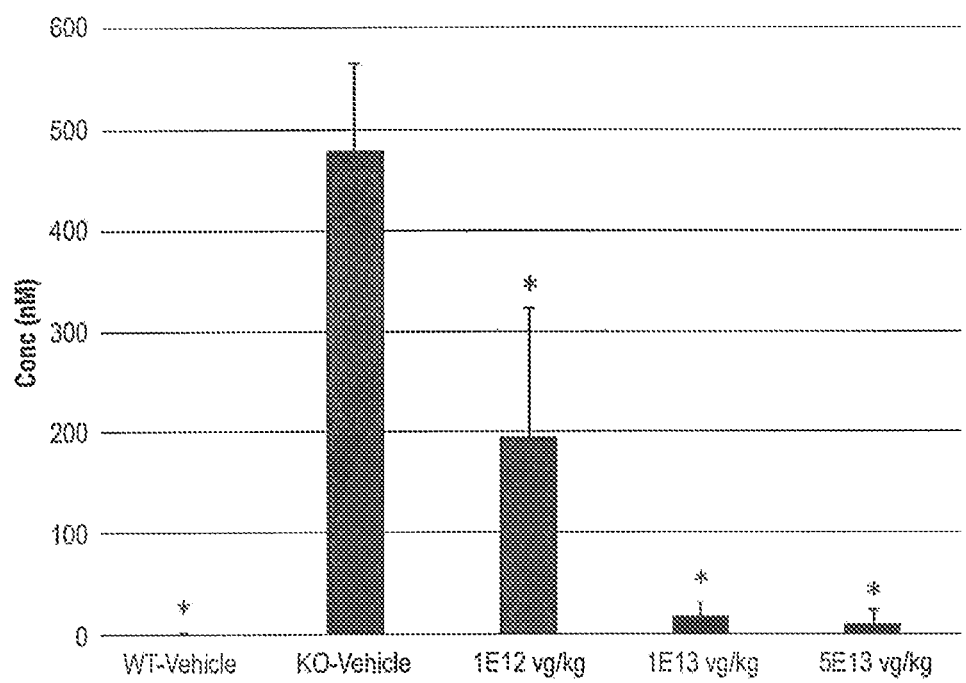
FIG. 11. LysoGb3 Levels in Plasma. LysoGb3 reduction in plasma after single IV dose of rAAV comprising (i) a capsid with a capsid protein of SEQ ID NO:4 and (ii) a nucleic acid comprising a nucleotide sequence of SEQ ID NO: 1 as described in the previous figures. Mean total concentration of lysoGb3 (m/z 786) and its analogs (m/z 784, m/z 802, and m/z 804) measured in plasma from a total of n=15 per group of either C57BL/6 (WT) or GLA null (KO) animals treated with vehicle, or GLA null animals treated with the indicated doses of rAAV carrying codon optimized GLA of SEQ ID NO:1. Error bars indicate standard deviation. * indicates P<0.01 compared with vehicle-treated GLA null.

Whereas wildtype mice exhibit only $2.11 \pm 0.26$ nM of lysoGb3 detected in the plasma, vehicle-treated Fabry mice have a significant lysoGb3 accumulation in plasma of more than $477.37 \pm 88.5$ nM (FIG. 11). A single low IV dose of $1 \times 10^{12}$ vg/kg of the rAAV reduced the concentration of lysoGb3 in plasma of Fabry mice by more than 58%, to $197.5 \pm 124.5$ nM ($P < 0.01$). The mid dose of $1 \times 10^{13}$ vg/kg of the rAAV resulted in a 96% reduction of plasma lysoGb3 in Fabry mice, to $19.1 \pm 13.46$ nM ($P < 0.01$). Further increasing the dose of the rAAV to $5 \times 10^{13}$ vg/kg resulted in a similar reduction in lysoGb3 to $10.57 \pm 13.85$ nM ($P < 0.01$). Data from the aggregated change of all analogs are summarized in Table 6 below:

TABLE 6

Plasma lysoGb3 Levels at Day 56 Post-IV Injection

| Group | Genotype | Treatment | Dose (vg/kg) | Mean of All LysoGb3 Analogs (nM) | Control LSMEAN minus Treatment LSMEAN | P Value compared to Group 2 | Significant At |
|---|---|---|---|---|---|---|---|
| 1 | WT | Vehicle | N/A | 2.11 ± 0.26 | N/A | N/A | N/A |
| 2 | GLA-null | Vehicle | N/A | 477.37 ± 88.5 | N/A | N/A | N/A |
| 3 | GLA-null | rAAV | $1 \times 10^{12}$ | 197.5 ± 124.5 | −13.3905 | 0.0000 | <0.01 |
| 4 | GLA-null | rAAV | $1 \times 10^{13}$ | 19.1 ± 13.46 | −30.5238 | 0.0000 | <0.01 |
| 5 | GLA-null | rAAV | $5 \times 10^{13}$ | 10.57 ± 13.85 | −42.0571 | 0.0000 | <0.01 |

Gb3 and Gb3 analogs were also examined in plasma but only lysoGb3 data are discussed here because in plasma lysoGb3 is a more relevant form of substrate for the clinical disease (Boutin & Auray-Blais, 2014, *Analytical Chemistry*, 86(7), 3476-3483. //doi.org/10.1021/ac404000d).

Tissue Gb3 Analysis

All tissues examined exhibit significantly greater amounts of Gb3 in GLA-null Fabry mice relative to wildtype C57BL/6, confirming the expected accumulation of AGA substrate associated with the Fabry disease phenotype. In all tissues and at all dose levels, there are dose-dependent reductions of Gb3 following treatment with a single IV dose of the rAAV. Specific results from heart, kidney, liver, and small intestine are described below. Spleen was also collected and analyzed, but those results are not discussed here since spleen is not of clinical significance to Fabry disease. Tissue Gb3 data are represented as a response ratio, which is the ratio of the mass spectrometer peak area of the sample analyte divided by the peak area of the Gb3 internal standard (Gb3 (C18:01D$_3$)).

Heart Gb3 Analysis

Figure 12:
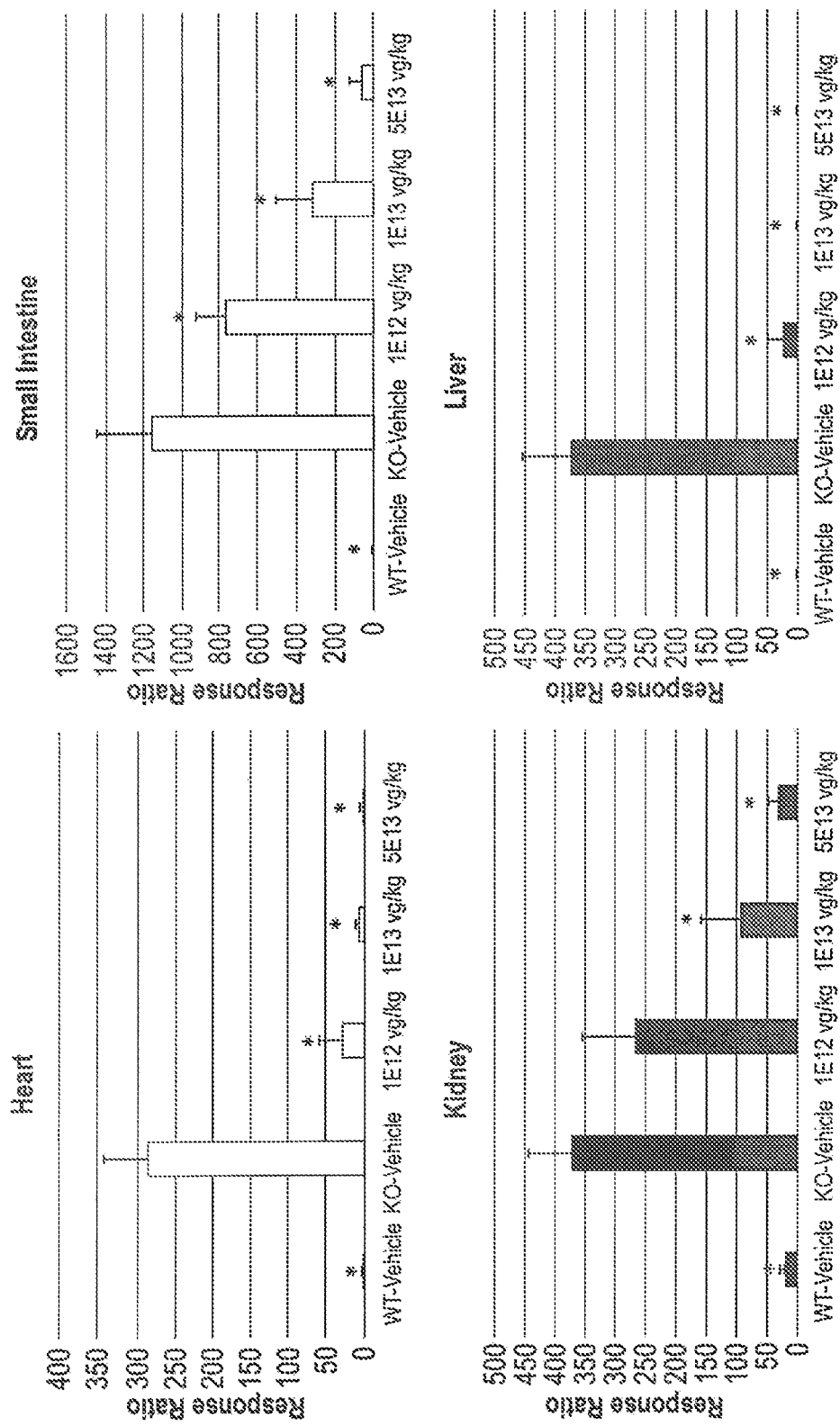
FIG. 12. Gb3 Analysis in Tissues. Tissues were collected from n=6 (hearts) or n=12 (kidney, small intestine, liver) from C57BL/6 (WT) or GLA-null (KO) mice treated with vehicle or increasing doses of rAAV comprising (i) a capsid with a capsid protein of SEQ ID NO:4 and (ii) a nucleic acid comprising a nucleotide sequence of SEQ ID NO: 1 (as described in the previous Figures) at Day 56 post-1V injection. Bars represent the mean response ratio of all Gb3 species measured. Error bars represent standard deviation. * indicates P<0.005 when compared to Group 2 ("KO-Vehicle").

Whereas wildtype C57BL/6 mice exhibit response ratio of 2.9±0.2 in the heart, GLA-null Fabry mice show a significant substrate accumulation measured at 285.5≅56.5 (P<0.01). A single IV injection of the rAAV results in a dose-dependent clearance of Gb3 in the Fabry mice (FIG. 12). The low dose of 1×10$^{12}$ vg/kg reduced the Gb3 content of the heart by 89.4%, to 30.1±30.5. The mid dose level of rAAV of 1×10$^{13}$ vg/kg reduced the Gb3 level by more than 96%, to 9.9±3.7. The high dose of 5×10$^{13}$ vg/kg cleared more than 98% of Gb3, to 4.4±2.2. These results represent an average of n=6 animals per group. All Gb3 reductions in heart were statistically significant (P<0.01) in comparison to Group 2 (vehicle-treated GLA-null).

Kidney Gb3 Analysis

Vehicle-treated wildtype C57BL/6 mice show response ratio of 25±4.1 whereas the GLA-null Fabry mice exhibit 373:1-71. A single IV dose of the rAAV resulted in a dose-dependent and statistically significant (P<0.0 1) clearance of Gb3, exhibiting a 28.3%, 74.4%, and 90.7% reduction 56 days after treatment with 1×10$^{12}$, 1×10$^{13}$, or 5×10$^{13}$ vg/kg, respectively. Gb3 reductions in kidney at the mid and high dose levels were statistically significant (P<0.01) in comparison to Group 2 (vehicle-treated GLA-null). The low dose 1×10$^{12}$ vg/kg did not achieve significance (P=0.0537) although the therapeutic product does exhibit a trending reduction in Gb3 even at this low dose level (FIG. 12).

Liver Gb3 Analysis

The Gb3 levels, measured in Response Ratio, in liver lysates of wildtype C57BL/6 and GLA-null Fabry mice were 2.9±0.5 and 377±75, respectively. Liver Gb3 accumulation was almost completely cleared by even the low dose of the rAAV (FIG. 12). The 1×10$^{12}$ vg/kg dose resulted in a 93.1% reduction of Gb3, to 26±24. The mid and high doses of 1×10$^{13}$ or 5×10$^{13}$ vg/kg resulted in nearly complete (>99%) substrate clearance, reverting back to wildtype levels of 2.6±0.5 and 2.5±0.3, respectively.

Small Intestine Gb3 Analysis

Small intestine showed a much higher accumulation of Gb3 in the GLA-null Fabry mice, exhibiting response ratio of 1164i276, whereas only 3.4±0.3 was detected in the small intestine of wildtype C57BL/6 mice. A single IV dose of the rAAV resulted in a dose-dependent and significant (P<0.01) at all dose levels relative to vehicle-treated GLA-null clearance (FIG. 12). 1×10$^{12}$, 1×10$^{13}$, or 5×10$^{13}$ vg/kg dose levels resulted in 33.6% (772±148), 73% (314i190), and 94.8% (60±59) reduction in Gb3, respectively.

TABLE 7

Summary of Gb3 Reduction in Tissues Collected 56 Days After IV Treatment with rAAV carrying codon optimized GLA

| Group | Genotype | Dose (vg/kg) | Tissue | Response Ratio of Mean Total Gb3 Content | % Reduction from Vehicle-Treated GLA-Null |
|---|---|---|---|---|---|
| 1 | WT | Vehicle | Heart | 2.9 | N/A |
| 2 | GLA-null | Vehicle | Heart | 285.5 | 0% |
| 3 | GLA-null | 1 × 10$^{12}$ | Heart | 30.1 | 89.4% |
| 4 | GLA-null | 1 × 10$^{13}$ | Heart | 9.9 | 96.5% |
| 5 | GLA-null | 5 × 10$^{13}$ | Heart | 4.4 | 98.5% |
| 1 | WT | Vehicle | Kidney | 25.0 | N/A |
| 2 | GLA-null | Vehicle | Kidney | 373.1 | 0% |
| 3 | GLA-null | 1 × 10$^{12}$ | Kidney | 267.4 | 28.3%* |
| 4 | GLA-null | 1 × 10$^{13}$ | Kidney | 95.5 | 74.4% |
| 5 | GLA-null | 5 × 10$^{13}$ | Kidney | 34.6 | 90.7% |
| 1 | WT | Vehicle | Small Intestine | 3.4 | N/A |
| 2 | GLA-null | Vehicle | Small Intestine | 1164.2 | 0% |
| 3 | GLA-null | 1 × 10$^{12}$ | Small Intestine | 772.7 | 33.6% |
| 4 | GLA-null | 1 × 10$^{13}$ | Small Intestine | 313.8 | 73.0% |
| 5 | GLA-null | 5 × 10$^{13}$ | Small Intestine | 60.5 | 94.8% |
| 1 | WT | Vehicle | Liver | 2.9 | N/A |
| 2 | GLA-null | Vehicle | Liver | 377.3 | 0% |
| 3 | GLA-null | 1 × 10$^{12}$ | Liver | 25.9 | 93.1% |
| 4 | GLA-null | 1 × 10$^{13}$ | Liver | 2.6 | 99.3% |
| 5 | GLA-null | 5 × 10$^{13}$ | Liver | 2.5 | 99.3% |

Conclusions

Fabry disease is caused by the accumulation of Gb3 and lysoGb3 substrate molecules in organs and tissues. This study evaluated the ability of a single dose of rAAV carrying codon optimized GLA of SEQ ID NO:1 to express AGA and catabolize Gb3 as a treatment for Fabry disease in a mouse model. The results of this study demonstrate significant reductions in Gb3 and lysoGb3 in plasma and all tissues examined. The low dose of 1×10$^{12}$ vg/kg is highly active in both the heart and liver, leading to a greater than 89% substrate reduction in each organ. The low dose produced a 33.4% substrate reduction in the small intestine, and a reduction in the kidney although the variability seen in the data in the kidney was such that that result did not achieve statistical significance. The mid dose of 1×10$^{13}$ vg/kg yielded more than 96% substrate reduction in the heart, nearly complete (>99%) clearance of the liver, 74.4% reduction in the kidney and 73% reduction of the small intestine and this is a highly active and significant dose in all tissues tested. The high dose of 5×10$^{13}$ vg/kg resulted in greater than 98% substrate clearance in the heart, more than 90% clearance in the kidney, almost 95% clearance in the small intestine, and more than 99% clearance in the liver. All of the doses tested are active and efficacious in the Fabry mouse model and reduced accumulated AGA substrate levels to in some cases at or near wildtype levels.

Example 5—Expression and Functional Analysis of AGA Expressed from Codon Optimized GLA of SEQ ID NO:1 in Plasma and Tissues of Wild Type Mice A single dose non-GLP acute tolerability study of rAAV comprising (i) a capsid with a capsid protein of SEQ ID NO:4 and (ii) a nucleic acid of SEQ ID NO:6, comprising codon-optimized GLA of SEQ ID NO: 1 operably linked to a CAG promoter (4D-310) by intravenous injection in experimentally naive C57BL/6 male mice (8 weeks in age at initiation of dosing) was performed. The maximum tolerated dose (MTD) following a single IV injection (via tail vein) was determined.

The study design is provided at Table 8 below:

TABLE 8

| Group No. | Dose Level (vg/kg) | Dose Volume (mL/kg) | No. of Male Animals |
|---|---|---|---|
| 1 | 0 | 10 | 6 |
| 2 | $1.0 \times 10^{13}$ | 10 | 6 |
| 3 | $5.0 \times 10^{13}$ | 10 | 6 |
| 4 | $1.5 \times 10^{14}$ | 10 | 6 |

Blood samples were collected on Day 1 (predose) and at the same time of day on Days 15, 29 and 43 from all surviving animals via maxillary vessel for determination of GLA activity in plasma.

Postmortem study evaluations were performed on 1 animal euthanized on Day 30 and all surviving animals at the scheduled terminal necropsy (~6 weeks post dose). Heart, liver (left lateral lobe), kidney (left) and small intestine (comparable sized sections of duodenum, ileum and jejunum) were isolated from all animals and evaluated for GLA activity.

Figure 13:
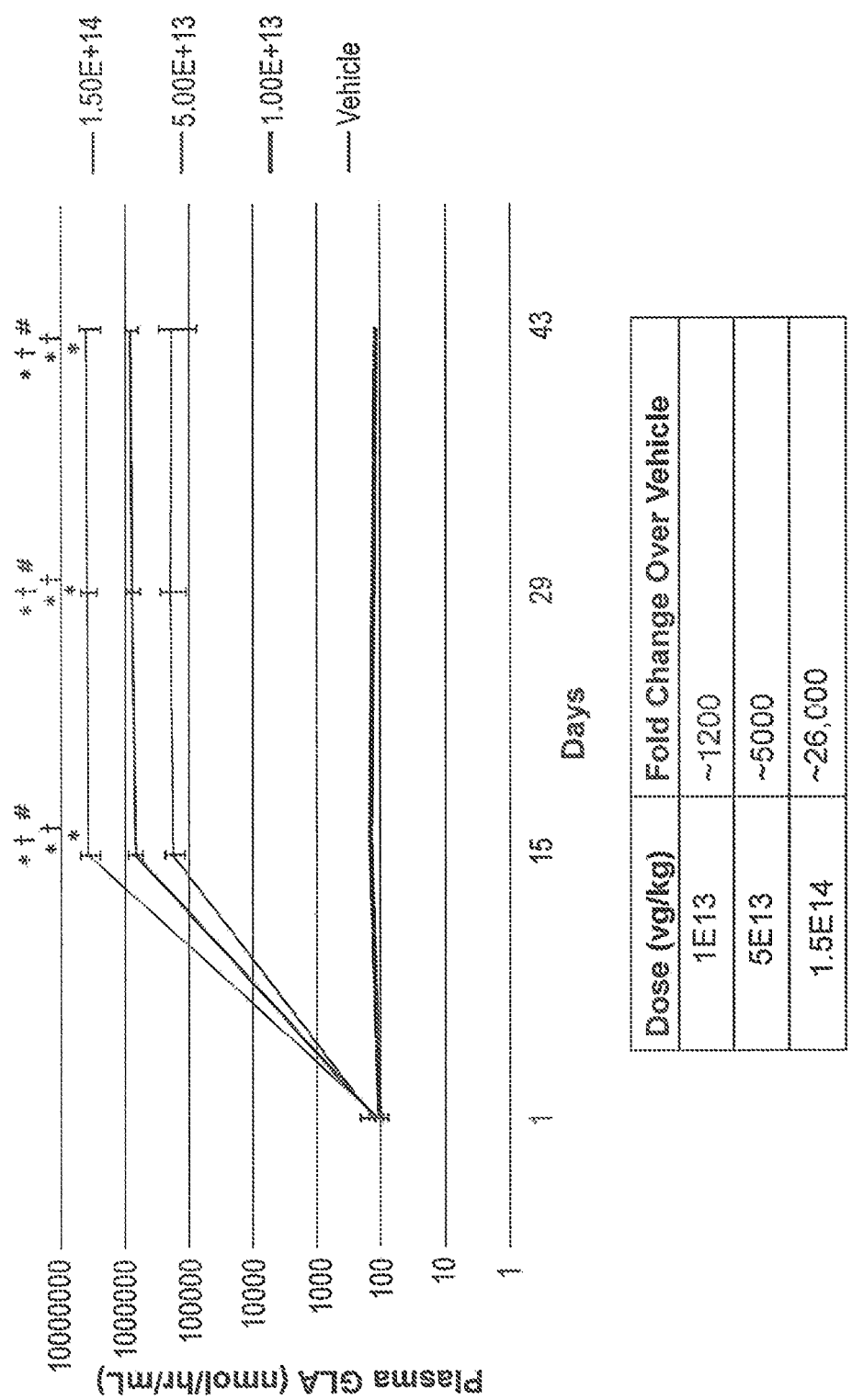
FIG. 13 graphically describes GLA activity in plasma of wild type C57BL/6 mice following a single intravenous administration of 4D-310 (rAAV comprising (i) a capsid with a capsid protein of SEQ ID NO:4 and (ii) a nucleic acid comprising a nucleotide sequence of SEQ ID NO:6) at each of the specified doses.
Figure 14:
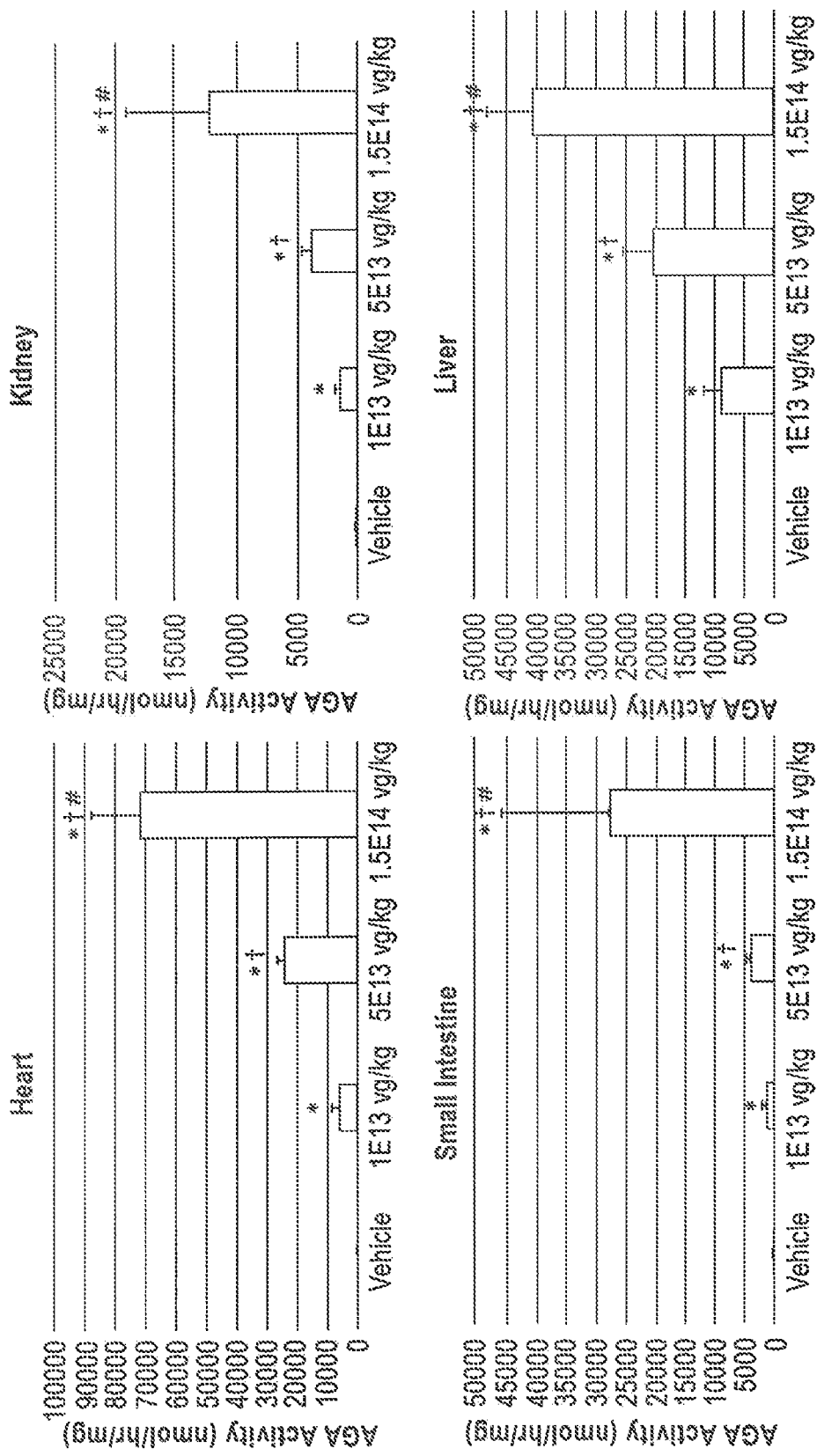
FIG. 14 graphically describes GLA activity in specified tissues of wild type C57BL/6 mice following a single intravenous administration of 4D-310 (rAAV comprising (i) a capsid with a capsid protein of SEQ ID NO:4 and (ii) a nucleic acid comprising a nucleotide sequence of SEQ ID NO:6) at each of the specified doses.

Following dosing, all treated plasma samples had GLA activity significantly above that of control animals (see FIG. 13, illustrating a 1200-fold increase over vehicle control for the $1.0 \times 10^{13}$ vg/kg dose, a 5000-fold increase over vehicle control for the $5.0 \times 10^{13}$ vg/kg dose and a 26,000-fold increase over vehicle control for the $1.5 \times 10^{14}$ vg/kg dose). In addition, each higher dose had plasma GLA activity significantly above the lower dose(s). The same trends (dose responsiveness) were observed in all collected tissues (see FIG. 14). Taken collectively, the data demonstrate a clear expression of GLA and resultant GLA activity following a single IV dose of 4D-310 at each dose. Notably, duodenum, heart, ileum, jejunum, heart, kidney, and liver tissues are among the most relevant tissues for treatment of Fabry disease, with expression of GLA in the liver serving as a GLA bioreactor.

A summary of GLA values in the plasma of 4D-310-treated animals is provided in Table 9 below:

TABLE 9

| Dose (vg/kg) | Sample Type | Day 1 | Day 15 | Day 29 | Day 43 |
|---|---|---|---|---|---|
| | | (plasma, nmol/hr/mL) | | | |
| 0 | Plasma | 85.18 | 114.33 | 109.33 | 100.72 |
| $1.0 \times 10^{13}$ | | 113.43 | $134116.67^b$ | $148983.33^b$ | $136833.33^b$ |
| $5.0 \times 10^{13}$ | | 100.43 | $549500.00^{b,d}$ | $600000.00^{b,d}$ | $637000.00^{b,d}$ |
| $1.5 \times 10^{14}$ | | 91.03 | $3211666.67^{b,d,f}$ | $2980000.00^{b,d,f}$ | $3023333.33^{b,d,f}$ |
| | | (tissues, nmol/hr/mg) | | | |
| 0 | Duodenum | — | — | — | 397.67 |
| $1.0 \times 10^{13}$ | | — | — | — | $1646.33^b$ |
| $5.0 \times 10^{13}$ | | — | — | — | $4188.00^{b,d}$ |
| $1.5 \times 10^{14}$ | | — | — | — | $27883.33^{b,d,f}$ |
| 0 | Heart | — | — | — | 146.67 |
| $1.0 \times 10^{13}$ | | — | — | — | $6246.67^b$ |
| $5.0 \times 10^{13}$ | | — | — | — | $24380.00^{b,d}$ |
| $1.5 \times 10^{14}$ | | — | — | — | $71833.33^{b,d,f}$ |
| 0 | Ileum | — | — | — | 432.75 |
| $1.0 \times 10^{13}$ | | — | — | — | $2253.33^b$ |
| $5.0 \times 10^{13}$ | | — | — | — | $13450.00^{b,d}$ |
| $1.5 \times 10^{14}$ | | — | — | — | $39466.67^{b,d,f}$ |
| 0 | Jejunum | — | — | — | 366.33 |
| $1.0 \times 10^{13}$ | | — | — | — | $2471.50^b$ |
| $5.0 \times 10^{13}$ | | — | — | — | $6564.00^{b,c}$ |
| $1.5 \times 10^{14}$ | | — | — | — | $26783.33^{b,d,f}$ |
| 0 | Kidney | — | — | — | 132.67 |
| $1.0 \times 10^{13}$ | | — | — | — | $1389.17^b$ |
| $5.0 \times 10^{13}$ | | — | — | — | $3828.00^{b,d}$ |
| $1.5 \times 10^{14}$ | | — | — | — | $12356.67^{b,d,f}$ |
| 0 | Liver | — | — | — | 282.00 |
| $1.0 \times 10^{13}$ | | — | — | — | $86816.67^b$ |
| $5.0 \times 10^{13}$ | | — | — | — | $2020000.00^{b,d}$ |
| $1.5 \times 10^{14}$ | | — | — | — | $401333.33^{b,d,f}$ |

—Not Applicable
[b] different from 0 vg/kg, p < 0.01
[c] different from $1.0 \times 10^{13}$ vg/kg p < 0.05
[d] different from $1.0 \times 10^{13}$ vg/kg p < 0.01
[f] different from $5.0 \times 10^{13}$ vg/kg p < 0.01

There were no 4D-310-related macroscopic observations in the study. There were no 4D-310-related clinical observations of systemic or local toxicity in the study, nor were any 4D-310-related changes in body weight or effects on food consumption observed. There were no 4D-310 related mortalities in the study.

As there were no adverse 4D-310 related effects on any of the evaluated parameters following a single intravenous dose at $1.0\times10^{13}$, $5\times10^{13}$ and $1.5\times10^{14}$ vg/kg to male mice, the no-observed-effect-level (NOEL) and maximum tolerated dose was determined to be $1.5\times10^{14}$ vg/kg, the highest dose tested.

Example 6—Toxicity and Biodistribution of Systemically Administered 4D-310 (Comprising a Nucleic Acid with Codon Optimized GLA of SEQ ID NO:11

Potential toxicity and tissue biodistribution of 4D-310, administered to C57BL/6 (wt) mice via a single intravenous injection via tail vein followed by a 14-day and 91- or 92-day observation period was investigated. The study design is provided in Table 10 below:

TABLE 10

| Group No. | Dose Level (vg/kg) | Dose Volume (mL/kg) | No. of Male Animals | |
|---|---|---|---|---|
| | | | Day 15 Necropsy[a] | Day 92 +/− 1 Necropsy[a] |
| 1 | 0 | 10 | 22 + 2[b] | 22 + 2[b] |
| 2 | $1.0\times10^{13}$ | 10 | 22 + 2[b] | 22 + 2[b] |
| 3 | $5.0\times10^{13}$ | 10 | 22 + 2[b] | 22 + 2[b] |
| 4 | $1.5\times10^{14}$ | 10 | 22 + 2[b] | 22 + 2[b] |

[a]On each day of necropsy, animals were designated as follows: 5/group for clinical chemistry parameters and microscopic examinations; 5/group for hematology parameters; 5/group for anti-capsid and anti-payload anti-drug antibody analyses; 7/group for GLA activity analysis and tissue and whole blood qPCR and RT-qPCR.
[b]Additional animals/treatment group were dosed as possible replacements. If not used as replacements, the additional animals were euthanized and discarded at the Day 92 ± 1 interval.

The following parameters and endpoints were evaluated in this study: mortality, clinical observations, body weight, and food consumption, ophthalmoscopic examinations, clinical pathology parameters (hematology and clinical chemistry), anti-capsid and anti-payload antidrug antibody analyses, GLA activity analysis, biodistribution analysis (tissue and whole blood qPCR and RT-qPCR), gross necropsy findings, organ weights, and histopathologic examinations.

There were no 4D-310-related mortalities or clinical signs of systemic or direct local toxicity, nor any effects on body weight, food consumption, ophthalmoscopic examinations, clinical pathology parameters, organ weights, or gross necropsy findings.

All 4D-310 (which comprises the 4D-C102 capsid protein of SEQ ID NO:4) treated animals screened positive for anti-4D-C102 capsid antibodies based on being above the determined screening cut-point. However, even though all 4D-310 treated animals screened positive; only 16/30 samples were confirmed positive following the evaluation against the confirmatory cut-point. These 16 confirmed positive samples had the following dose level breakdown: 7/10 at $1.0\times10^{13}$ vg/kg, 5/10 at $5.0\times10^{13}$ vg/kg, and 4/10 at $1.5\times10^{14}$ vg/kg. There was no apparent dose relationship to the anti-capsid antibody response A proportion of animals developed anti-capsid antibodies in the study following dosing with 4D-310, however there was no dose-relationship apparent. All control animals were screened and confirmed to be negative for anti-4D-C102 capsid antibodies. 4D-310 treatment did not result in anti-alpha Galactosidase A antibodies being formed as all treated animals were found to be negative. Treatment with 4D-310 yielded a dose dependent and statistically significant increase in plasma GLA activity that was present throughout the duration of the study when compared to the control group. Most treated groups were also higher than the previous dose group in a statistically significant manner.

Among the highest levels of vector genomes observed for both doses and timepoints are heart, liver, lung, kidney and injection site. The concentration of 4D-310 vector DNA detected in the Brain and Spinal Cord in all groups was overall lower compared to the previously mentioned tissues. Similar to the biodistribution analysis, where the highest levels of 4D-310 vector DNA was detected in the liver samples, vector derived gene expression was observed at the highest concentrations in the liver samples, followed by the heart, lung, and injection site samples.

Within the liver samples, 4D-310 expression was approximately 14× greater at 645,293,620 copies per μg of total RNA compared to the heart samples with at 44,662,881 copies per μg of total RNA. The testis samples exhibited an abnormally increased level of gene expression at an average of 2,888,001 copies per μg of total RNA compared only 1,884 copies of 4D-310 vector DNA detected in the biodistribution analysis at the same timepoint and dose level. This can be attributed directly to Animal 4043, where 4D-310 expression was 15,095,299 copies versus an average of only 446,541 copies between the other 5 animals. In addition, Animal 4043 only had an individual count of 1,443 copies of 4D-310 vector DNA detected during biodistribution analysis and had no clinical/veterinary findings throughout the duration of the study. Therefore, the abnormally high level of gene expression was considered non-adverse as there was no impact to the overall health of the animal.

Overall vector-derived 4D-310 gene expression was noted in all tissues with the highest concentrations noted in the liver, heart, lung, and injection site samples. There were no 4D-310 macroscopic findings. There were no 4D-310-related microscopic findings with the exception of minimal to mild injection site perivascular/vascular inflammation at ≥$5.0\times1013$ vg/kg. This finding was not present in the Day 92±1 animals and was considered reversible.

A summary of the mean copies per μg of tissue vector DNA is summarized in Table 11 below.

TABLE 11

| TISSUE | Vehicle-Day 15 | Low Dose-Day 15 | High Dose-Day 15 | High Dose Day-92/93 |
|---|---|---|---|---|
| Brain, Cerebrum | 0 | 2,886.20 | 21,176.88 | 17,799.26 |
| Brain, Cerebellum | 29.56 | 2,657.93 | 13,488.98 | 18,107.84 |
| Dorsal Root Ganglia (DRG) | 0 | 709.87 | 6,138.45 | 1,847.41 |
| Epididymis | 0 | 521.96 | 7,207.75 | 2,930.27 |
| Heart | 8.38 | 19,243.03 | 81,560.75 | 61,892.67 |
| Injection Site | 0 | 224,576.42 | 3,989,305.62 | 850,106.33 |
| Kidney Left | 0 | 6,932.66 | 85,867.02 | 28,735.23 |
| Liver | 0 | 425,413.55 | 6,798,453.78 | 3,379,680.04 |
| Lung with Bronchi | 0 | 85,046.08 | 340,084.19 | 246,525.53 |
| Lymph Node, Mandibular | 0 | 1,703.21 | 12,431.13 | 3,621.43 |
| Lymph Node, Mesenteric | 0 | 1,786.74 | 13,209.12 | 4,528.63 |
| Sciatic Nerve | 0 | 1,304.78 | 15,593.00 | 6,724.72 |

TABLE 11-continued

| TISSUE | Vehicle-Day 15 | Low Dose-Day 15 | High Dose-Day 15 | High Dose Day-92/93 |
|---|---|---|---|---|
| Seminal Vesicles Left | 0 | 240.72 | 1,845.50 | 1,149.30 |
| Spinal Cord | 429.92 | 2,888.00 | 22,941.23 | 21,961.64 |
| Spleen | 0 | 16,851.98 | 237,296.48 | 10,989.76 |
| Testis | 7.14 | 508.36 | 4,745.76 | 1,884.38 |
| Whole Blood | 0 | — | 208,234.43 | 146.80 |
| Bone Marrow | 0 | 140.94 | 5,641.30 | 790.94 |

BLOD = Below Limit of Quantitation, 9.97 Copies/reaction
BLOQ = Below Lower Limit of Quantitation, 50 copies/reaction
N/A = Total DNA Concentration (µg/µL) is ≤ 0
— = No samples available for analysis.
Note:
Individual BLOD results were reported as "0" and Individual BLOQ results were reported as "50" for the calculation of the mean copy number; N/A results are not included in the mean copy number Similar to the biodistribution analysis, where the highest levels of 4D-3J0 vector DNA was detected in the liver samples, vector derived gene expression was observed at the highest concentrations in the liver samples, followed by the heart, lung, and injection site samples. Within the liver samples, 4D-310 expression was approximately 14× greater at 645,293,620 copies per µg of total RNA compared to the heart samples with at 44,662,881 copies per µg of total RNA.

Overall vector-derived 4D-310 gene expression was noted in all tissues with the highest concentrations noted in the liver, heart, lung, and injection site samples. A summary of the mean copies per µg of tissue vector RNA is summarized in Table 12 below.

TABLE 12

| TISSUE | High Dose Day-92/93 |
|---|---|
| Brain, Cerebrum | 913,078.68 |
| Brain, Cerebellum | 741,324.07 |
| Dorsal Root Ganglia (DRG) | N/A |
| Heart | 44,662,881.13 |
| Injection Site | 12,798,244.57 |
| Kidney | 278,022.32 |
| Liver | 645,293,620.04 |
| Lung with Bronchi | 15,668,829.48 |
| Spinal Cord | 252,581.65 |
| Spleen | 510,369.25 |
| Testis | 2,888,000.80 |

BLOD = Below Limit of Quantitation, 57.34 copies/reaction
BLOQ = Below Lower Limit of Quantitation, 500 copies/reaction
N/A = Total RNA Concentration (µg/µL) is ≤ 0
Note:
individual BLOD results were reported as "0" and individual BLOQ results were reported as "500" for the calculation of the mean copy number; N/A results are not included in the mean copy number In conclusion, following a single intravenous administration of 4D-310, no adverse effects were noted in any parameter evaluated. As a result, the No-Observed-Adverse-Effect-Level (NOAEL) for local and systemic toxicity was $1.5 \times^{14}$ vg/kg, the highest dose level tested.

Example 7—Study on IV Dosing of 4D-310 to Non-Human Primates

Toxicity, pharmacodynamics and biodistribution of 4D-310 and 4D-C102.CAG-EGFP (an rAAV having the same capsid as 4D-310 and a heterologous nucleic acid encoding EGFP operably linked to a CAG promoter) was assessed in cynomolgus monkeys following a single intravenous (infusion) dose prior to human clinical trials. The study design is shown in Table 13 below:

TABLE 13

| Cohort | Group | N | Treatment | Route | Dose (vg/kg) | In-Life | Immune Suppression | Endpoints |
|---|---|---|---|---|---|---|---|---|
| 1 | 2 | 3 | 4D-310 | IV | 3e12 | 8 wks | Drug: | In-Life |
|  | 3 | 3 | 4D-310 | IV | 1e13 | 8 wks | Methylprednisolone | Cageside |
|  | 4 | 3 | 4D-310 | IV | 5e13 | 8 wks | Dosing: IM q.w. | observations (2x daily) |
| 2 | 1 | 1 | Vehicle | IV | N/A | 8 wks | Dose Levels: | Food consumption (2x daily) |
|  | 5 | 3 | C102.EG FP | IV | 5e13 | 8 wks | 40 mg/kg: | Detailed Clinical |
|  |  |  |  |  |  |  | Day −15 to 28 | Observations (weekly) |
|  |  |  |  |  |  |  | 20 mg/kg: | Body weights (weekly) |
|  |  |  |  |  |  |  | Day 29 to 42 | Hematology |
|  |  |  |  |  |  |  | 10 mg/kg: | (Week 1, 2, 4, 6, EOS) |
|  |  |  |  |  |  |  | Day 43 to 56 | Clinical chem |
|  |  |  |  |  |  |  |  | (Week 1, 2, 4, 6, EOS) |
|  |  |  |  |  |  |  |  | Plasma AGA activity |
|  |  |  |  |  |  |  |  | (pre-dose, Week 2, 4, 6, EOS) |
|  |  |  |  |  |  |  |  | After sacrifice: |
|  |  |  |  |  |  |  |  | Tissues (primary): |
|  |  |  |  |  |  |  |  | Heart |
|  |  |  |  |  |  |  |  | Liver |
|  |  |  |  |  |  |  |  | Kidney |
|  |  |  |  |  |  |  |  | Small Intestines |
|  |  |  |  |  |  |  |  | AGA activity |
|  |  |  |  |  |  |  |  | Histopathology |
|  |  |  |  |  |  |  |  | Immunohistochemistry for AGA |
|  |  |  |  |  |  |  |  | qPCR (biodistribution) |
|  |  |  |  |  |  |  |  | RT-qPCR (transgene expression) |

Cynomolgus monkeys were administered either of two different transgenes: GLA (of SEQ ID NO:1) (Groups 2-4) or EGFP (Group 5), each comprised within an rAAV capsid comprising a capsid protein of SEQ ID NO:4, or single vehicle control (Group 1). A remarkably clean safety profile was observed with 4D-310 (comprising the codon optimized GLA of SEQ ID NO: 1 and capsid of SEQ ID NO:4)-treated animals. Transaminitis was observed only in EGFP-dosed animals.

All animals were administered an immunosuppressant beginning two weeks prior to test article administration through study termination. This suppression regimen was intended to be aligned with clinical practice. Briefly, from Day −15 through Day 28, methylprednisolone acetate (40 mg/kg) was administered once weekly via intramuscular injection to all animals in Groups 2, 3, and 4. The dose was halved to 20 mg/kg on Days 29 through 42 and halved again to 10 mg/kg on Days 43 through 56.

Immunosuppression dosing was not required the week of scheduled terminal necropsy. From Day −14 through 29, methylprednisolone acetate (40 mg/kg) was administered once weekly via IM injection to all animals in Groups 1 and 5. Immunosuppression was increased (to a max of 80 mg/kg/week) or decreased at the discretion of the study veterinarian. On Day 16, one Group 5 male received an additional dose (40 mg/kg).

The vehicle and test articles were administered once during the study via IV infusion at dose levels of 0 (vehicle), $3.0\times10^{12}$, $1.0\times10^{13}$, $5.0\times10^{13}$ vg/kg for 4D-310 and $5.0\times10^{13}$ vg/kg for 4D-C102.CAG.EGFP and administered at a rate of 3 mL/minute. The first day of dosing was designated as Day 1 for each individual animal.

The IV route is the intended route of administration of 4D-310 in human subjects. The dose levels were selected based on separate dose ranging safety/efficacy studies in mice in which doses from $1\times10^{12}$ vg/kg to $1.5\times10^{14}$ vg/kg were all shown to be safe.

For GLA plasma sample collection, blood samples (approximately 3 mL) were collected from all animals via the femoral vein for GLA analysis according to the schedule at Table 14 below:

TABLE 14

| | Sample Collection Time Points | | | | |
|---|---|---|---|---|---|
| Group No. | Day 1 (predose) | Day 15 | Day 29 | Day 43 | Day of Necropsy |
| 1-4 | X | X | X | X | X |

X = sample collected

For anti-AAV evaluation, blood samples (approximately 5 mL) were collected from all animals via femoral vein according to the schedule at Table 15 below:

TABLE 15

| | Sample Collection Time Points | | | | | |
|---|---|---|---|---|---|---|
| Group No. | Day 1 (predose) | Day 8 | Day 15 | Day 29 | Day 43 | Day of Necropsy |
| 1-4 | X | X | X | X | X | X |

X = sample collected

Tissue samples for qPCR analysis (100 to 180 mg for each tissue sample except spleen (50-80 mg/sample) were collected and split into 2 samples and snap-frozen liquid nitrogen and stored frozen until analyzed. DNA tissue collection and evaluation was according to Table 16 below:

TABLE 16

| Tissue[a] | Region | Groups 2-4 DNA 1 (GLA) | Group 1 DNA 1 (GLA) | Group 5 DNA 2 (GFP) |
|---|---|---|---|---|
| Blood vessel | Aorta | 1 | 1 | 1 |
| | Carotid | 1 | 1 | 1 |
| | Pulmonary Artery | — | — | 1 |
| Brain[b] | Left Hemisphere | 1 | 1 | 1 |
| | Right Hemisphere | 1 | 1 | 1 |
| | Brain Stem | 1 | 1 | 1 |
| | Cerebellum | 1 | 1 | 1 |
| Dorsal Root Ganglia | Thoracic | — | — | — |
| | All remaining (L) | 1 | 1 | 1 |
| | All remaining (R) | — | — | — |
| Nerve | Sciatic Nerve | 1 | 1 | 1 |
| Heart | Left Ventricular Free Wall | 2 | 2 | 2 |
| | Left Atrium | 1 | 1 | 1 |
| | Right Ventricle | 1 | 1 | 1 |
| | Right Atrium | 1 | 1 | 1 |
| | Ventricular Septum | 1 | 1 | 1 |
| Kidney | Right Kidney | 1 | 1 | 1 |
| | Left Kidney | 1 | 1 | 1 |
| Liver | Right Lobe | 1 | 1 | 1 |
| | Left Lobe | 1 | 1 | 1 |
| Lung | | 2 | 2 | 2 |
| Skeletal Muscle | Deltoid (p) | 1 | 1 | 1 |
| | Deltoid (d) | 1 | 1 | 1 |
| | Diaphragm (L) | 1 | 1 | 1 |
| | Diaphragm (R) | 1 | 1 | 1 |
| | Latissimus Dorsi (L) | — | — | 1 |
| | Latissimus Dorsi (R) | — | — | 1 |
| | Pectoralis Major (p) | 1 | 1 | 1 |
| | Pectoralis Major (d) | 1 | 1 | 1 |
| | Tibialis Anterior (p) | — | 1 | 1 |
| | Tibialis Anterior (d) | — | 1 | 1 |
| | Triceps Brachii (p) | 1 | 1 | 1 |
| | Triceps Brachii (d) | 1 | 1 | 1 |
| | Bicep Femoris (p) | 1 | 1 | 1 |
| | Bicep Femoris (d) | 1 | 1 | 1 |
| | Tongue | — | — | — |
| Small Intestine | Jejunum | 1 | 1 | 1 |
| | Duodenum | — | — | 1 |
| | Ileum | — | — | 1 |
| Spinal Cord | Cervical | 1 | 1 | 1 |
| | Thoracic | 1 | 1 | 1 |
| | Lumbar | 1 | 1 | 1 |
| Testes | Left | 1 | 1 | 1 |
| | Right | — | — | 1 |

[a]In the event of insufficient organ/tissue to complete all collections, priority were placed on the primary samples for DNA analysis
[b]The standard Bolen et al., 2013 blocking scheme was followed for both hemispheres (2 sets of standard blocks). Only the right hemisphere was processed to slide for microscopic evaluation.
(p) = proximal; (d) = distal; (L) = Left side; (R) = right side.

The DNA 1 tissues from Groups 1 through 4 were analyzed for vector biodistribution by qPCR. The DNA 2 tissues from Group 5 were analyzed for vector biodistribution by qPCR.

Tissue samples for RT-qPCR analysis (100 to 180 mg for each tissue sample, when available) to determine gene expression of 4D-310 in various Cynomolgus monkey tissues were collected and split into 2 samples according to Table 17 below:

TABLE 17

| Tissue[a] | Region | Groups 2-4 RNA 1 (GLA) | Group 1 RNA 1 (GLA) | Group 5 RNA 2 (GFP) |
|---|---|---|---|---|
| Blood vessel | Aorta | 1 | 1 | 1 |
| | Carotid | 1 | 1 | 1 |
| | Pulmonary Artery | — | — | 1 |
| Brain[b] | Left Hemisphere | 1 | 1 | 1 |
| | Right Hemisphere | 1 | 1 | 1 |
| | Brain Stem | 1 | 1 | 1 |
| | Cerebellum | 1 | 1 | 1 |
| Dorsal Root Ganglia | Thoracic | — | — | — |
| | All remaining (L) | — | — | — |
| | All remaining (R) | 1 | 1 | 1 |
| Nerve | Sciatic Nerve | 1 | 1 | 1 |
| Heart | Left Ventricular Free Wall | 2 | 2 | 2 |
| | Left Atrium | — | — | — |
| | Right Ventricle | 1 | 1 | 1 |
| | Right Atrium | — | — | — |
| | Ventricular Septum | 1 | 1 | 1 |
| Kidney | Right Kidney | 1 | 1 | 1 |
| | Left Kidney | 1 | 1 | 1 |
| Liver | Right Lobe | 1 | 1 | 1 |
| | Left Lobe | 1 | 1 | 1 |
| | Lung | 2 | 2 | 2 |
| Skeletal Muscle | Deltoid (p) | 1 | 1 | 1 |
| | Deltoid (d) | 1 | 1 | 1 |
| | Diaphragm (L) | 1 | 1 | 1 |
| | Diaphragm (R) | 1 | 1 | 1 |
| | Latissimus Dorsi (L) | — | — | 1 |
| | Latissimus Dorsi (R) | — | — | 1 |
| | Pectoralis Major (p) | 1 | 1 | 1 |
| | Pectoralis Major (d) | 1 | 1 | 1 |
| | Tibialis Anterior (p) | — | 1 | 1 |
| | Tibialis Anterior (d) | — | 1 | 1 |
| | Triceps Brachii (p) | 1 | 1 | 1 |
| | Triceps Brachii (d) | 1 | 1 | 1 |
| | Bicep Femoris (p) | 1 | 1 | 1 |
| | Bicep Femoris (d) | 1 | 1 | 1 |
| | Tongue | — | — | 1 |
| Small Intestine | Jejunum | 1 | 1 | 1 |
| | Duodenum | — | — | 1 |
| | Ileum | — | — | 1 |
| Spinal Cord | Cervical | 1 | 1 | 1 |
| | Thoracic | 1 | 1 | 1 |
| | Lumbar | 1 | 1 | 1 |
| Testes | Left | 1 | 1 | — |
| | Right | — | — | — |

[a]In the event of insufficient organ/tissue to complete all collections, priority will be placed on the primary samples for IHC, Protein, DNA, and RNA analyses
[b]The standard Bolon et al., 2013 blocking scheme will be followed for both hemispheres (2 sets of standard blocks). Only the right hemisphere will be processed to slide for microscopic evaluation.
(p) = proximal; (d) = distal; (L) = Left side; (R) = right side.

RNA was extracted from the tissue samples, quantified and then analyzed by RT-qPCR for the detection and quantification of RNA sequence specific to 4D-310. Briefly, samples collected for RT-qPCR analysis were completely immersed into labeled 2-mL microfuge cryogenic tubes prefilled with 1.5 mL RNALater. Samples were placed on wet ice, stored refrigerated (2° C. to 8° C.) for at least 24 hours up to 1 week in the RNALater, and then stored frozen (−60° C. to −90° C.) with the RNALater removed until gene expression analysis (RT qPCR). All DNA 1 samples from animals in Groups 1-4 were shipped on dry ice to Covance Laboratories, Greenfield, Indiana for analysis. All DNA 2 samples from Group 5 were transferred to the bioanalytical laboratory at the Testing Facility for analysis.

The RNA 1 tissues from Groups 1 through 4 were analyzed for GLA gene expression by RT-qPCR. The RNA 2 tissues from Group 5 were analyzed for GFP gene expression by RT-qPCR.

Protein tissue collection—Samples (100 to 180 mg for each tissue sample, when available) were flash frozen in liquid nitrogen (LN2) and stored frozen (−60° C. to −90° C.). The Protein 1 tissues were analyzed for GLA activity according to Table 18 below:

TABLE 18

| Tissue[a] | Region | Groups 2-4 Protein 1 (GLA) | Group 1 Protein 1 (GLA) | Group 1 Protein 1 (GFP) | Group 5 Protein 2 (GFP) |
|---|---|---|---|---|---|
| Blood vessel | Aorta | 1 | 1 | 1 | 1 |
| | Carotid | 1 | 1 | 1 | 1 |
| | Pulmonary Artery | — | — | — | — |
| Brain[b] | Left Hemisphere | 1 | 1 | 1 | 1 |
| | Right Hemisphere | 1 | 1 | 1 | 1 |
| | Brain Stem | 1 | 1 | 1 | 1 |
| | Cerebellum | 1 | 1 | 1 | 1 |
| Nerve | Sciatic Nerve | 1 | 1 | 1 | 1 |
| Heart | Left Ventricular Free Wall | 2 | 2 | 2 | 2 |
| | Left Atrium | | | | |
| | Right Ventricle | 1 | 1 | 1 | 1 |
| | Right Atrium | — | — | — | — |
| | Ventricular Septum | 1 | | | 1 |
| Kidney | Right Kidney | 1 | 1 | 1 | 1 |
| | Left Kidney | 1 | 1 | 1 | 1 |
| Liver | Right Lobe | 1 | 1 | 1 | 1 |
| | Left Lobe | 1 | 1 | 1 | 1 |
| | Lung | 2 | 2 | 2 | 2 |
| Skeletal Muscle | Deltoid (p) | 1 | 1 | 1 | 1 |
| | Deltoid (d) | 1 | 1 | 1 | 1 |
| | Diaphragm (L) | 1 | 1 | 1 | 1 |
| | Diaphragm (R) | 1 | 1 | 1 | 1 |

TABLE 18-continued

| Tissue[a] | Region | Groups 2-4 Protein 1 (GLA) | Group 1 Protein 1 (GLA) | Group 5 Protein 1 (GFP) | Protein 2 (GFP) |
|---|---|---|---|---|---|
| | Latissimus Dorsi (L) | — | — | 1 | 1 |
| | Latissimus Dorsi (R) | — | — | 1 | 1 |
| | Pectoralis Major (p) | 1 | 1 | 1 | 1 |
| | Pectoralis Major (d) | 1 | 1 | 1 | 1 |
| | Tibialis Anterior (p) | — | 1 | 1 | 1 |
| | Tibialis Anterior (d) | — | 1 | 1 | 1 |
| | Triceps Brachii (p) | 1 | 1 | 1 | 1 |
| | Triceps Brachii (d) | 1 | 1 | 1 | 1 |
| | Bicep Femoris (p) | 1 | 1 | 1 | 1 |
| | Bicep Femoris (d) | 1 | 1 | 1 | 1 |
| | Tongue | — | — | 1 | 1 |
| Small Intestine | Jejunum | 1 | 1 | 1 | 1 |
| | Duodenum | — | — | 1 | 1 |
| | Ileum | — | — | 1 | 1 |
| Spinal Cord | Cervical | 1 | 1 | 1 | 1 |
| | Thoracic | 1 | 1 | 1 | 1 |
| | Lumbar | 1 | 1 | 1 | 1 |
| Testes | Left | — | — | — | — |
| | Right | 1 | 1 | — | — |

[a] In the event of insufficient organ/tissue to complete all collections, priority were placed on the primary samples for IHC, Protein, DNA, and RNA analyses.
[b] The standard Bolon et al., 2013 blocking scheme were followed for both hemispheres (2 sets of standard blocks). Only the right hemisphere were processed to slide for microscopic evaluation (p) = proximal; (d) = distal; (L) = Left side; (R) = right side The Protein 2 tissues were analyzed for GFP by ELISA.

For histology and immunohistochemistry (IHC), samples of each specified tissue were collected and processed. Samples were fixed in neutral buffered formalin for 24 to 48 hours, transferred to 70% EtOH as needed for up to 72 hours, and processed to the block stage for histology and IHC. Efforts were made to preserve the morphology/anatomical integrity of the tissues. A subset of formalin-fixed, paraffin-embedded blocks from each designated tissue were shipped to the Sponsor. Slides were prepared and stained for IHC evaluations.

The Anti-Galactosidase alpha (GLA) Immunohistochemistry (IHC) assay was performed using recombinant rabbit anti-human monoclonal Anti-Galactosidase alpha antibody (Abcam clone EP5858, catalog #ab168341) at a final concentration of 10 ug/mL diluted in Roche Discovery antibody RUO (catalog #05266319001). GLA IHC was performed on the Roche Discovery ULTRA autostainer platform using Roche Discovery ChromoMap DAB RUO (catalog #05266645001), Roche Discovery Anti-Rabbit HQ RUO (catalog #07017812001) and Roche Discovery Anti-HQ HRP RUO (catalog #07017936001) detection reagents.

GLA IHC assay antigen retrieval was performed at 100° C. for 32 minutes using Roche Cell Conditioning 1 (CC1) antigen retrieval solution (catalog #950-124). GLA IHC primary antibody and rabbit IgG isotype control antibody (Cell Signaling Technology Rabbit (DA1E) mAb IgG XP Isotype control catalog #3900) were incubated at room temperature for 32 minutes. GLA IHC assay secondary antibody and HRP polymer detection reagents were each incubated at room temperature for 16 minutes. Slides were counterstained at room temperature using Roche Hematoxylin for 8 minutes (catalog #05266726001) and Roche Bluing Reagent for 8 minutes (catalog #05266769001). After removal from the Roche Discovery ULTRA instrument, slides are rinsed in DI water with Dawn liquid soap to remove residual oil. GLA IHC slides are then dehydrated through graded ethanols/xylenes and coverslipped using Leica XL and CV5030 stainer/coverslipper instruments. GLA IHC slides were then converted to high resolution whole slide images using Mikroscan SL2 instrument and associated Q2 imaging software. GLA IHC slides were evaluated by a board-certified pathologist. Representative images were captured using QuPath and ImageScope software.

The following parameters and endpoints were evaluated in this study: mortality, clinical signs, body weights, body weight changes, ophthalmology examinations, clinical pathology parameters (hematology, coagulation, and clinical chemistry), gross necropsy findings, organ weights, and histopathologic examinations. In addition, DNA (qPCR), RNA (RT-qPCR) and protein (plasma and/or tissue) distribution for enhanced green fluorescent protein (EGFP) and alpha-galactosidase A (GLA) were conducted to evaluate the biodistribution and relative gene expression efficiency of the test articles. Exploratory immunohistochemistry (IHC) evaluations were also conducted.

Results

Mortality—all animals survived to the scheduled necropsy.

Detailed clinical/veterinary observations—There were no clear 4D-310 or 4D-C102.CAG-EGFP-related clinical signs.

Body Weight and Body Weight Gains—There were no 4D-310 or 4D-C102.CAG-EGFP-related changes in body weight or body weight gain. Slight increases and/or decreases were observed in animals from all groups during the treatment period and were considered to be within normal variation for this species.

Ophthalmology Examinations—There were no 4D-310 or 4D-C102.CAG-EGFP-related effects noted in the ophthalmoscopic examinations. Observations noted were representative of pathology that would be expected for animals of this age and species and are not considered test article-related.

Hematology—There were no 4D-310 or 4D-C102.CAG-EGFP-related effects on hematology endpoints at any dose level.

Coagulation—There were no apparent 4D-C102.CAG-EGFP-related effects on coagulation endpoints.

qPCR GLA (DNA)_Biodistribution Analysis

The quantity of 4D-310 vector DNA present in each sample was calculated from the average of the two unspiked replicates analyzed with qPCR. Results are reported as copies of 4D-310 present per g of DNA analyzed (adjusted for any dilution factors and concentrations below 0.2 µg/µL). Group 1 is a vehicle/control group. All the tested samples from the vehicle treated animal (Animal ID 1001) were found to be <LOD (limit of detection) for GLA DNA. Among animals administered $3.0\times10^{12}$ vg/kg 4D-310, GLA DNA was detected positive, ranging from 51.72 (Jejunum of Animal 2003) to 6,309,088.75 (Liver, Right Lobe of Animal 2002) copies per µg of total DNA for all tested tissue samples except for the samples mentioned below. Testes, Left of Animals 2001 and 2003, and Spinal Cord, Lumbar of Animals 2002 and 2003 were found to be <LOQ. No result to report for Heart, Left Atrium of Animal 2002 due to no remaining tissue available. Result for Carotid of Animal 2002 was obtained by analyzing the DNA from the failed extraction run upon sponsor's request. Among animals administered $1.0\times10^{13}$ vg/kg 4D-310, GLA DNA was found as positive in all tested tissue samples. The testing results obtained range from 178.65 (Jejunum of Animal 3002) to 3,379,109.30 (Liver, Left Lobe of Animal 3001) copies per g of total DNA. The original testing results of Liver. Right Lobe and Liver, Left Lobe of Animals 3002 and 3003 were found to be >ULOQ (upper limit of quantification), DNA extracted from these tissue samples were retested with further 1:10 dilution performed.

Figure 15:
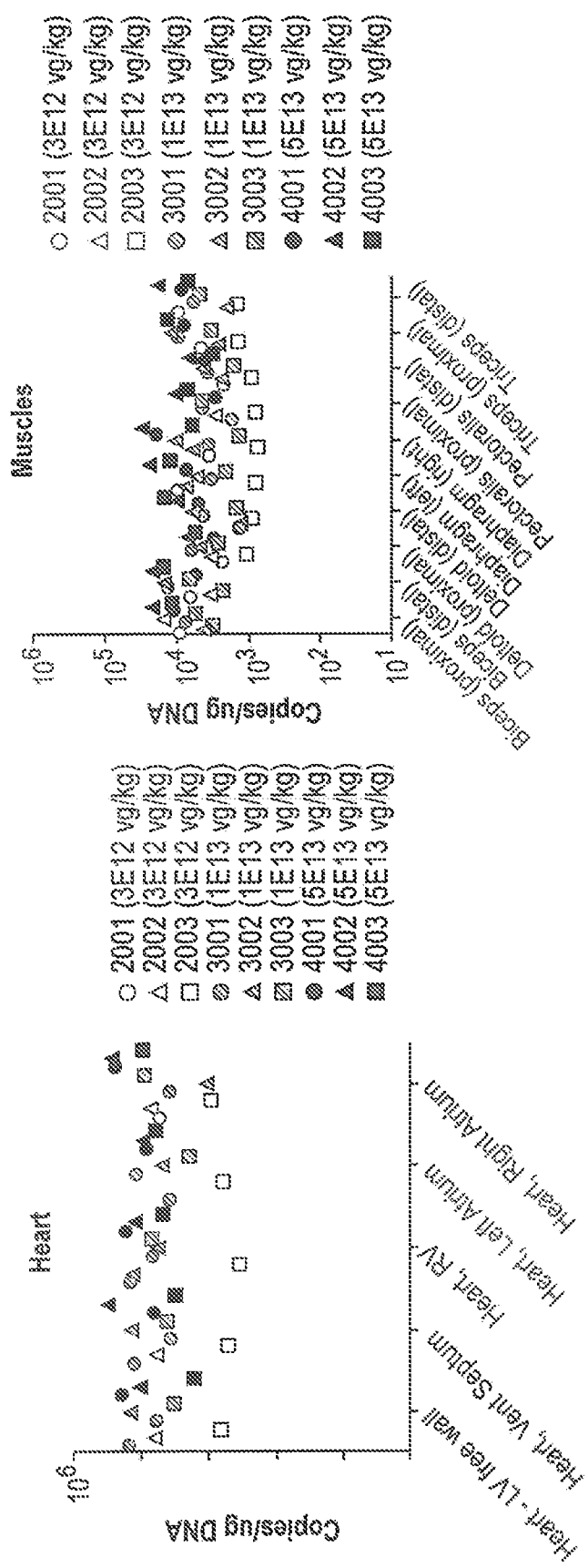
FIG. 15 illustrates biodistribution of 4D-310 (by qPCR) to key Fabry tissues following a single intravenous administration of the specified dose of 4D-310, vehicle control or C102.EGFP (rAAV comprising a capsid comprising a capsid protein of SEQ ID NO:4 and a nucleic acid encoding EGFP) to non-human primates.

Among animals administered $5.0 \times 10^{13}$ vg/kg 4D-310, GLA DNA was found as positive in all tested tissue samples. The testing results obtained range from 168.86 (Testes of Animal 4003) to 21,116,311.46 (Liver, Right Lobe of Animal 4001) copies per μg of total DNA. The original testing results of Liver, Right Lobe and Liver Left Lobe of Animals 4001, 4002 and 4003 were all found to be >ULOQ. DNA extracted from these tissue samples were retested with further 1:50 (for 4001), 1:20 (for 4002) and 1:25 (for 4003) dilution performed.

qPCR distribution of 4D-310 to key Fabry tissues following IV administration of $3 \times 10^{12}$ vg/kg to the non-human primates is shown at FIG. 15, with dose responsive biodistribution to the liver achieved. These data demonstrate that 4D-310 delivered IV successfully localizes to key tissues of Fabry disease pathology, including the heart and kidneys. These data are also supportive of dose responsive expression in the liver as a target for systemic expression of soluble therapeutic protein.

GLA Plasma Quantification

A total of 50 plasma samples from animals administered $3.0 \times 10^{12}$ to $5.0 \times 10^{13}$ vg/kg 4D-310 on Days 1 (predose), 15, 29, 43 and the day of necropsy were analyzed for GLA activity using a qualified method. The results from calibration standards and quality control samples demonstrated acceptable performance of the method for all reported concentrations.

GLA levels were comparable across all animals prior to dosing (Day 1). By Day 15, plasma GLA levels increased in 1 of 3 animals at $3.0 \times 10^{12}$ vg/kg 4D-310 (up to 23.6×), 3 of 3 animals at $1.0 \times 10^{13}$ vg/kg 4D-310 (up to 8.1×) and 3 of 3 animals at $5.0 \times 10^{13}$ vg/kg 4D-310 (up to 152.2×). Plasma GLA levels were generally similar (within approximately 2.5-fold of the Day 15 value) from Day 15 through the day of necropsy. This data is summarized below:

| Group | 4D-310 Dose Level (vg/kg) | Day | Fold-change from control |
|---|---|---|---|
| 2 | $3.0 \times 10^{12}$ | 1 (predose) | — |
|  |  | 15 | 23.6× |
|  |  | 29 | 25.6× |
|  |  | 43 | 42.3× |
|  |  | Day of necropsy | 20.9× |
| 3 | $1.0 \times 10^{13}$ | 1 (predose) | — |
|  |  | 15 | 5.2-8.1× |
|  |  | 29 | 2.0-5.6× |
|  |  | 43 | 2.5-5.3× |
|  |  | Day of necropsy | 2.3-6.3× |
| 4 | $5.0 \times 10^{13}$ | 1 (predose) | — |
|  |  | 15 | 26.5-152.2× |
|  |  | 29 | 19.2-65.7× |
|  |  | 43 | 15.9-70.9× |
|  |  | Day of necropsy | 19.7-73.4× |

Figure 16:
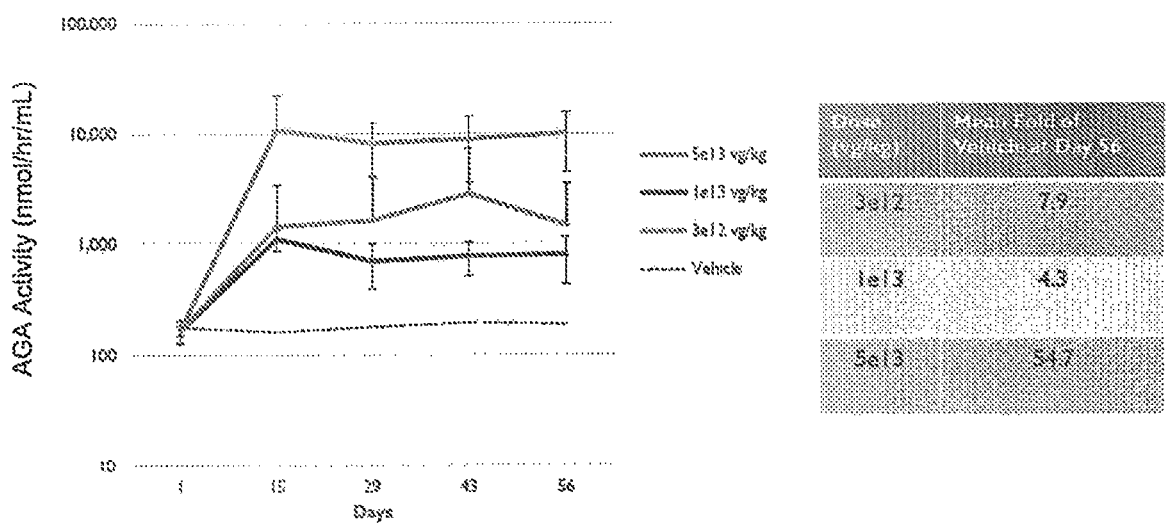
FIG. 16 illustrates AGA in NHP plasma, arranged by dosage, after a single intravenous administration of 4D-310 at each of the specified doses.

FIG. 16 depicts AGA in NHP plasma after a single intravenous dose of 4D-310, grouped by dose (a 54.7-fold increase in plasma AGA level was observed in the $5.0 \times 10^{11}$ vg/kg dose relative to vehicle-treated control). High AGA level in animal #2002 caused the low dose group mean to be higher than the mid dose group mean. Otherwise a dose-dependency was observed. Delivery of 4D-310 at all dose groups evaluated resulted in plasma AGA levels above endogenous AGA levels (vehicle), which demonstrates successful gene delivery and gene expression from the 4D-310 product.

Figure 17:
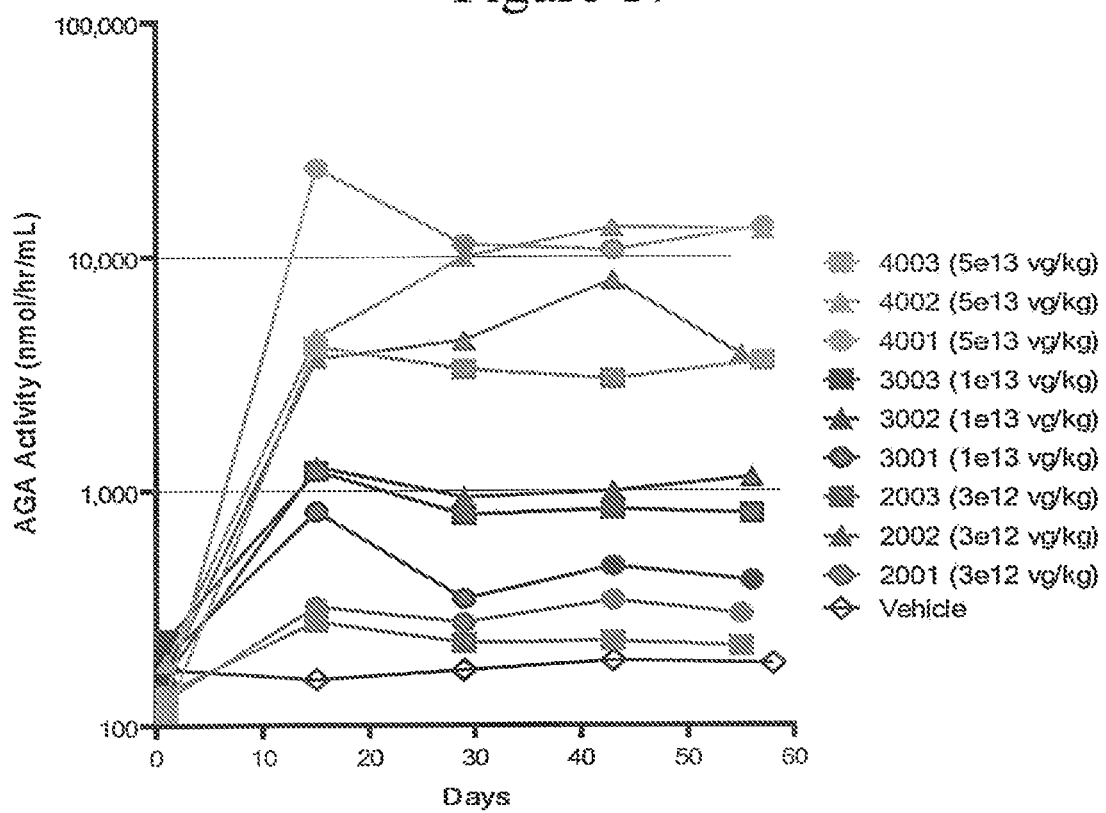
FIG. 17 illustrates AGA in NHP plasma, arranged by animal, after a single intravenous administration of 4D-310 at each of the specified doses

FIG. 17 depicts plasma AGA levels in individual animals after a single intravenous dose of 4D-310. Animal 2002 has unexpectedly high plasma AGA activity—this animal has high DNA, RNA, and protein in the liver. Delivery of 4D-310 resulted in plasma AGA levels above endogenous AGA levels (vehicle) for all individual animals, which demonstrates successful gene delivery and gene expression from the 4D-310 product.

GLA Protein Tissue Biodistribution Analysis

The Anti-Galactosidase alpha (GLA) Immunohistochemistry (IHC) assay was developed by screening multiple commercially available GLA antibodies with a matrix of assay conditions including antigen retrieval conditions, primary antibody and detection conditions in formalin fixed paraffin embedded (FFPE) cell pellets and tissues. Specificity and sensitivity of GLA IHC assay was determined by evaluation of wild type HEK293T and 4D-310 transfected HEK293T cells and 4D-310 treated Fabry mouse tissues.

4D-310 treated formalin fixed paraffin embedded (FFPE) non-human primate (NHP) tissue samples were evaluated for GLA IHC expression. Control cell pellets were included in each experimental run for quality control and to ensure consistent results between runs. Rabbit IgG Isotype antibody controls were included for each tissue sample to ensure specificity of GLA IC assay.

Low level endogenous GLA expression was observed in vehicle treated tissues. An increase in GLA THC expression was observed in 4D-310 treated NHP cardiac tissues at all dose levels ($3 \times 10^{12}$, $1 \times 10^{13}$ and $5 \times 10^{13}$). An increase in GLA expression was observed in 4D-310 treated NHP liver tissues only at $5 \times 10^{13}$ dose level. Detection at the lower dose levels by IHC was potentially confounded by high endogenous liver expression, based on the expression seen in the vehicle-treated animal, No increase in GLA IHC staining was observed in NHP skeletal muscle, diaphragm, kidney, aorta, carotid artery or small intestine tissue samples. Results were verified and cell types identified by an external, board-certified pathologist.

At study termination in animals administered 4D-310, increases in GLA expression to the vehicle control were limited to the liver, carotid artery, heart (including left ventricular free wall and left atrium), lung, aorta, a subset of skeletal muscles (including deltoid, pectoralis major and diaphragm), kidney and brain (left hemisphere). The greatest expression of GLA were seen in the liver (up to 21.1×), carotid artery (up to 15.5×), left ventricular free wall (up to 12.2×), and lung (up to 10.1×). A lower level of GLA expression (<10×) was noted in the aorta (up to 7.4×), deltoid (up to 4.3×) diaphragm (up to 3.7×), pectoralis major (up to 3.4×), kidney (2.5×), bicep femoris (2.5×), brain (up to 2.4×), left atrium (2.2×). Elevation in GLA was occasionally, though not always, dose responsive. These changes were considered 4D-310-related. All other tissues were less than 2× of control and therefore were not considered to have elevated GLA expression. A summary of relative GLA tissue expression from animals administered 4D-310 can be found at Table 19 below:

TABLE 19

| Tissue | Incidence by Dose Level (fold-change from control) | | |
|---|---|---|---|
| | $3.0 \times 10^{12}$ vg/kg | $1.0 \times 10^{13}$ vg/kg | $5.0 \times 10^{13}$ vg/kg |
| Liver | 3 of 3 (3.0-11.5x) | 3 of 3 (2.0-7.2x) | 3 of 3 (4.6-21.1) |
| Carotid | 0 of 3 | 2 of 3 (3.9-15.5x) | 1 of 3 (4.2x) |
| Left ventricular free wall (a + b) | 1 of 3 (2.0x) | 1 of 3 (2.0-3.2x) | 3 of 3 (2.0-12.2x) |
| Lung | 0 of 3 | 1 of 3 (3.7x) | 2 of 3 (2.5-10.1x) |
| Aorta | 1 of 3 (2x) | 3 of 3 (2.3-7.4x) | 2 of 3 (2.0-2.4x) |
| Deltoid (proximal and distal) | 0 of 3 | 2 of 3 (2.1-4.3x) | 0 of 3 |
| Diaphragm (left and right) | 3 of 3 (2.0-3.7x) | 2 of 3 (2.3-2.8x) | 3 of 3 (2.2-3.6x) |
| Pectoralis Major (proximal and distal) | 2 of 3 (2.0-3.4x) | 2 of 3 (2.2-3.0x) | 3 of 3 (2.1-2.6x) |
| Bicep femoris | 0 of 3 | 0 of 3 | 1 of 3 (2.5x) |
| Kidney | 0 of 3 | 0 of 3 | 1 of 3 (2.5x) |
| Left atrium | 0 of 3 | 0 of 3 | 1 of 3 (2.2x) |
| Brain (left and right hemisphere) | 0 of 3 | 1 of 3 (2.4x) | 1 of 3 (2.1x) |

Figure 18:
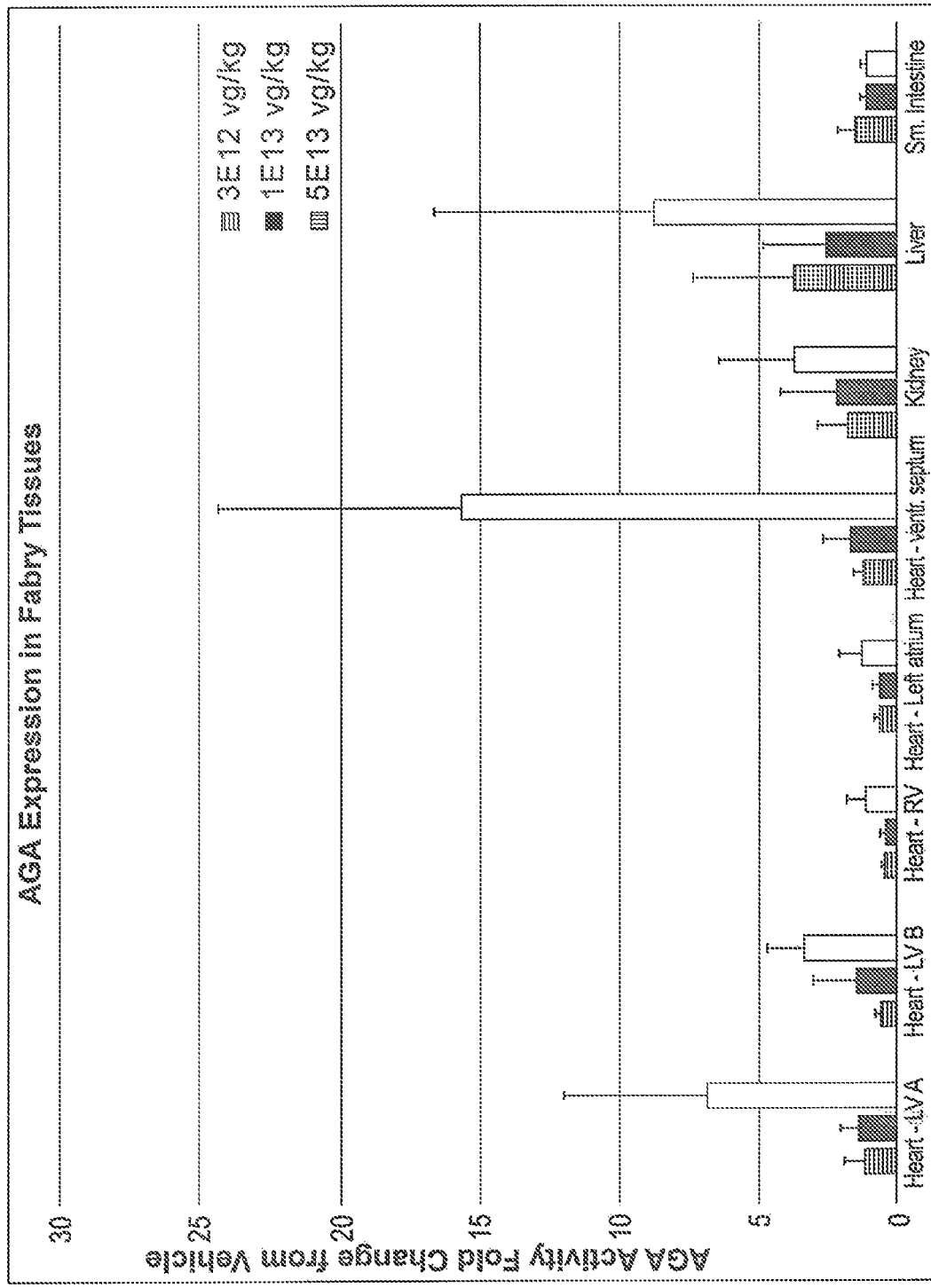
FIG. 18 illustrates fold-change in AGA (relative to vehicle control) in Fabry-relevant NHP tissues, arranged by dosage, after a single intravenous administration of 4D-310 at each of the specified doses
Figure 19:
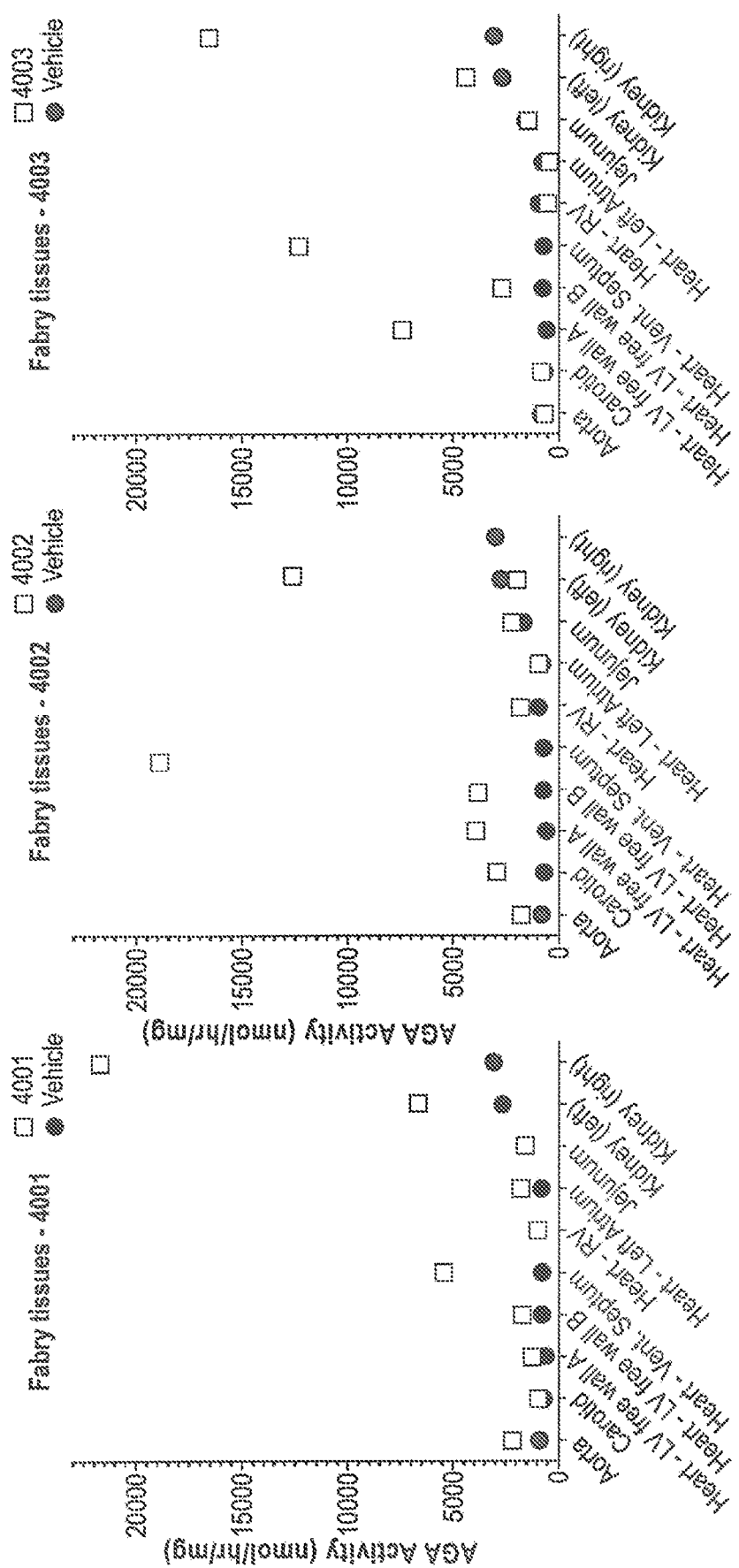
FIG. 19 illustrates fold-change in AGA (relative to vehicle control) in Fabry-relevant NHP tissues, arranged by animal, after a single intravenous administration of 4D-310 at the $5 \times 10^{13}$ vg/kg dose.

As can be seen from FIGS. 18-19, intravenous delivery of 4D-310 to NHPs resulted in a significant increase in AGA expression in Fabry-relevant tissues compared to control NHPs treated with vehicle only. Delivery of 4D-310 thus resulted in successful gene delivery and gene expression from the 4D-310 product in therapeutically relevant tissues. Elevated AGA expression is shown in the heart in the high dose animals (FIG. 19).

RT-qPCR (RNA) Gene Expression Analysis

All samples tested from Group 1 (vehicle/control) animal were found to be <LOD for 4D-310 as expected.

Among the Group 2 animals (that received $3.0 \times 10^{12}$ vg/kg of 4D-310), 4D-310 RNA was detected positive, ranging from 630.68 (Testes, Left of Animal 2001) to 19,744,452.23 (Liver, Left Lobe of Animal 2002) copies per µg of total RNA for all tested tissue samples except for the following samples: (1) Deltoid Distal, Diaphragm Left, Diaphragm right, Pectoralis Major and Biceps Femoris Distal and Brain Cerebellum, Jejunum, Carotid, Spinal Cord Thoracic, Spinal Cord Lumbar and Lung of Animal 2001 were found to be <LOD (2) Brain, Brainstem of Animal 2001 was found to be <LOQ (3) Deltoid Distal and Biceps Femoris Distal of Animals 2002 were found to be <LOD (4) Deltoid Proximal, Pectoralis Major Proximal, Biceps Femoris Proximal, Jejunum, DRG All remaining Right and Spinal Cord Thoracic of Animals 2002 were found to be <LOQ (5) Diaphragm Left, Diaphragm Right, Pectoralis Major Proximal, Pectoralis Major Distal, Biceps Femoris Distal, Sciatic Nerve and Spinal Cord Lumbar of Animal 2003 were found to be <LOD (6) Deltoid Proximal, Biceps Femoris Proximal, Brain Right Hemisphere, Brain Cerebellum, DRG All remaining Right and Testes Left of Animal 2003 were found to be <LOQ. No copies per µg of total RNA result to report for Sciatic Nerve and Spinal Cord Lumbar of Animal 2002 due to the negative Total RNA concentration measured for these samples.

Among the Group 3 animals (that received $1.0 \times 10^{13}$ vg/kg of 4D-310), 4D-310 RNA was found as positive in all tested tissue samples. The testing results obtained range from 765.27 (Jejunum of Animal 3003) to 10,387,886.08 (Aorta of Animal 3002) copies per µg of total RNA of all tested tissue samples except for the following: (1) Deltoid Proximal, Deltoid Distal, Diaphragm Left, Pectoralis Major Proximal, Pectoralis Major Distal, Triceps Branchii Proximal, Triceps Branchii Distal, Biceps Femoris Proximal, Biceps Femoris Distal, Sciatic Nerve and Spinal Cord Lumbar of Animal 3001 were found to be <LOD (2) Diaphragm Right of Animal 3001 had no copies/jig of RNA result available (3) Brain, Brainstem and Lung of Animal 3001 were found to be <LOQ (4) Diaphragm Right, Pectoralis Major Proximal, Jejunum, Sciatic Nerve, Lung and Spinal Cord Lumbar of Animal 3002 were found to be <LOD (5) Biceps Femoris Distal and Brain Brainstem of Animal 3002 were found to be <LOQ (6) DRG All remaining Right of Animal 3003 was found to be <LOQ.

Among the Group 4 animals (that received $5.0 \times 10^{13}$ vg/kg of 4D-310), 4D-310 RNA was found as positive in all tested tissue samples. The testing results obtained range from 930.51 (Triceps Branchii, Proximal of Animal 4001) to 127,602,838.22 (Heart, Ventricular Septum of Animal 4002) copies per µg of total RNA except for the following: (1) Brain Cerebellum, Jejunum and Sciatic Nerve of Animal 4001 were found to be <LOD (2) Carotid for Animal 4001 was found to be <LOQ (3) Brain Left Hemisphere, Brain Right Hemisphere, Brain Brainstem, DRG All remaining Right and Lung of Animal 4001 had negative total RNA concentration and therefore no copies/µg RNA result is available for these samples (4) Diaphragm Left and Biceps Femoris Proximal of Animal 4002 were found to be <LOD (5) Jejunum and Sciatic Nerve of Animal 4002 were found to be <LOQ (6) Biceps Femoris Distal and Sciatic Nerve of Animal 4003 were found to be <LOD (7) Deltoid Proximal, Pectoralis Major Proximal and Jejunum of Animal 4003 were found to be <LOQ.

The bridging assessment to identify differences, if any, between the use of manually purified RNA samples and those purified using the QIAcube HT system demonstrated that both methods yielded similar results with no effect on the precision or accuracy of the method. The inter-assay precision between the different QC types, yielded Qty % CV values between 2% and 20% for all QC levels, while the inter-assay accuracy Qty % RE results ranged from −6% to −2% across all QC concentrations.

Approximately 52 days following intravenous infusion, the tissues exhibiting the highest levels of vector derived gene expression were the left ventricular free wall and ventricular septum heart samples, the left and right liver lobes, the carotid blood vessel, and right ventricle heart samples. The left ventricular free wall and ventricular septum heart samples yielded an average of $5.48 \times 10^3$ and $5.46 \times 10^3$ copies per 10 ng of total RNA analyzed, while the average concentration across all 6 liver samples was $3.59 \times 10^3$ copies. The carotid blood vessel and right ventricle heart samples yielded $3.33 \times 10^3$ and $1.78 \times 10^3$ copies respectively. A majority of the remaining tissue samples yielded minimal to no vector derived gene expression with more than ¾ of the samples testing at or below the limit or quantitation. Stark contrasts are evident when comparing the biodistribution results, which test just for the presence of the viral vector, with the gene expression results. From the biodistribution data, the levels of vector detected in the liver samples were more than 60x greater at $5.75 \times 10^6$ copies per µg of sample DNA compared to $8.69 \times 10^4$ copies for the left ventricular free wall samples and $9.12 \times 10^4$ copies from the ventricular septum samples. Conversely, the levels of gene expression observed were approximately 1.5x higher in the 2 heart samples compared to the liver samples. The carotid blood vessel and right ventricle heart samples showed similar results with vector levels ~128x and ~69x higher in the liver samples, while the gene expression levels were approximately equal between the blood vessel and liver samples and only 2x higher in the liver samples versus the right ventricle heart samples. Vector DNA was detected in the untranscribed liver samples of all animals. This contamination of the vector DNA would account for approximately 1% to 12% of the target sequence gene expression. Vector contamination was not detected in any of the remaining samples analyzed. The expression levels of the housekeeping gene, Hprt1, was consistent across the individual tissues of each animal confirming the overall integrity of the RNA samples.

Figure 20:
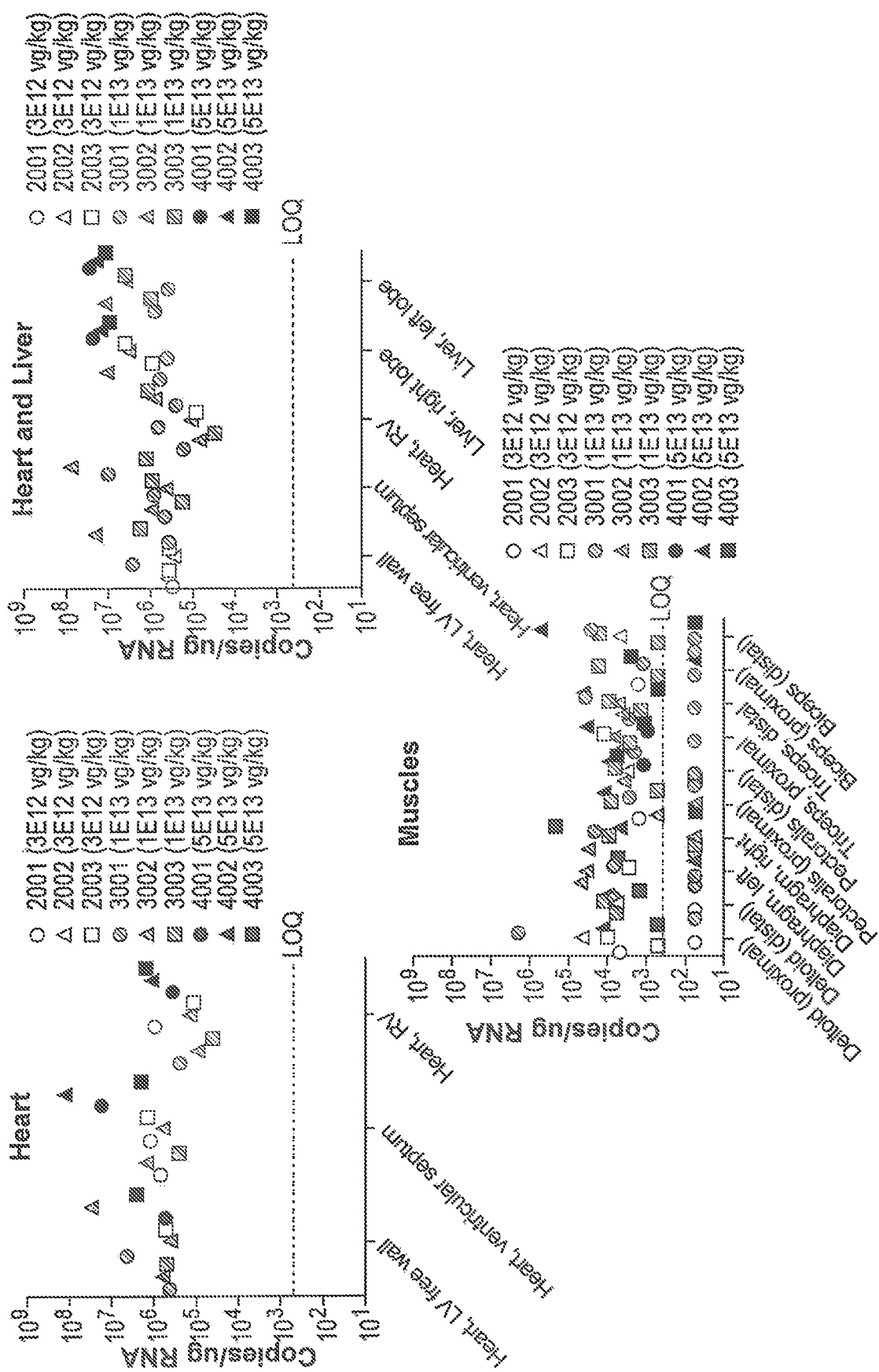
FIG. 20 illustrates biodistribution of GLA RNA expression (by RT-qPCR) following a single intravenous administration of the specified dose of 4D-310 to non-human primates.
Figure 21A:
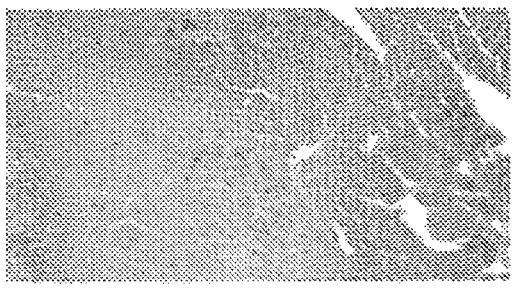
FIGS. 21A-B IHC detection of AGA in heart tissue of vehicle-treated or 4D-310-treated NHPs after a single IV administration at the $5 \times 10^{13}$ vg/kg dose.
Figure 21A:
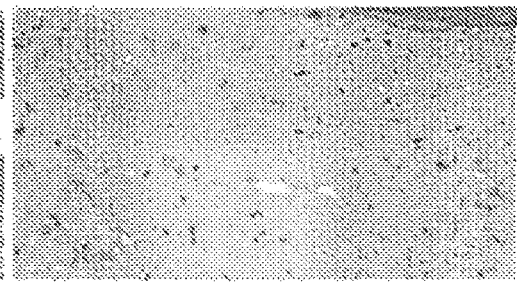
Figure 21A:
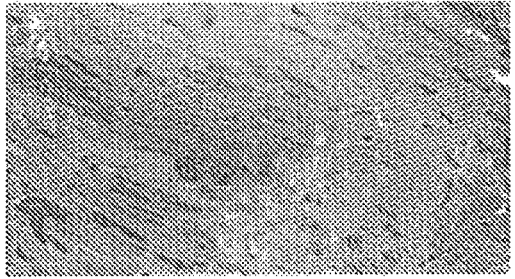
Figure 21A:
Figure 21B:
Figure 21B:
Figure 21B:
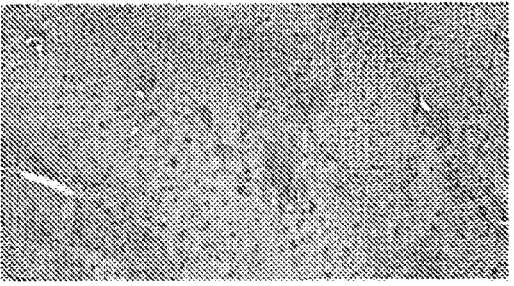
Figure 21B:
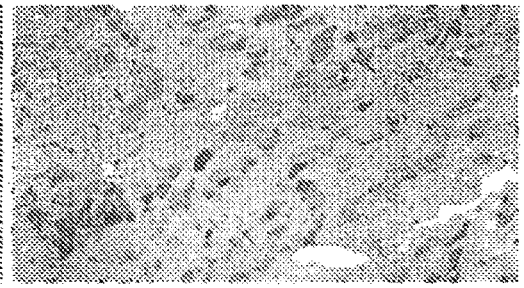
Figure 22A:
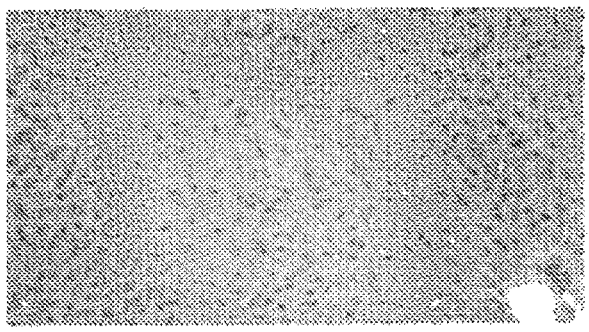
FIGS. 22A-B IHC detection of AGA in liver (FIG. 22A) and kidney (FIG. 22B) tissues of vehicle-treated or 4D-310-treated NHPs after a single IV administration at the $5 \times 10^{13}$ vg/kg dose. Upregulation of AGA activity in treated animals over a high endogenous level in the vehicle animal is shown.
Figure 22A:
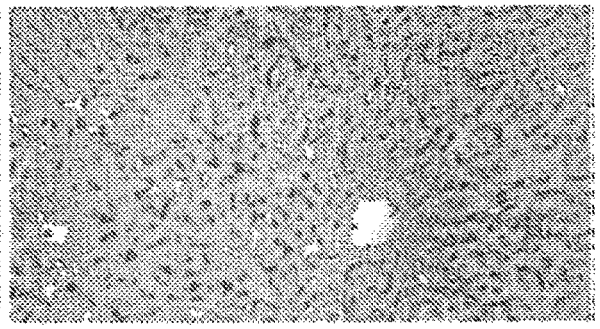
Figure 22A:
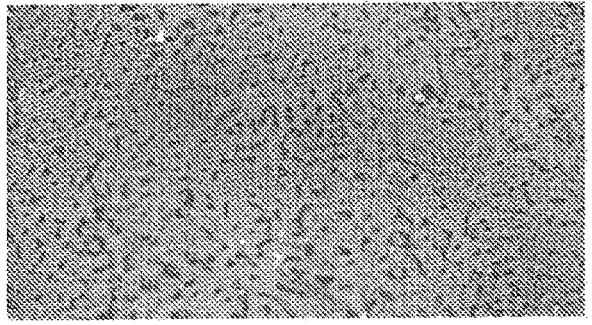
Figure 22A:
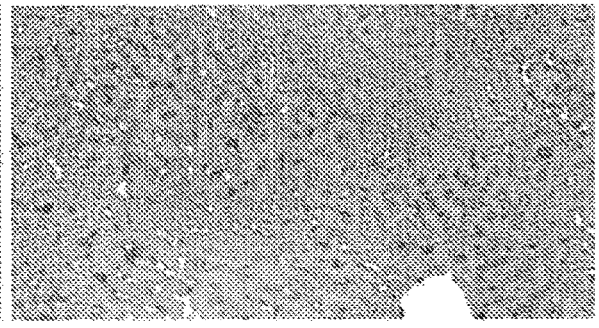
Figure 22B:
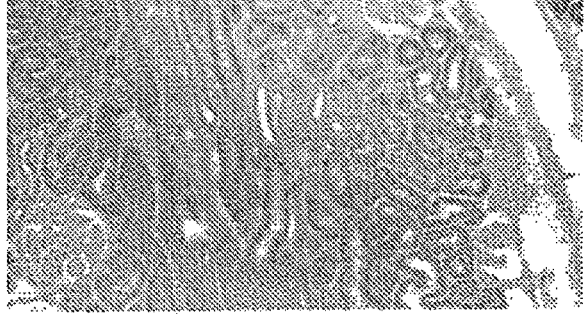
Figure 22B:
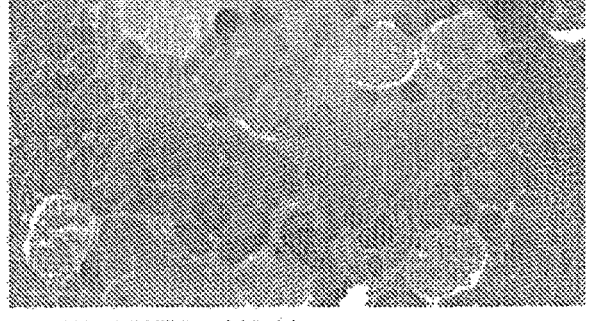
Figure 22B:
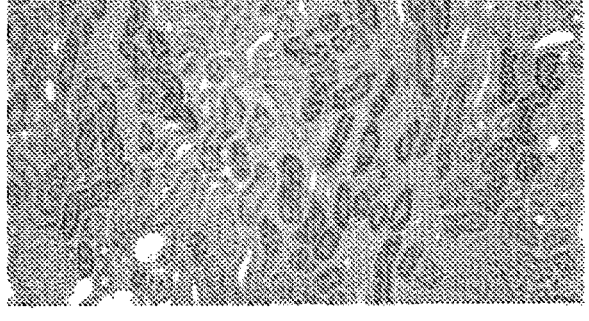
Figure 22B:
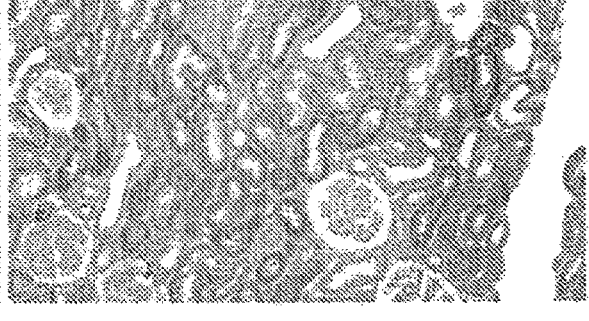

As can be seen from FIG. 20, a single intravenous administration of each of the specified doses of 4D-310 to NHPs results in GLA RNA expression with consistent expression observed in the heart and liver, both key organs for treating Fabry disease.

Gross Pathology

There were no 4D-310 or 4D-C102.CAG-EGFP-related macroscopic findings. Macroscopic findings in all test article animals given 4D-C102.CAG-EGFP at $5.0\times10^{13}$ and the single vehicle control animal consisted of white foreign material in the quadriceps (bilateral or unilateral). One of the animals (Animal No. 5003) given 4D-C102.CAG-EGFP also had a unilateral abscess in the quadriceps. These were presumably procedure related as they occurred in the control and 4D-C102.CAG-EGFP-treated animals. One animal given the low dose of 4D-310 at $3.0\times10^{12}$ (Animal No. 2002) had edema of the subcutis in the right hindleg/limb. The later change was likely not directly test article related as it was a unilateral localized change. Macroscopic changes were not evaluated microscopically as per protocol.

Histopathology

There were no clear 4D-310 or 4D-C102.CAG-EGFP-related microscopic findings. Several findings occurred in tissues of animals with no clear test article relationship. Findings noted in the 4D-310 and 4D-C102.CAG-EGFP-treated animals and the vehicle control consisted of minimal infiltrates of mononuclear cells in adventitia of various tissues including heart, various skeletal muscles, and sciatic nerve. Additionally, minimal mononuclear infiltrates occurred in the meninges of the brain of 4D-310-treated animals, but not in 4D-C102.CAG-EGFP treated or the vehicle control animals. Other findings noted in 4D-310 treated monkeys included minimal myofiber degeneration or regeneration in various skeletal muscles (typically focal), minimal alveolar macrophage aggregates in the lung, and minimal (multifocal) vacuolation of hepatocytes. These were typically of low incidence with no dose related trend in incidence, distribution, or severity. Furthermore, these minimal changes can occur as background findings for the species and thus were not considered test article related. None of these findings are considered adverse. Fat necrosis occurred in the adipose tissue of various tissues of 4D-310-treated animals including the heart coronary groove, aorta adventitia, and skeletal muscle adventitia with no clear dose relationship in incidence or severity. Severity was minimal to moderate and was not dose related. Fat necrosis has been noted as a consequence of high dose methylprednisolone treatment in our laboratory or can be noted as an incidental background change. Methylprednisolone treatment was used to control immunogenic response of the test articles.

Autophagy of nerve cell bodies (cytoplasmic rarefaction) of scattered neurons was noted in the dorsal root ganglia of one animal at each dose of 4D-310. Severity was minimal to mild but was not dose related. This change is a background finding in Cynomolgus monkeys (Butt M. et al., 2019) (Pardo I. et al., 2019) and is not considered test article related. All other microscopic observations were considered incidental and not test article related. These observations are known background findings for the species, were of low incidence, were of similar incidence and severity for control and test article-treated animals, and/or had no dose response relationship.

Toxicology—Changes related to IV administration of 4D-310 or 4D-C102.CAG-EGFP were limited to effects on clinical pathology. Following a single IV dose of $5.0\times10^{13}$ vg/kg 4D-310 and 4D-C102.CAG-EGFP, there were minimal to marked, respectively, increases in alanine aminotransferase (ALT) activities. In animals administered 4D-C102.CAG-EGFP, there were concurrent minimal to moderate increases in aspartate aminotransferase (AST) activities, gamma-glutamyltransferase (GGT) activities, and total bilirubin concentration. These changes were most pronounced on Day 14 and partially to fully resolved at later intervals. These changes were considered 4D-310 and 4D-C102.CAG-EGFP-related, and were indicative of hepatocellular and/or hepatobiliary effects. No microscopic correlates were observed at termination.

Also at $5.0\times10^{13}$ vg/kg 4D-C102.CAG-EGFP, there was a transient minimal decrease in mean urea nitrogen concentration on Day 21, and minimal to mild decreases in albumin concentrations beginning on Day 35, which were considered 4D-C102.CAG-EGFP-related. The hepatocellular effects discussed above may have contributed to these changes. At $\geq 3.0\times10^{12}$ vg/kg 4D-310 there were transient minimal to mild increases in creatine kinase (CK) activities on Day 7, which were considered 4D-310-related and indicative of a minor muscle effect. No microscopic correlates were observed at termination.

GLA Pharmacodynamics and Biodistribution—Circulating (plasma) GLA protein was elevated in a somewhat dose responsive manner beginning on Day 15 (the first post dose timepoint tested) through termination. By Day 15, plasma GLA levels increased in 1 of 3 animals at $3.0\times10^{12}$ vg/kg 4D-310 (up to 23.6×), 3 of 3 animals at $1.0\times10^{13}$ vg/kg 4D-310 (up to 8.1×) and 3 of 3 animals at $5.0\times10^{13}$ vg/kg 4D-310 (up to 152.2×). Plasma GLA levels were generally similar (within approximately 2.5-fold of the Day 15 value) from Day 15 through the day of necropsy. At study termination in animals administered 4D-310, GLA DNA was found in most tissues tested in a somewhat dose responsive manner. In animals administered $3.0\times10^{12}$ vg/kg 4D-310, vector copies/ug of DNA ranged from 51.72 to $6.3\times10^6$ with a small subset of tissues having undetectable levels of GLA DNA. At $1.0\times10^{13}$ vg/kg 4D-310, GLA DNA was found in all tissues assayed with copies per ug of DNA ranging from 178 to $3.4\times10^6$. Similarly, at $5.0\times10^{13}$ vg/kg 4D-310, GLA DNA was detectable in all tissues assayed with copies per ug of DNA ranging from 168 to $21.1\times10^6$.

Translation was confirmed by detectable GLA protein in a subset of tissues including liver, carotid artery, heart (including left ventricular free wall and left atrium), lung, aorta, a subset of skeletal muscles (deltoid, pectoralis major and diaphragm), kidney and brain (left hemisphere). See FIGS. 21A-B and 22A-B. The greatest expression of GLA was seen in the liver (up to 21.1×), carotid artery (up to 15.5×), left ventricular free wall (up to 12.2×), and lung (up to 10.1×). A lower level of GLA expression (<10×) was noted in the aorta (up to 7.4×), deltoid (up to 4.3×) diaphragm (up to 3.7×), pectoralis major (up to 3.4×), kidney (2.5×), bicep femoris (2.5×), brain (up to 2.4×), left atrium (2.2×). Elevation in GLA was occasionally, though not always, dose responsive.

EGFP Pharmacodynamics and Biodistribution—At study termination in animals administered $5.0\times10^{13}$ vg/kg 4D-C102.CAG-EGFP, EGFP DNA was found in most tissues tested, the tissues exhibiting the highest levels of vector derived gene expression were the left ventricular free wall and ventricular septum (heart), the left and right liver lobes, the carotid blood vessel, and right ventricle (heart). The levels of gene expression (RNA) observed were approximately 1.5× higher in the 2 heart samples compared to the liver samples. The carotid blood vessel and right ventricle heart samples showed similar results with DNA vector levels ~128× and ~69× higher in the liver samples, while the gene expression levels were approximately equal between the blood vessel and liver samples and only 2× higher in the liver samples versus the right ventricle heart samples. Translation of the GFP protein was observed in most tissues assayed and generally aligned with the biodistribution and gene expression data. The greatest expression (marked increases) of GFP was seen in the heart (up to 8,956,503×), blood vessels (up to 22,991×), and liver (up to 5,194×). Moderate GFP expression was noted in the kidney, deltoid and diaphragm muscles, up 247×, 989× and 347×, respectively. There was minimal expression observed in the brain, nerve, tongue, spinal cord, bicep and tricep muscles. Taken together, a single IV infusion of 4D-310 or 4D-C102.CAG-EGFP was well tolerated in male cynomolgus monkeys up to $5.0 \times 10^{13}$ vg/kg (the highest dose tested for 4D-310 and the only dose tested for 4D-C102.CAG-EGFP) with measurable vector DNA, gene expression (RNA and protein) in various tissues most notably the liver, heart and blood vessels. Due to the lack of any adverse changes, the $5.0 \times 10^{13}$ vg/kg dose level was determined to be the no-observed-adverse-effect level (NOAEL) for both 4D-310 or 4D-C102.CAG-EGFP under the conditions of this study.

Conclusion

A single intravenous infusion of 4D-310 or 4D-C102.CAG EGFP was well tolerated in male cynomolgus monkeys up to $5.0 \times 10^{13}$ vg/kg (the highest dose tested for 4D-310 and the only dose tested for 4D-C102.CAG-EGFP) with measurable vector DNA, gene expression (RNA and protein) in various tissues most notably in the liver, heart and blood vessels. Due to the lack of any adverse changes, the $5.0 \times 10^{13}$ vg/kg dose level was determined to be the no-observed-adverse-effect level (NOAEL) for both 4D-310 and 4D-C102.CAG-EGFP under the conditions of this study.

Vector genomes, RNA message and functional protein were observed in the heart, especially at the high ($5 \times 10^{13}$ vg/kg) dose. Vector genomes and RNA message appeared to correlate. RNA message and AGA activity also appeared to correlate. AGA activity data in Fabry-relevant tissues was confirmed by IHC. Measured levels of RNA message and protein with EGFP were lower than those measured with GLA.

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

The invention claimed is:

1. A method for treating Fabry disease, the method comprising administering to a human subject with Fabry disease a recombinant adeno-associated virus (rAAV) vector comprising: (a) a variant AAV capsid protein comprising a heterologous peptide insertion with a length of 5 to 20 amino acids covalently inserted in the GI-loop of the capsid protein relative to a corresponding parental AAV capsid protein, wherein the peptide insertion comprises the amino acid sequence NKTTNKD (SEQ ID NO:7) and (ii) a heterologous nucleic acid comprising a nucleotide sequence encoding human α-galactosidase A (AGA) protein, wherein said nucleic acid is codon optimized for expression in human cells, wherein said nucleic acid comprises from 5' to 3': (a) an AAV2 terminal repeat, (b) a CAO promoter, (c) the nucleotide sequence set forth in SEQ ID NO: 1, (d) a polyadenylation sequence and (e) an AAV2 terminal repeat.

2. The method according to claim 1, wherein the insertion peptide has from 1 to 3 spacer amino acids ($Y_1$-$Y_3$) at the amino and/or carboxyl terminus of amino acid sequence NKTTNKD (SEQ ID NO:7).

3. The method according to claim 2, wherein the insertion peptide is LANKTTNKDA (SEQ ID NO:8).

4. The method according to claim 1, wherein the variant capsid protein comprises a V7081 amino acid substitution to VP1 of AAV2 (SEQ ID NO: 9) or the corresponding position in the capsid protein of another AAV serotype and wherein the variant capsid protein comprises an amino acid sequence at least 90% identical to the entire length of the amino acid sequence set forth as SEQ ID NO: 4.

5. The method according to claim 4, wherein the variant capsid protein comprises an amino acid sequence at least 95% identical to the entire length of the amino acid sequence set forth in SEQ ID NO:4.

6. The method according to claim 3, wherein the insertion site is located between two adjacent amino acids at a position between amino acids 570 and 611 of VP1 of AAV2 (SEQ ID NO:9), or the corresponding position in the capsid protein of another AAV serotype.

7. The method according to claim 3, wherein the insertion site is located between amino acids corresponding to amino acids 587 and 588 of VP1 of AAV2 (SEQ ID NO:9) or between amino acids corresponding to amino acids 588 and 589 of VP1 of AAV2 (SEQ ID NO:9) or the corresponding position in the capsid protein of another AAV serotype.

8. The method of claim 1, wherein said rAAV vector is administered to said subject by intravenous and/or intramuscular injection.

9. The method of claim 1, wherein the method comprises a single intravenous administration of at least $1\times10^8$ of the rAAV vector.

10. The method of claim 1, wherein the method comprises a single intravenous administration of $1\times10^{12}$ vg/kg to $1\times10^{14}$ vg/kg of the rAAV vector.

* * * * *

UNITED STATES PATENT AND TRADEMARK OFFICE
CERTIFICATE OF CORRECTION

PATENT NO. : 11,802,278 B2
APPLICATION NO. : 18/045650
DATED : October 31, 2023
INVENTOR(S) : David H. Kirn et al.

It is certified that error appears in the above-identified patent and that said Letters Patent is hereby corrected as shown below:

In the Claims

In Column 65, Claim 1, Line 46, "GI-loop" should read -- GH-loop --.

In Column 65, Claim 1, Line 54, "CAO" should read -- CAG --.

In Column 65, Claim 4, Line 64, "V7081" should read -- V708I --.

Signed and Sealed this
Twelfth Day of December, 2023

Katherine Kelly Vidal
*Director of the United States Patent and Trademark Office*